US011667677B2

(12) United States Patent
Tak et al.

(10) Patent No.: US 11,667,677 B2
(45) Date of Patent: Jun. 6, 2023

(54) INDUCIBLE, TUNABLE, AND MULTIPLEX HUMAN GENE REGULATION USING CRISPR-CPF1

(71) Applicant: The General Hospital Corporation, Boston, MA (US)

(72) Inventors: Y. Esther Tak, Charlestown, MA (US); Benjamin Kleinstiver, Medford, MA (US); J. Keith Joung, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 380 days.

(21) Appl. No.: 16/606,680

(22) PCT Filed: Apr. 23, 2018

(86) PCT No.: PCT/US2018/028898
§ 371 (c)(1),
(2) Date: Oct. 18, 2019

(87) PCT Pub. No.: WO2018/195540
PCT Pub. Date: Oct. 25, 2018

(65) Prior Publication Data
US 2021/0309701 A1 Oct. 7, 2021

Related U.S. Application Data

(60) Provisional application No. 62/488,585, filed on Apr. 21, 2017.

(51) Int. Cl.
| *C07K 14/005* | (2006.01) |
| *C12N 9/22* | (2006.01) |
| *C12N 9/52* | (2006.01) |
| *C12N 15/11* | (2006.01) |
| *C12N 15/62* | (2006.01) |
| *A61K 38/00* | (2006.01) |

(52) U.S. Cl.
CPC ............ *C07K 14/005* (2013.01); *C12N 9/22* (2013.01); *C12N 9/52* (2013.01); *C12N 15/111* (2013.01); *C12N 15/62* (2013.01); *A61K 38/00* (2013.01); *C07K 2319/03* (2013.01); *C12N 2310/153* (2013.01); *C12N 2310/20* (2017.05); *C12N 2710/16222* (2013.01); *C12N 2800/30* (2013.01)

(58) Field of Classification Search
CPC ...... C12N 2710/16222; C12N 2800/30; C12N 15/63; C12N 2310/20; C12N 15/111; C12N 9/52; C12N 2310/153; C12N 9/22; C12N 15/62; A61K 38/00; C07K 14/005; C07K 2319/03
See application file for complete search history.

(56) References Cited

U.S. PATENT DOCUMENTS

| 10,793,828 B2* | 10/2020 | Haugwitz ............... C12N 9/003 |
| 11,286,478 B2* | 3/2022 | Zhang ..................... C12N 15/63 |
| 2003/0017149 A1 | 1/2003 | Hoeffler et al. |
| 2007/0020627 A1 | 1/2007 | Barbas, III |
| 2007/0213269 A1 | 9/2007 | Barbas, III et al. |
| 2011/0236894 A1 | 9/2011 | Rao et al. |
| 2011/0294873 A1 | 12/2011 | Mermod et al. |
| 2012/0115227 A1 | 5/2012 | Cohen-Haguenauer et al. |
| 2015/0315252 A1 | 11/2015 | Haugwitz et al. |
| 2016/0208243 A1 | 7/2016 | Zhang et al. |
| 2016/0215280 A1 | 7/2016 | Fanucchi et al. |
| 2017/0175136 A1 | 6/2017 | Stamatoyannopoulos et al. |
| 2019/0351074 A1 | 11/2019 | Ahituv et al. |

FOREIGN PATENT DOCUMENTS

| WO | WO 2003/072788 | 9/2003 |
| WO | WO 2012/047726 | 4/2012 |
| WO | WO 2013/176772 | 11/2013 |
| WO | WO 2014/152432 | 9/2014 |
| WO | WO 2015/139139 | 9/2015 |
| WO | WO 2016/115355 | 7/2016 |
| WO | WO 2016/191684 | 12/2016 |
| WO | WO 2016/205711 | 12/2016 |
| WO | WO 2017/015015 | 1/2017 |
| WO | WO 2017/031370 | 2/2017 |
| WO | WO 2017/141173 | 8/2017 |
| WO | WO 2018/071892 | 4/2018 |
| WO | WO 2019/222670 | 11/2019 |
| WO | WO 2021/108501 | 6/2021 |
| WO | WO 2021/243289 | 12/2021 |

OTHER PUBLICATIONS

Dong et al., The crystal structure of Cpf1 in complex with CRISPR RNA. Nature, 2016, vol. 532: 522-526. (Year: 2016).*
Tak et al., Inducible, tunable and multiplex human gene regulation using CRISPR-Cpf1-based transcription factors. bioRxiv, Jun. 15, 2017, pp. 1-21. (Year: 2017).*
Andersson et al., "A Unified Architecture of Transcriptional Regulatory Elements," Trends in Genetics, Aug. 2015, 31(8):426-433.
Baron-Benhamou et al., "Using the Lambda N Peptide to Tether Proteins to RNAs," Methods in Molecular Biology, Jan. 2004, 257:135-153.
Bikard et al., "Programmable repression and activation of bacterial gene expression using an engineered CRISPR-Cas system," Nucleic Acids Research, Jun. 2013, 41(15):7429-7437.
Bird et al., "A dual role for zinc fingers in both DNA binding and zinc sensing by the Zap1 transcriptional activator," EMBO J., 2000, 19(14):3704-3713.
International Search Report and Written Opinion in International Appln. No. PCT/US2014/027335, dated Jul. 16, 2014, 13 pages.

(Continued)

*Primary Examiner* — Ganapathirama Raghu
(74) *Attorney, Agent, or Firm* — Fish & Richardson P.C.

(57) ABSTRACT

Drug-inducible, tunable, and multiplexable Clustered Regularly Interspaced Short Palindromic Repeats from *Prevotella* and *Francisella* 1 (Cpf1)-based activators, and methods of use thereof.

14 Claims, 12 Drawing Sheets
Specification includes a Sequence Listing.

(56) References Cited

OTHER PUBLICATIONS

International Search Report and Written Opinion in International Appln. No. PCT/US2017/056738, dated Mar. 6, 2018, 16 pages.
International Search Report and Written Opinion in International Appln. No. PCT/US2019/032937, dated Oct. 17, 2019, 17 pages.
International Search Report and Written Opinion in International Appln. No. PCT/US2020/062166, dated May 4, 2021, 13 pages.
International Search Report and Written Opinion in International Appln. No. PCT/US2021/034996, dated Sep. 16, 2021, 12 pages.
Khalil et al., "A Synthetic Biology Framework for Programming Eukaryotic Transcription Functions," Cell, Aug. 2012, 150(3):647-658.
Li et al., "Identification of critical base pairs required for CTCF binding in motif M1 and M2," Protein Cell, Mar. 2017, 8(7):544-549.
Office Action in Australian Appln. No. 2018254616, dated Oct. 11, 2021, 5 pages.
Office Action in Japanese Appln. No. 2019-556605, dated Mar. 29, 2022, 8 pages (with English translation).
Qi et al., "Repurposing CRISPR as an RNA-Guided Platform for Sequence-Specific Control of Gene Expression," Cell, Feb. 2013, 152:1173-1183.
Rojano et al., "Regulatory variants: from detection to predicting impact," Briefings in Bioinformatics, Sep. 2019, 20(5):1639-1654.
Adamson et al., "A Multiplexed Single-Cell CRISPR Screening Platform Enables Systematic Dissection of the Unfolded Protein Response," Cell, Dec. 2016, 167(7):1867-1882.
Bao et al., "Orthogonal Genetic Regulation in Human Cells Using Chemically Induced CRISPR/Cas9 Activators," ACS Synthetic Biology, Apr. 2017, 6(4):686-693.
Chavez et al., "Comparison of Cas9 activators in multiple species," Nature Methods, Jul. 2016, 13(7):563-567.
Chavez et al., "Highly efficient Cas9-mediated transcriptional programming," Nature Methods, Apr. 2015, 12(4):326-328.
Cong et al., "Multiplex genome engineering using CRISPR/Cas systems," Science, Feb. 2013, 339(6121):819-823.
Deltcheva et al., "Crispr RNA maturation by trans-encoded small RNA and host factor RNase III," Nature, Mar. 2011, 471(7340):602-607.
Dong et al., "The crystal structure of Cpf1 in complex with CRISPR RNA," Nature, Apr. 2016, 532(7600):522-526.
Doudna & Charpentier, "Genome editing. The new frontier of genome engineering with CRISPR-Cas9," Science, Nov. 2014, 346(6213):9258096.
Fagerlund et al., "The Cpf1 CRISPR-Cas protein expands genome-editing tools," Genome Biol., Dec. 2015, 16(1):251.
Fonfara et al., "The CRISPR-associated DNA-cleaving enzyme Cpf1 also processes precursor CRISPR RNA," Nature, Apr. 2016, 532(7600):517-521.
Frock et al., "Genome-wide detection of DNA double-stranded breaks induced by engineered nucleases," Nat. Biotechnol., Feb. 2015, 33(2):979-186.
Gilbert et al., "Genome-Scale CRISPR-Mediated Control of Gene Repression and Activation," Cell, Oct. 2014, 159(3):647-661.
Guo et al., "An inducible CRISPR-ON system for controllable gene activation in human pluripotent stem cells," Protein & Cell, May 2017, 8(5):379-393.
Han al., "Synergistic dmg combinations for cancer identified in a CRISPR screen for pairwise genetic interactions," Nature Biotechnology, May 2017, 35(5):463, 15 pages.
Hsu et al., "Development and applications of CRISPR-Cas9 for genome engineering," Cell, Jun. 2014, 157(6):9262-1278.
Jinek et al., "A programmable dual-RNA-guided DNA endonuclease in adaptive bacterial immunity," Science, Aug. 2012 337(6096):816-821.
Jinek et al., "RNA-programmed genome editing in human cells," Elife 2, Jan. 2013, 2:e00471, 9 pages.
Kabadi et al., "Multiplex CRISPR/Cas9-based genome engineering from a single lentiviral vector," Nucleic Acids Res., 2014, 42(19):e147.

Kim et al., "Digenome-seq: genome-wide profiling of CRISPR-Cas9 off-target effects in human cells," Nat. Methods, 12(3):237-243.
Kim et al., "Efficient Transcriptional Gene Repression by Type V-A CRISPR-Cpf1 from Eubacterium eligens," ACS Synthetic Biology, Jul. 2017, 6(7):1273-1282.
Kim et al., "Genome-wide analysis reveals specificities of Cpf1 endonucleases in human cells," Nature Biotechnology, Aug. 2016, 34(8):863-868.
Kleinstiver et al., "Genome-wide specificities of CRISPR-Cas Cpf1 nucleases in human cells," Nature Biotechnology, Aug. 2016, 34(8):869-874.
Kleinstiver et al., "High-fidelity CRISPR-Cas9 nucleases with no detectable genome-wide off-target effects," Nature, Jan. 2016, 529(7587):490-495.
Konermann et al., "Genome-scale transcriptional activation by an engineered CRISPR-Cas9 complex," Nature, Jan. 2015, 517(7536):583-588.
Lin et al., "A CRISPR Approach for Reactivating Latent HIV-1," Molecular Therapy, Mar. 2016, 24(3):416-418.
Lin et al., "Cellular toxicity induced by SRF-mediated transcriptional squelching," Toxicological Sciences, Mar. 2007, 96(1):83-91.
Maeder et al., "CRISPR RNA-guided activation of endogenous human genes," Nat. Methods, Oct. 2013, 10(10):977-979.
Maeder et al., "Genome-editing Technologies for Gene and Cell Therapy," Mol. Ther., Mar. 2016, 24(3):430-436.
Maji et al., "Multidimensional chemical control of CRISPR-Cas9," Nature Chemical Biology, Jan. 2017, 13(1):9-11.
Makarova et al., "An updated evolutionary classification of CRISPR-Cas systems," Nat. Rev. Microbiol., Nov. 2015, 13(11):722-736.
Mali et al., "RNA-guided human genome engineering via Cas9," Science, Feb. 2013, 339(6121):823-826.
Matis et al., "Differential and opposed transcriptional effects of protein fusions containing the VP16 activation domain," FEBS Letters, Jun. 2001, 499(1-2):92-96.
Nissim et al., "Multiplexed and programmable regulation of gene networks with an integrated RNA and CRISPR/Cas toolkit in human cells," Molecular Cell, May 2014, 54(4):698-710.
PCT International Preliminary Report on Patentability in International Appln. No. PCT/US18/28898, dated Oct. 22, 2019, 9 pages.
PCT International Search Report and Written Opinion in International Appln. No. PCT/US18/28898, dated Jul. 23, 2018, 12 pages.
Perez-Pinera et al., "RNA-guided gene activation by CRISPR-Cas9-based transcription factors," Nat. Methods, Oct. 2013, 10(10):973-976.
Polstein & Gersbach, "A light-inducible CRISPR-Cas9 system for control of endogenous gene activation," Nature Chemical Biology, Mar. 2015, 11(3):198-200.
Rivera et al., "Dimerizer-mediated regulation of gene expression in vivo," Cold Spring Harbor Protocols, Jul. 2012, (7):821-824.
Sander & Joung, "CRISPR-Cas systems for editing, regulating and targeting genomes," Nat. Biotechnol., Apr. 2014, 32(4):347-355.
Schunder et al., "First indication for a functional CRISPR/Cas system in Francisella tularensis," Int. J. Med. Microbiol., Mar. 2013, 303(2):51-60.
Shen et al., "Combinatorial CRISPR-Cas9 screens for de novo mapping of genetic interactions," Nature Methods, Jun. 2017, 14(6):573, 9 pages.
Slaymaker et al., "Rationally engineered Cas9 nucleases with improved specificity," Science, Jan. 2016, 351(6268):84-88.
Tang et al., "A CRISPR-Cpf1 system for efficient genome editing and transcriptional repression in plants," Nature Plants, Feb. 2017, 3:17018.
Tsai et al., "Dimeric CRISPR RNA-guided FokI nucleases for highly specific genome editing," Nat. Biotechnol., Jun. 2014, 32(6):569-576.
Tsai et al., "GUIDE—seq enables genome-wide profiling of off-target cleavage by CRISPR-Cas nucleases," Nat. Biotechnol., Feb. 2015, 33(2):187-197.
Wang et al., "Unbiased detection of off-target cleavage by CRISPR-Cas9 and TALENs using integrase-defective lentiviral vectors," Nat. Biotechnol., Feb. 2015, 33(2):175-178.

(56) References Cited

OTHER PUBLICATIONS

Wong et al., "Multiplexed barcoded CRISPR-Cas9 screening enabled by CombiGEM," Proc. Natl. Acad. Sci. USA., Mar. 2016, 113(9):2544-2549.

Wright et al., "Biology and Applications of CRISPR Systems: Harnessing Nature's Toolbox for Genome Engineering," Cell, Jan. 2016, 164(1-2):29-44.

Xie et al., "Boosting CRISPR/Cas9 multiplex editing capability with the endogenous tRNA-processing system," Proc. Natl. Acad. Sci. USA., Mar. 2015, 112(11):3570-3575.

Xu et al., "Empower multiplex cell and tissue-specific CRISPR-mediated gene manipulation with self-cleaving ribozymes and tRNA," Nucleic Acids Res., Mar. 2017, 45(5):e28.

Yamano et al., "Crystal structure of Cpf1 in complex with guide RNA and target DNA," Cell, May 2016, 165(4):949-962.

Zetsche et al., "A split-Cas9 architecture for inducible genome editing and transcription modulation," Nature Biotechnology, Feb. 2015, 33(2):139-142.

Zetsche et al., "Cpf1 is a single RNA-guided endonuclease of a class 2 CRISPR-Cas system," Cell, Oct. 2015, 163(3):759-771.

Zetsche et al., "Multiplex gene editing by CRISPR-Cpf1 using a single crRNA array," Nature Biotechnology, 35(1):31-34.

Notice of Acceptance in Australian Appln. No. 2018254616, dated Jul. 13, 2022, 4 pages.

EP Extended European Search Report in European Appln. No. 18787309.6, dated Jan. 11, 2021, 11 pages.

Gao et al., "Complex transcriptional modulation with orthogonal and inducible dCas9 regulators," Nature Methods, Dec. 2016, 13(12):1043-1049.

Tak et al.: "Inducible and multiplex gene regulation using CRISPR-Cpf1-based transcription factors," Nature Methods, Oct. 2017, 14(12):1163-1166.

Tang et al., "A CRISPR-Cpf1 system for efficient genome editing and transcriptional repression in plants," Nature Plants, Feb. 2017, 3(3):1-5.

Zhang et al., "Multiplex gene regulation by CRISPR-ddCpf1," Cell Discovery, Jun. 2017, 3(6):17018, 9 pages.

Office Action in Japanese Appln. No. 2019-556605, dated Oct. 18, 2022, 6 pages (with English translation).

Office Action in Chinese Appln. No. 201880041218.8, dated Feb. 8, 2023, 27 pages (with English translation).

\* cited by examiner

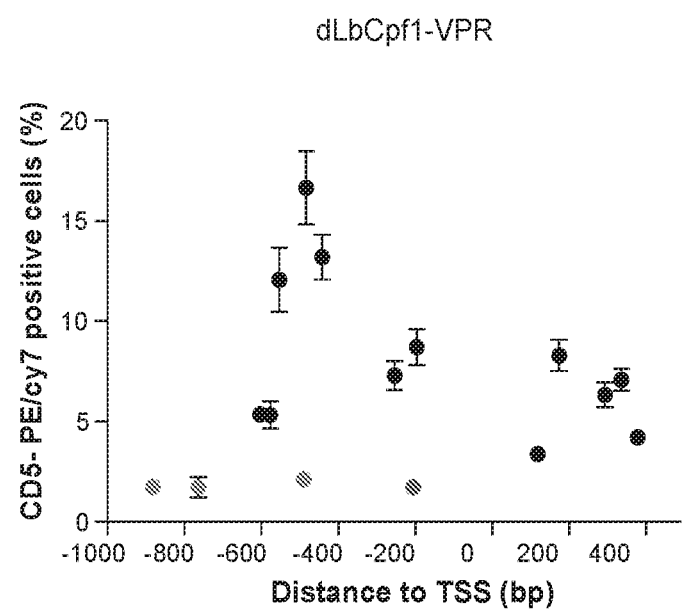
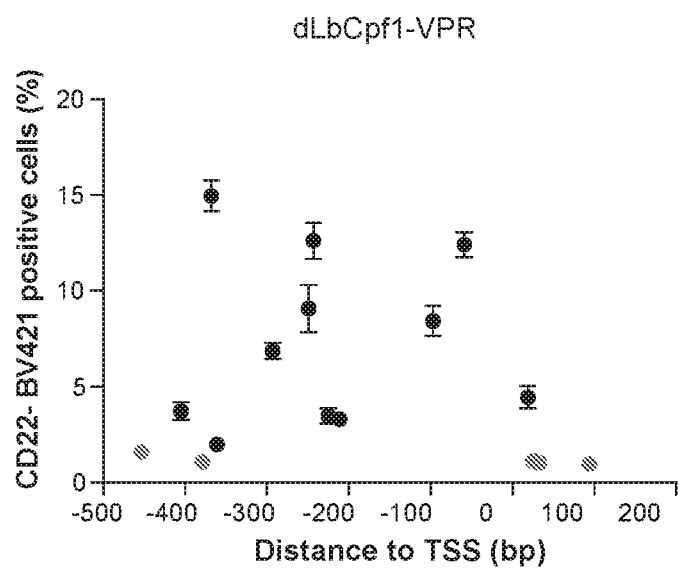
FIG. 1C

SEQUENCE LISTING

<160> NUMBER OF SEQ ID NOS: 58

<210> SEQ ID NO 1
<211> LENGTH: 1246
<212> TYPE: PRT

<213> ORGANISM: Lachnospiraceae bacterium

<400> SEQUENCE: 1

Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
        275                 280                 285

Pro Lys Phe Lys Pro Leu Tyr Lys Gln Val Leu Ser Asp Arg Glu Ser
    290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
        355                 360                 365

Ile Phe Gly Glu Trp Asn Val Ile Arg Asp Lys Trp Asn Ala Glu Tyr
    370                 375                 380

Asp Asp Ile His Leu Lys Lys Lys Ala Val Val Thr Glu Lys Tyr Glu
385                 390                 395                 400

-continued

Asp Asp Arg Arg Lys Ser Phe Lys Lys Ile Gly Ser Phe Ser Leu Glu
            405                 410                 415

Gln Leu Gln Glu Tyr Ala Asp Ala Asp Leu Ser Val Val Glu Lys Leu
        420                 425                 430

Lys Glu Ile Ile Ile Gln Lys Val Asp Glu Ile Tyr Lys Val Tyr Gly
        435                 440                 445

Ser Ser Glu Lys Leu Phe Asp Ala Asp Phe Val Leu Glu Lys Ser Leu
    450                 455                 460

Lys Lys Asn Asp Ala Val Ala Ile Met Lys Asp Leu Leu Asp Ser
465                 470                 475                 480

Val Lys Ser Phe Glu Asn Tyr Ile Lys Ala Phe Phe Gly Glu Gly Lys
            485                 490                 495

Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
            515                 520                 525

Val Thr Gln Lys Pro Tyr Ser Lys Asp Lys Phe Lys Leu Tyr Phe Gln
        530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Leu Ala Ile Met
            565                 570                 575

Asp Lys Lys Tyr Ala Lys Cys Leu Gln Lys Ile Asp Lys Asp Val
        580                 585                 590

Asn Gly Asn Tyr Glu Lys Ile Asn Tyr Lys Leu Leu Pro Gly Pro Asn
            595                 600                 605

Lys Met Leu Pro Lys Val Phe Phe Ser Lys Lys Trp Met Ala Tyr Tyr
        610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
            645                 650                 655

Phe Lys Asp Ser Ile Ser Arg Tyr Pro Lys Trp Ser Asn Ala Tyr Asp
            660                 665                 670

Phe Asn Phe Ser Glu Thr Glu Lys Tyr Lys Asp Ile Ala Gly Phe Tyr
        675                 680                 685

Arg Glu Val Glu Glu Gln Gly Tyr Lys Val Ser Phe Glu Ser Ala Ser
        690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
            725                 730                 735

Leu His Thr Met Tyr Phe Lys Leu Leu Phe Asp Glu Asn Asn His Gly
            740                 745                 750

Gln Ile Arg Leu Ser Gly Gly Ala Glu Leu Phe Met Arg Arg Ala Ser
        755                 760                 765

Leu Lys Lys Glu Glu Leu Val Val His Pro Ala Asn Ser Pro Ile Ala
        770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
            805                 810                 815

Pro Ile Ala Ile Asn Lys Cys Pro Lys Asn Ile Phe Lys Ile Asn Thr

-continued

```
            820                 825                 830
Glu Val Arg Val Leu Lys His Asp Asp Asn Pro Tyr Val Ile Gly
            835                 840                 845

Ile Asp Arg Gly Glu Arg Asn Leu Leu Tyr Ile Val Val Asp Gly
            850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                    885                 890                 895

Lys Glu Lys Glu Arg Phe Glu Ala Arg Gln Asn Trp Thr Ser Ile Glu
                900                 905                 910

Asn Ile Lys Glu Leu Lys Ala Gly Tyr Ile Ser Gln Val Val His Lys
            915                 920                 925

Ile Cys Glu Leu Val Glu Lys Tyr Asp Ala Val Ile Ala Leu Glu Asp
            930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
                980                 985                 990

Gln Ile Thr Asn Lys Phe Glu Ser Phe Lys Ser Met Ser Thr Gln Asn
            995                 1000                1005

Gly Phe Ile Phe Tyr Ile Pro Ala Trp Leu Thr Ser Lys Ile Asp
            1010                1015                1020

Pro Ser Thr Gly Phe Val Asn Leu Leu Lys Thr Lys Tyr Thr Ser
            1025                1030                1035

Ile Ala Asp Ser Lys Lys Phe Ile Ser Ser Phe Asp Arg Ile Met
            1040                1045                1050

Tyr Val Pro Glu Glu Asp Leu Phe Glu Phe Ala Leu Asp Tyr Lys
            1055                1060                1065

Asn Phe Ser Arg Thr Asp Ala Asp Tyr Ile Lys Lys Trp Lys Leu
            1070                1075                1080

Tyr Ser Tyr Gly Asn Arg Ile Arg Ile Phe Arg Asn Pro Lys Lys
            1085                1090                1095

Asn Asn Val Phe Asp Trp Glu Glu Val Cys Leu Thr Ser Ala Tyr
            1100                1105                1110

Lys Glu Leu Phe Asn Lys Tyr Gly Ile Asn Tyr Gln Gln Gly Asp
            1115                1120                1125

Ile Arg Ala Leu Leu Cys Glu Gln Ser Asp Lys Ala Phe Tyr Ser
            1130                1135                1140

Ser Phe Met Ala Leu Met Ser Leu Met Leu Gln Met Arg Asn Ser
            1145                1150                1155

Ile Thr Gly Arg Thr Asp Val Asp Phe Leu Ile Ser Pro Val Lys
            1160                1165                1170

Asn Ser Asp Gly Ile Phe Tyr Asp Ser Arg Asn Tyr Glu Ala Gln
            1175                1180                1185

Glu Asn Ala Ile Leu Pro Lys Asn Ala Asp Ala Asn Gly Ala Tyr
            1190                1195                1200

Asn Ile Ala Arg Lys Val Leu Trp Ala Ile Gly Gln Phe Lys Lys
            1205                1210                1215

Ala Glu Asp Glu Lys Leu Asp Lys Val Lys Ile Ala Ile Ser Asn
            1220                1225                1230
```

```
Lys Glu  Trp Leu Glu Tyr Ala  Gln Thr Ser Val Lys  His
    1235             1240             1245
```

<210> SEQ ID NO 2
<211> LENGTH: 1228
<212> TYPE: PRT
<213> ORGANISM: Lachnospiraceae bacterium

<400> SEQUENCE: 2

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
```

```
                355                 360                 365
Ile His Leu Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
            450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
            530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
            675                 680                 685

Glu Val Asp Lys Leu Val Glu Gly Lys Leu Tyr Met Phe Gln Ile
            690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
        770                 775                 780
```

-continued

```
Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Asp Gly Lys Gly
        835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
            885                 890                 895

Lys Glu Leu Lys Ala Gly Tyr Ile Ser Gln Val Val His Lys Ile Cys
        900                 905                 910

Glu Leu Val Glu Lys Tyr Asp Ala Val Ile Ala Leu Glu Asp Leu Asn
    915                 920                 925

Ser Gly Phe Lys Asn Ser Arg Val Lys Val Glu Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
            965                 970                 975

Thr Asn Lys Phe Glu Ser Phe Lys Ser Met Ser Thr Gln Asn Gly Phe
        980                 985                 990

Ile Phe Tyr Ile Pro Ala Trp Leu Thr Ser Lys Ile Asp Pro Ser Thr
    995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185
```

```
Arg Lys   Val Leu Trp Ala Ile   Gly Gln Phe Lys   Ala Glu Asp
    1190                  1195                1200

Glu Lys   Leu Asp Lys Val Lys   Ile Ala Ile Ser   Asn Lys Glu Trp
    1205                  1210                1215

Leu Glu   Tyr Ala Gln Thr Ser   Val Lys His
    1220                  1225

<210> SEQ ID NO 3
<211> LENGTH: 4
<212> TYPE: PRT
<213> ORGANISM: Artificial
<220> FEATURE:
<223> OTHER INFORMATION: linker peptide

<400> SEQUENCE: 3

Gly Gly Gly Ser
1

<210> SEQ ID NO 4
<211> LENGTH: 5
<212> TYPE: PRT
<213> ORGANISM: Artificial
<220> FEATURE:
<223> OTHER INFORMATION: linker peptide

<400> SEQUENCE: 4

Gly Gly Gly Gly Ser
1               5

<210> SEQ ID NO 5
<211> LENGTH: 7
<212> TYPE: PRT
<213> ORGANISM: Artificial
<220> FEATURE:
<223> OTHER INFORMATION: SV40 large T antigen NLS

<400> SEQUENCE: 5

Pro Lys Lys Lys Arg Arg Val
1               5

<210> SEQ ID NO 6
<211> LENGTH: 16
<212> TYPE: PRT
<213> ORGANISM: Artificial
<220> FEATURE:
<223> OTHER INFORMATION: nucleoplasmin NLS

<400> SEQUENCE: 6

Lys Arg Pro Ala Ala Thr Lys Lys Ala Gly Gln Ala Lys Lys Lys Lys
1               5                   10                  15

<210> SEQ ID NO 7
<211> LENGTH: 337
<212> TYPE: DNA
<213> ORGANISM: Artificial
<220> FEATURE:
<223> OTHER INFORMATION: nucleic acid encoding a plurality of Cpf1 gRNAs

<400> SEQUENCE: 7
gagggcctat ttcccatgat tccttcatat ttgcatatac gatacaaggc tgttagagag      60
ataattagaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
```
cgaaacaccg aatttctact aagtgtagat aatttctact aagtgtagat aatttctact    300
aagtgtagat aatttctact aagtgtagat tttttt    337

<210> SEQ ID NO 8
<211> LENGTH: 25
<212> TYPE: DNA
<213> ORGANISM: Artificial
<220> FEATURE:
<223> OTHER INFORMATION: Cpf1 crRNA HBB_ Multiplexed, pair 1, top

<400> SEQUENCE: 8
agattactga tggtatgggg ccaaa    25

<210> SEQ ID NO 9
<211> LENGTH: 31
<212> TYPE: DNA
<213> ORGANISM: Artificial
<220> FEATURE:
<223> OTHER INFORMATION: Cpf1 crRNA HBB_ Multiplexed, pair 1, bottom

<400> SEQUENCE: 9
tagtagaaat tttggcccca taccatcagt a    31

<210> SEQ ID NO 10
<211> LENGTH: 51
<212> TYPE: DNA
<213> ORGANISM: Artificial
<220> FEATURE:
<223> OTHER INFORMATION: Cpf1 crRNA HBB_ Multiplexed, pair 2, top

<400> SEQUENCE: 10
atttctacta agtgtagata agtccaactc ctaagccaga atttctacta a    51

<210> SEQ ID NO 11
<211> LENGTH: 49
<212> TYPE: DNA
<213> ORGANISM: Artificial
<220> FEATURE:
<223> OTHER INFORMATION: Cpf1 crRNA HBB_ Multiplexed, pair 2, bottom

<400> SEQUENCE: 11
atctacactt agtagaaatt ctggcttagg agttggactt atctacact    49

<210> SEQ ID NO 12
<211> LENGTH: 56
<212> TYPE: DNA
<213> ORGANISM: Artificial
<220> FEATURE:
<223> OTHER INFORMATION: Cpf1 crRNA HBB_ Multiplexed, pair 3, top

<400> SEQUENCE: 12
gtgtagatca agtgtattta cgtaatataa tttctactaa gtgtagattt ttttta    56

<210> SEQ ID NO 13
<211> LENGTH: 52
<212> TYPE: DNA
<213> ORGANISM: Artificial
<220> FEATURE:
<223> OTHER INFORMATION: Cpf1 crRNA HBB_ Multiplexed, pair 3, bottom

<400> SEQUENCE: 13
agcttaaaaa aaatctacac ttagtagaaa ttatattacg taaatacact tg    52

<210> SEQ ID NO 14
<211> LENGTH: 25

```
<212> TYPE: DNA
<213> ORGANISM: Artificial
<220> FEATURE:
<223> OTHER INFORMATION: Cpf1 crRNA AR_ Multiplexed, pair 1, top

<400> SEQUENCE: 14
agatagagtc tggatgagaa atgca                                            25

<210> SEQ ID NO 15
<211> LENGTH: 31
<212> TYPE: DNA
<213> ORGANISM: Artificial
<220> FEATURE:
<223> OTHER INFORMATION: Cpf1 crRNA AR_ Multiplexed, pair 1, bottom

<400> SEQUENCE: 15
tagtagaaat tgcatttctc atccagactc t                                     31

<210> SEQ ID NO 16
<211> LENGTH: 51
<212> TYPE: DNA
<213> ORGANISM: Artificial
<220> FEATURE:
<223> OTHER INFORMATION: Cpf1 crRNA AR_ Multiplexed, pair 2, top

<400> SEQUENCE: 16
atttctacta agtgtagatt accctcttct ctgcctttca atttctacta a               51

<210> SEQ ID NO 17
<211> LENGTH: 49
<212> TYPE: DNA
<213> ORGANISM: Artificial
<220> FEATURE:
<223> OTHER INFORMATION: Cpf1 crRNA AR_ Multiplexed, pair 2, bottom

<400> SEQUENCE: 17
atctacactt agtagaaatt gaaaggcaga gaagagggta atctacact                  49

<210> SEQ ID NO 18
<211> LENGTH: 56
<212> TYPE: DNA
<213> ORGANISM: Artificial
<220> FEATURE:
<223> OTHER INFORMATION: Cpf1 crRNA AR_ Multiplexed, pair 3, top

<400> SEQUENCE: 18
gtgtagatct ctaggaaccc tcagccccaa tttctactaa gtgtagattt ttttta          56

<210> SEQ ID NO 19
<211> LENGTH: 52
<212> TYPE: DNA
<213> ORGANISM: Artificial
<220> FEATURE:
<223> OTHER INFORMATION: Cpf1 crRNA AR_ Multiplexed, pair 3, bottom

<400> SEQUENCE: 19
agcttaaaaa aaatctacac ttagtagaaa ttggggctga gggttcctag ag              52

<210> SEQ ID NO 20
<211> LENGTH: 25
<212> TYPE: DNA
<213> ORGANISM: Artificial
<220> FEATURE:
<223> OTHER INFORMATION: Cpf1 crRNA NPY1R_ Multiplexed, pair 1, top

<400> SEQUENCE: 20
```
agataagcct cgggaaactg cccta                                         25

<210> SEQ ID NO 21
<211> LENGTH: 31
<212> TYPE: DNA
<213> ORGANISM: Artificial
<220> FEATURE:
<223> OTHER INFORMATION: Cpf1 crRNA NPY1R_ Multiplexed, pair 1, bottom

<400> SEQUENCE: 21
tagtagaaat tagggcagtt tcccgaggct t                                  31

<210> SEQ ID NO 22
<211> LENGTH: 51
<212> TYPE: DNA
<213> ORGANISM: Artificial
<220> FEATURE:
<223> OTHER INFORMATION: Cpf1 crRNA NPY1R_ Multiplexed, pair 2, top

<400> SEQUENCE: 22
atttctacta agtgtagatt ttgtttgcag gtcagtgcca atttctacta a             51

<210> SEQ ID NO 23
<211> LENGTH: 49
<212> TYPE: DNA
<213> ORGANISM: Artificial
<220> FEATURE:
<223> OTHER INFORMATION: Cpf1 crRNA NPY1R_ Multiplexed, pair 2, bottom

<400> SEQUENCE: 23
atctacactt agtagaaatt ggcactgacc tgcaaacaaa atctacact                49

<210> SEQ ID NO 24
<211> LENGTH: 56
<212> TYPE: DNA
<213> ORGANISM: Artificial
<220> FEATURE:
<223> OTHER INFORMATION: Cpf1 crRNA NPY1R_ Multiplexed, pair 3, top

<400> SEQUENCE: 24
gtgtagatgg ctggcgctcg agctctccaa tttctactaa gtgtagattt tttta        56

<210> SEQ ID NO 25
<211> LENGTH: 52
<212> TYPE: DNA
<213> ORGANISM: Artificial
<220> FEATURE:
<223> OTHER INFORMATION: Cpf1 crRNA NPY1R_ Multiplexed, pair 3, bottom

<400> SEQUENCE: 25
agcttaaaaa aaatctacac ttagtagaaa ttggagagct cgagcgccag cc           52

<210> SEQ ID NO 26
<211> LENGTH: 25
<212> TYPE: DNA
<213> ORGANISM: Artificial
<220> FEATURE:
<223> OTHER INFORMATION: Cpf1 crRNA HBB_AR_NPY1R_Multiplexed, pair 1,
      top

<400> SEQUENCE: 26
agattactga tggtatgggg ccaaa                                         25

<210> SEQ ID NO 27
<211> LENGTH: 31
<212> TYPE: DNA

<213> ORGANISM: Artificial
<220> FEATURE:
<223> OTHER INFORMATION: Cpf1 crRNA HBB_AR_NPY1R_ Multiplexed, pair1, top

<400> SEQUENCE: 27
tagtagaaat tttggcccca taccatcagt a                                   31

<210> SEQ ID NO 28
<211> LENGTH: 51
<212> TYPE: DNA
<213> ORGANISM: Artificial
<220> FEATURE:
<223> OTHER INFORMATION: Cpf1 crRNA HBB_AR_NPY1R_Multiplexed pair2 top

<400> SEQUENCE: 28
atttctacta agtgtagatc tctaggaacc ctcagcccca atttctacta a             51

<210> SEQ ID NO 29
<211> LENGTH: 49
<212> TYPE: DNA
<213> ORGANISM: Artificial
<220> FEATURE:
<223> OTHER INFORMATION: Cpf1 crRNA HBB_AR_NPY1R_Multiplexed pair2 bottom

<400> SEQUENCE: 29
atctacactt agtagaaatt ggggctgagg gttcctagag atctacact                49

<210> SEQ ID NO 30
<211> LENGTH: 56
<212> TYPE: DNA
<213> ORGANISM: Artificial
<220> FEATURE:
<223> OTHER INFORMATION: Cpf1 crRNA HBB_AR_NPY1R_Multiplexed pair3 top

<400> SEQUENCE: 30
gtgtagataa gcctcgggaa actgccctaa tttctactaa gtgtagattt tttta         56

<210> SEQ ID NO 31
<211> LENGTH: 52
<212> TYPE: DNA
<213> ORGANISM: Artificial
<220> FEATURE:
<223> OTHER INFORMATION: Cpf1 crRNA HBB_AR_NPY1R_Multiplexed pair3 bottom

<400> SEQUENCE: 31
agcttaaaaa aaatctacac ttagtagaaa ttagggcagt tcccgaggc tt             52

<210> SEQ ID NO 32
<211> LENGTH: 22
<212> TYPE: DNA
<213> ORGANISM: Artificial
<220> FEATURE:
<223> OTHER INFORMATION: RT-qPCR primer oET_173

<400> SEQUENCE: 32
atggtgagca gagtgcccta tc                                             22

<210> SEQ ID NO 33
<211> LENGTH: 22
<212> TYPE: DNA
<213> ORGANISM: Artificial
<220> FEATURE:
<223> OTHER INFORMATION: RT-qPCR primer oET_174

```
<400> SEQUENCE: 33
atggtccctg gcagtctcca aa                                              22

<210> SEQ ID NO 34
<211> LENGTH: 23
<212> TYPE: DNA
<213> ORGANISM: Artificial
<220> FEATURE:
<223> OTHER INFORMATION: RT-qPCR primer oET_175

<400> SEQUENCE: 34
ccatcggact ctcataggtt gtc                                             23

<210> SEQ ID NO 35
<211> LENGTH: 24
<212> TYPE: DNA
<213> ORGANISM: Artificial
<220> FEATURE:
<223> OTHER INFORMATION: RT-qPCR primer oET_176

<400> SEQUENCE: 35
gacctgtact tattgtctct catc                                            24

<210> SEQ ID NO 36
<211> LENGTH: 20
<212> TYPE: DNA
<213> ORGANISM: Artificial
<220> FEATURE:
<223> OTHER INFORMATION: RT-qPCR primer oET_225

<400> SEQUENCE: 36
gcacgtggat cctgagaact                                                 20

<210> SEQ ID NO 37
<211> LENGTH: 21
<212> TYPE: DNA
<213> ORGANISM: Artificial
<220> FEATURE:
<223> OTHER INFORMATION: RT-qPCR primer oET_226

<400> SEQUENCE: 37
attggacagc aagaaagcga g                                               21

<210> SEQ ID NO 38
<211> LENGTH: 20
<212> TYPE: DNA
<213> ORGANISM: Artificial
<220> FEATURE:
<223> OTHER INFORMATION: Lb crRNA direct repeat

<400> SEQUENCE: 38
aatttctact aagtgtagat                                                 20

<210> SEQ ID NO 39
<211> LENGTH: 24
<212> TYPE: DNA
<213> ORGANISM: Artificial
<220> FEATURE:
<223> OTHER INFORMATION: Cpf1 crRNA HBB_P_1 guide

<400> SEQUENCE: 39
tttgtactga tggtatgggg ccaa                                            24

<210> SEQ ID NO 40
<211> LENGTH: 24
```

```
<212> TYPE: DNA
<213> ORGANISM: Artificial
<220> FEATURE:
<223> OTHER INFORMATION: Cpf1 crRNA HBB_P_2 guide

<400> SEQUENCE: 40
tttgaagtcc aactcctaag ccag                                          24

<210> SEQ ID NO 41
<211> LENGTH: 24
<212> TYPE: DNA
<213> ORGANISM: Artificial
<220> FEATURE:
<223> OTHER INFORMATION: Cpf1 crRNA HBB_P_3 guide

<400> SEQUENCE: 41
tttgcaagtg tatttacgta atat                                          24

<210> SEQ ID NO 42
<211> LENGTH: 24
<212> TYPE: DNA
<213> ORGANISM: Artificial
<220> FEATURE:
<223> OTHER INFORMATION: Cpf1 crRNA AR_P_1 guide

<400> SEQUENCE: 42
tttgagagtc tggatgagaa atgc                                          24

<210> SEQ ID NO 43
<211> LENGTH: 24
<212> TYPE: DNA
<213> ORGANISM: Artificial
<220> FEATURE:
<223> OTHER INFORMATION: Cpf1 crRNA AR_P_2 guide

<400> SEQUENCE: 43
tttctaccct cttctctgcc tttc                                          24

<210> SEQ ID NO 44
<211> LENGTH: 24
<212> TYPE: DNA
<213> ORGANISM: Artificial
<220> FEATURE:
<223> OTHER INFORMATION: Cpf1 crRNA AR_P_3 guide

<400> SEQUENCE: 44
tttgctctag gaaccctcag cccc                                          24

<210> SEQ ID NO 45
<211> LENGTH: 24
<212> TYPE: DNA
<213> ORGANISM: Artificial
<220> FEATURE:
<223> OTHER INFORMATION: Cpf1 crRNA NPY1R_P_1 guide

<400> SEQUENCE: 45
tttcaagcct cgggaaactg ccct                                          24

<210> SEQ ID NO 46
<211> LENGTH: 24
<212> TYPE: DNA
<213> ORGANISM: Artificial
<220> FEATURE:
<223> OTHER INFORMATION: Cpf1 crRNA NPY1R_P_2 guide

<400> SEQUENCE: 46
```
tttctttgtt tgcaggtcag tgcc                                           24

<210> SEQ ID NO 47
<211> LENGTH: 24
<212> TYPE: DNA
<213> ORGANISM: Artificial
<220> FEATURE:
<223> OTHER INFORMATION: Cpf1 crRNA NPY1R_P_3 guide

<400> SEQUENCE: 47
tttgggctgg cgctcgagct ctcc                                           24

<210> SEQ ID NO 48
<211> LENGTH: 3822
<212> TYPE: DNA
<213> ORGANISM: Artificial
<220> FEATURE:
<223> OTHER INFORMATION: Human codon optimized dLbCpf1

<400> SEQUENCE: 48
atgagcaagc tggagaagtt tacaaactgc tactccctgt ctaagaccct gaggttcaag      60
gccatccctg tgggcaagac ccaggagaac atcgacaata gcggctgct ggtggaggac      120 gagaagagag ccgaggatta aagggcgtg aagaagctgc tggatcgcta ctatctgtct      180
tttatcaacg acgtgctgca cagcatcaag ctgaagaatc tgaacaatta catcagcctg      240
ttccggaaga aaccagaac cgagaaggag aataaggagc tggagaacct ggagatcaat      300
ctgcggaagg agatcgccaa ggccttcaag gcaacgagg gctacaagtc cctgtttaag      360
aaggatatca tcgagacaat cctgccagag ttcctggacg ataaggacga gatcgccctg      420
gtgaacagct tcaatggctt taccacagcc ttcaccggct ctttgataa cagagagaat      480 atgttttccg aggaggccaa gagcacatcc atcgccttca ggtgtatcaa cgagaatctg      540
acccgctaca tctctaatat ggacatcttc gagaaggtgg acgccatctt tgataagcac      600
gaggtgcagg agatcaagga agatcctg aacagcgact atgatgtgga ggatttcttt      660
gagggcgagt tctttaactt tgtgctgaca caggagggca tcgacgtgta acgccatc      720 atcgcgggct tcgtgaccga gagcggcgag aagatcaagg gcctgaacga gtacatcaac      780
ctgtataatc agaaaaccaa gcagaagctg cctaagttta agccactgta taagcaggtg      840
ctgagcgatc gggagtctct gagcttctac ggcgagggc atacatccga tgaggagtg      900 ctggaggtgt tagaaacac cctgaacaag acagcgaga tcttcagctc catcaagaag      960
ctggagaagc tgttcaagaa ttttgacgag tactctagcg ccggcatctt tgtgaagaac      1020
ggccccgcca tcagcacaat ctccaaggat atcttcggcg agtggaacgt gatccgggac      1080
aagtggaatg ccgagtatga cgatatccac ctgaagaaga ggccgtggt gaccgagaag      1140 tacgaggacg atcggagaaa gtccttcaag aagatcggct ccttttctct ggagcagctg      1200
caggagtacg ccgacgccga tctgtctgtg gtggagaagc tgaaggagat catcatccag      1260
aaggtggatg agatctacaa ggtgtatggc tcctctgaga gctgttcga cgccgatttt      1320 gtgctggaga agagcctgaa gaagaacgac gccgtggtgg ccatcatgaa ggacctgctg      1380
gattctgtga gagcttcga gaattacatc aaggccttct tggcgaggg caaggagaca      1440 aacagggacg agtccttcta tggcgatttt gtgctggcct acgacatcct gctgaaggtg      1500
gaccacatct acgatgccat ccgcaattat gtgacccaga agcctactc taaggataag      1560 ttcaagctgt attttcagaa ccctcagttc atgggcggct gggacaagga taaggagaca      1620
gactatcggg ccaccatcct gagatacggc tccaagtact atctggccat catggataag      1680

```
aagtacgcca agtgcctgca gaagatcgac aaggacgatg tgaacggcaa ttacgagaag    1740
atcaactata agctgctgcc cggccctaat aagatgctgc caaaggtgtt ctttttctaag   1800 aagtggatgg cctactataa ccccagcgag gacatccaga agatctacaa gaatggcaca    1860
ttcaagaagg gcgatatgtt taacctgaat gactgtcaca gctgatcga cttctttaag    1920 gatagcatct cccggtatcc aaagtggtcc aatgcctacg atttcaactt ttctgagaca    1980
gagaagtata aggacatcgc cggcttttac agagaggtgg aggagcaggg ctataaggtg    2040
agcttcgagt ctgccagcaa gaaggaggtg gataagctgg tggaggaggg caagctgtat    2100
atgttccaga tctataacaa ggacttttcc gataagtctc acggcacacc caatctgcac    2160
accatgtact tcaagctgct gtttgacgag aacaatcacg acagatcag gctgagcgga    2220 ggagcagagc tgttcatgag gcgcgcctcc ctgaagaagg aggagctggt ggtgcaccca    2280
gccaactccc ctatcgccaa caagaatcca gataatccca gaaaaccac aaccctgtcc    2340 tacgacgtgt ataaggataa gaggttttct gaggaccagt acgagctgca catcccaatc    2400
gccatcaata agtgccccaa gaacatcttc aagatcaata cagaggtgcg cgtgctgctg    2460
aagcacgacg ataaccccta tgtgatcggc atcgccaggg gcgagcgcaa tctgctgtat    2520
atcgtggtgg tggacggcaa gggcaacatc gtggagcagt attccctgaa cgagatcatc    2580
aacaacttca cggcatcag gatcaagaca gattaccact ctctgctgga caagaaggag    2640
aaggagaggt tcgaggcccg ccagaactgg acctccatcg agaatatcaa ggagctgaag    2700
gccggctata tctctcaggt ggtgcacaag atctgcgagc tggtggagaa gtacgatgcc    2760
gtgatcgccc tggaggacct gaactctggc tttaagaata gccgcgtgaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta gtccatgtc tacccagaac ggcttcatct tttacatccc tgcctggctg    3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagacgc cgattacatc    3180
aagaagtgga gctgtactc ctacggcaac cggatcagaa tcttccggaa tcctaagaag    3240
aacaacgtgt tcgactggga ggaggtgtgc ctgaccagcg cctataagga gctgttcaac    3300
aagtacggca tcaattatca gcagggcgat atcagagccc tgctgtgcga gcagtccgac    3360 aaggcctct actctagctt tatggccctg atgagcctga tgctgcagat gcggaacagc    3420
atcacaggcc gcaccgacgt ggattttctg atcagccctg tgaagaactc cgacggcatc    3480
ttctacgata gccggaacta tgaggcccag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcacaaaagg ccggcggcca cgaaaaaggc cggccaggca    3720
aaaaagaaaa agggatccta cccatacgat gttccagatt acgcttatcc ctacgacgtg    3780
cctgattatg cataccata tgatgtcccc gactatgcct aa                       3822
```

<210> SEQ ID NO 49
<211> LENGTH: 1227
<212> TYPE: DNA
<213> ORGANISM: Artificial
<220> FEATURE:

<223> OTHER INFORMATION: BPK1169: CAG-DmrC-NLS-FLAG-P65

<400> SEQUENCE: 49

| | |
|---|---|
| atgggatcca gaatcctctg gcatgagatg tggcatgaag gcctggaaga ggcatctcgt | 60 |
| ttgtactttg gggaaaggaa cgtgaaaggc atgtttgagg tgctggagcc cttgcatgct | 120 |
| atgatggaac ggggacccca gactctgaag gaaacatcct taatcaggc ctatggtcga | 180 |
| gatttaatgg aggcccaaga gtggtgcagg aagtacatga atcagggaa tgtcaaggac | 240 |
| ctcctccaag cctgggacct ctattatcat gtgttccgac gaatctcaaa gggcggcgga | 300 |
| tcccccaaga agaagaggaa agtctcgagc gactacaaag accatgacgg tgattataaa | 360 |
| gatcatgaca tcgattacaa ggatgacgat gacaaggctg caggaggcgg tggaagcggg | 420 |
| atggagttcc agtacctgcc agatacagac gatcgtcacc ggattgagga gaaacgtaaa | 480 |
| aggacatatg agaccttcaa gagcatcatg aagaagagtc ctttcagcgg acccaccgac | 540 |
| ccccggcctc cacctcgacg cattgctgtg ccttcccgca gctcagcttc tgtccccaag | 600 |
| ccagcacccc agccctatcc ctttacgtca tccctgagca ccatcaacta tgatgagttt | 660 |
| cccaccatgg tgtttccttc tgggcagatc agccaggcct cggccttggc cccggcccct | 720 |
| ccccaagtcc tgcccaggc tccagcccct gcccctgctc cagccatggt atcagctctg | 780 |
| gcccaggccc cagcccctgt cccagtccta gccccaggcc ctcctcaggc tgtggcccca | 840 |
| cctgccccca gcccaccca ggctggggaa ggaacgctgt cagaggccct gctgcagctg | 900 |
| cagtttgatg atgaagacct gggggccttg cttggcaaca gcacagaccc agctgtgttc | 960 |
| acagacctgg catccgtcga taactccgag tttcagcagc tgctgaacca gggcatacct | 1020 |
| gtggcccccc acacaactga gcccatgctg atggagtacc ctgaggctat aactcgccta | 1080 |
| gtgacagggg cccagaggcc ccccgaccca gctcctgctc cactgggggc cccggggctc | 1140 |
| cccaatggcc tcctttcagg agatgaagac ttctcctcca ttgcggacat ggacttctca | 1200 |
| gccctgctga gtcagatcag ctcttaa | 1227 |

<210> SEQ ID NO 50
<211> LENGTH: 2016
<212> TYPE: DNA
<213> ORGANISM: Artificial
<220> FEATURE:
<223> OTHER INFORMATION: MMW948: CAG-DmrC-NLS-FLAG-VPR

<400> SEQUENCE: 50

| | |
|---|---|
| atgggatcca gaatcctctg gcatgagatg tggcatgaag gcctggaaga ggcatctcgt | 60 |
| ttgtactttg gggaaaggaa cgtgaaaggc atgtttgagg tgctggagcc cttgcatgct | 120 |
| atgatggaac ggggacccca gactctgaag gaaacatcct taatcaggc ctatggtcga | 180 |
| gatttaatgg aggcccaaga gtggtgcagg aagtacatga atcagggaa tgtcaaggac | 240 |
| ctcctccaag cctgggacct ctattatcat gtgttccgac gaatctcaaa gggcggcgga | 300 |
| tcccccaaga agaagaggaa agtctcgagc gactacaaag accatgacgg tgattataaa | 360 |
| gatcatgaca tcgattacaa ggatgacgat gacaaggctg caggaggcgg tggaagcggg | 420 |
| tcggaggcca gcggttccgg acgggctgac gcattggacg attttgatct ggatatgctg | 480 |
| ggaagtgacg ccctcgatga ttttgacctt gacatgcttg gttcggatgc ccttgatgac | 540 |
| tttgacctcg acatgctcgg cagtgacgcc cttgatgatt tcgacctgga catgctgatt | 600 |
| aactctagaa gttccggatc tccgaaaaag aaacgcaaag ttggtagcca gtacctgccc | 660 |
| gacaccgacg accggcaccg gatcgaggaa aagcggaagc ggacctacga gacattcaag | 720 |

```
agcatcatga agaagtcccc cttcagcggc cccaccgacc ctagacctcc acctagaaga      780
atcgccgtgc ccagcagatc cagcgccagc gtgccaaaac ctgcccccca gccttacccc      840
ttcaccagca gcctgagcac catcaactac gacgagttcc ctaccatggt gttccccagc      900
ggccagatct ctcaggcctc tgctctggct ccagccoctc ctcaggtgct gcctcaggct      960
cctgctcctg caccagctcc agccatggtg tctgcactgg ctcaggcacc agcacccgtg     1020
cctgtgctgg ctcctggacc tccacaggct gtggctccac cagcccctaa acctacacag     1080
gccggcgagg gcacactgtc tgaagctctg ctgcagctgc agttcgacga cgaggatctg     1140
ggagccctgc tgggaaacag caccgatcct gccgtgttca ccgacctggc cagcgtggac     1200
aacagcgagt tccagcagct gctgaaccag gcatccctg tgccccctca ccaccgag       1260 cccatgctga tggaataccc cgaggccatc acccggctcg tgacaggcgc tcagaggcct     1320
cctgatccag ctcctgcccc tctgggagca ccaggcctgc ctaatggact gctgtctggc     1380
gacgaggact tcagctctat cgccgatatg gatttctcag ccttgctggg ctctggcagc     1440
ggcagccggg attccaggga agggatgttt ttgccgaagc ctgaggccgg ctccgctatt     1500
agtgacgtgt ttgagggccg cgaggtgtgc cagccaaaac gaatccggcc atttcatcct     1560
ccaggaagtc catgggccaa ccgcccactc cccgccagcc tcgcaccaac accaaccggt     1620
ccagtacatg agccagtcgg gtcactgacc ccggcaccag tccctcagcc actggatcca     1680
gcgcccgcag tgactcccga ggccagtcac ctgttggagg atcccgatga agagacgagc     1740
caggctgtca aagcccttcg ggagatggcc gatactgtga ttcccagaa ggaagaggct     1800 gcaatctgtg gcaaatgga cctttcccat ccgccccaa ggggccatct ggatgagctg     1860
acaaccacac ttgagtccat gaccgaggat ctgaacctgg actcacccct gaccccggaa     1920
ttgaacgaga ttctggatac cttcctgaac gacgagtgcc tcttgcatgc catgcatatc     1980
agcacaggac tgtccatctt cgacacatct ctgttt                                2016

<210> SEQ ID NO 51
<211> LENGTH: 4632
<212> TYPE: DNA
<213> ORGANISM: Artificial
<220> FEATURE:
<223> OTHER INFORMATION: JG1202: CAG-human dLbCpf1(D832A)-NLS-3xHA-P65

<400> SEQUENCE: 51
atgagcaagc tggagaagtt tacaaactgc tactccctgt ctaagaccct gaggttcaag       60
gccatccctg tgggcaagac ccaggagaac atcgacaata gcggctgct ggtgaggac       120 gagaagagag ccgaggatta aagggcgtg aagaagctgc tggatcgcta ctatctgtct       180
tttatcaacg acgtgctgca cagcatcaag ctgaagaatc tgaacaatta catcagcctg       240
ttccggaaga aaccagaac cgagaaggag ataaggagc tggagaacct ggagatcaat       300
ctgcggaagg agatcgccaa ggccttcaag ggcaacgagg ctacaagtc cctgttaag       360 aaggatatca tcgagacaat cctgccagag ttcctggacg ataaggacga gatcgccctg       420
gtgaacagct tcaatggctt taccacagcc ttcaccggct ctttgataa cagagagaat       480 atgttttccg aggaggccaa gagcacatcc atcgccttca ggtgtatcaa cgagaatctg       540
acccgctaca tctctaatat ggacatcttc gagaaggtgg acgccatctt tgataagcac       600
gaggtgcagg agatcaagga agatctcct aacagcgact atgatgtgga ggatttcttt       660
gagggcgagt tctttaactt tgtgctgaca caggagggca tcgacgtgta taacgccatc       720
```

```
atcggcggct tcgtgaccga gagcggcgag aagatcaagg gcctgaacga gtacatcaac    780
ctgtataatc agaaaaccaa gcagaagctg cctaagttta agccactgta taagcaggtg    840
ctgagcgatc gggagtctct gagcttctac ggcgagggct atacatccga tgaggaggtg    900
ctggaggtgt ttagaaacac cctgaacaag aacagcgaga tcttcagctc catcaagaag    960
ctggagaagc tgttcaagaa ttttgacgag tactctagcg ccggcatctt tgtgaagaac   1020
ggccccgcca tcagcacaat ctccaaggat atcttcggcg agtggaacgt gatccgggac   1080
aagtggaatg ccgagtatga cgatatccac ctgaagaaga aggccgtggt gaccgagaag   1140
tacgaggacg atcggagaaa gtccttcaag aagatcggct ccttttctct ggagcagctg   1200
caggagtacg ccgacgccga tctgtctgtg gtggagaagc tgaaggagat catcatccag   1260
aaggtggatg agatctacaa ggtgtatggc tcctctgaga gctgttcga cgccgatttt   1320 gtgctggaga gagcctgaa gaagaacgac gccgtggtgg ccatcatgaa ggacctgctg   1380
gattctgtga gagcttcga gaattacatc aaggccttct ttggcgaggg caaggagaca   1440
aacagggacg agtccttcta tggcgatttt gtgctggcct acgacatcct gctgaaggtg   1500
gaccacatct acgatgccat ccgcaattat gtgacccaga gccctactc taaggataag   1560 ttcaagctgt attttcagaa ccctcagttc atgggcggct gggacaagga taaggagaca   1620
gactatcggg ccaccatcct gagatacggc tccaagtact atctggccat catggataag   1680
aagtacgcca agtgcctgca gaagatcgac aaggacgatg tgaacggcaa ttacgagaag   1740
atcaactata gctgctgcc cggccctaat aagatgctgc caaaggtgtt ctttctaag   1800 aagtggatgg cctactataa ccccagcgag gacatccaga gatctacaa gaatggcaca   1860 ttcaagaagg gcgatatgtt taacctgaat gactgtcaca agctgatcga cttctttaag   1920
gatagcatct cccggtatcc aaagtggtcc aatgcctacg atttcaactt ttctgagaca   1980
gagaagtata aggacatcgc cggcttttac agagaggtgg aggagcaggg ctataaggtg   2040
agcttcgagt ctgccagcaa gaaggaggtg gataagctgg tggaggaggg caagctgtat   2100
atgttccaga tctataacaa ggacttttcc gataagtctc acggcacacc caatctgcac   2160
accatgtact tcaagctgct gtttgacgag aacaatcacg acagatcag gctgagcgga   2220 ggagcagagc tgttcatgag gcgcgcctcc ctgaagaagg aggagctggt ggtgcaccca   2280
gccaactccc ctatcgccaa caagaatcca gataatccca gaaaaccac aaccctgtcc   2340 tacgacgtgt ataaggataa gaggtttttct gaggaccagt acgagctgca catcccaatc   2400
gccatcaata agtgccccaa gaacatcttc aagatcaata cagaggtgcg cgtgctgctg   2460
aagcacgacg ataacccta tgtgatcggc atcgccaggg gcgagcgcaa tctgctgtat   2520
atcgtggtgg tggacggcaa gggcaacatc gtggagcagt attccctgaa cgagatcatc   2580
aacaacttca acggcatcag gatcaagaca gattaccact ctctgctgga caagaaggag   2640
aaggagaggt tcgaggcccg ccagaactgg acctccatcg agaatatcaa ggagctgaag   2700
gccggctata tctctcaggt ggtgcacaag atctgcgagc tggtggagaa gtacgatgcc   2760
gtgatcgccc tggaggacct gaactctggc tttaagaata gccgcgtgaa ggtggagaag   2820
caggtgtatc agaagttcga gaagatgctg atcgataagc tgaactacat ggtggacaag   2880
aagtctaatc cttgtgcaac aggcggcgcc ctgaagggct atcagatcac caataagttc   2940
gagagcttta gtccatgtc tacccagaac ggcttcatct tttacatccc tgcctggctg   3000
acatccaaga tcgatccatc taccggcttt gtgaacctgc tgaaaccaa gtataccagc   3060 atcgccgatt ccaagaagtt catcagctcc tttgacagga tcatgtacgt gcccgaggag   3120
```

```
gatctgttcg agtttgccct ggactataag aacttctctc gcacagacgc cgattacatc    3180
aagaagtgga agctgtactc ctacggcaac cggatcagaa tcttccggaa tcctaagaag    3240
aacaacgtgt tcgactggga ggaggtgtgc ctgaccagcg cctataagga gctgttcaac    3300
aagtacggca tcaattatca gcagggcgat atcagagccc tgctgtgcga gcagtccgac    3360
aaggccttct actctagctt tatggccctg atgagcctga tgctgcagat gcggaacagc    3420
atcacaggcc gcaccgacgt ggattttctg atcagccctg tgaagaactc cgacggcatc    3480
ttctacgata gccggaacta tgaggcccag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcacaaaagg cggcggcca cgaaaaaggc cggccaggca    3720
aaaaagaaaa agggatccta cccatacgat gttccagatt acgcttatcc ctacgacgtg    3780
cctgattatg cataccccata tgatgtcccc gactatgccg aagcatgga gttccagtac    3840
ctgccagata cagacgatcg tcaccggatt gaggagaaac gtaaaggac atatgagacc    3900
ttcaagagca tcatgaagaa gagtcctttc agcggaccca ccgaccccg gcctccacct    3960
cgacgcattg ctgtgccttc ccgcagctca gcttctgtcc ccaagccagc accccagccc    4020
tatccctttta cgtcatccct gagcaccatc aactatgatg agtttcccac catggtgttt    4080
ccttctgggc agatcagcca ggcctcggcc ttggccccgg cccctcccca gtcctgccc    4140
caggctccag cccctgcccc tgctccagcc atggtatcag ctctggccca ggccccagcc    4200
cctgtcccag tcctagcccc aggccctcct caggctgtgg cccacctgc ccccaagccc    4260
acccaggctg gggaaggaac gctgtcagag gccctgctgc agctgcagtt tgatgatgaa    4320
gacctggggg ccttgcttgg caacagcaca gacccagctg tgttcacaga cctggcatcc    4380
gtcgataact ccgagtttca gcagctgctg aaccagggca tacctgtggc cccccacaca    4440
actgagccca tgctgatgga gtaccctgag gctataactc gcctagtgac aggggcccag    4500
aggcccccg acccagctcc tgctccactg ggggccccgg ggctcccca tggcctcctt    4560
tcaggagatg aagacttctc ctccattgcg gacatggact tctcagccct gctgagtcag    4620
atcagctctt aa                                                        4632
```

<210> SEQ ID NO 52
<211> LENGTH: 5418
<212> TYPE: DNA
<213> ORGANISM: Artificial
<220> FEATURE:
<223> OTHER INFORMATION: JG1211: CAG-human dLbCpf1(D832A)-NLS-3xHA-VPR

<400> SEQUENCE: 52

```
atgagcaagc tggagaagtt tacaaactgc tactccctgt ctaagaccct gaggttcaag      60
gccatccctg tgggcaagac ccaggagaac atcgacaata gcggctgct ggtggaggac     120
gagaagagag ccgaggatta agggcgtg aagaagctgc tggatcgcta ctatctgtct     180
tttatcaacg acgtgctgca cagcatcaag ctgaagaatc tgaacaatta catcagcctg     240
ttccggaaga aaccagaac cgagaaggag aataaggagc tggagaacct ggagatcaat     300
ctgcggaagg agatcgccaa ggccttcaag ggcaacgagg gctacaagtc cctgtttaag     360
aaggatatca tcgagacaat cctgccagag ttcctggacg ataaggacga gatcgccctg     420
gtgaacagct tcaatggctt taccacagcc ttcaccggct ctctttgataa cagagagaat     480
```

```
atgttttccg aggaggccaa gagcacatcc atcgccttca ggtgtatcaa cgagaatctg    540
acccgctaca tctctaatat ggacatcttc gagaaggtgg acgccatctt tgataagcac    600
gaggtgcagg agatcaagga agatcctgaa cagcgact atgatgtgga ggatttcttt     660
gagggcgagt tctttaactt tgtgctgaca caggagggca tcgacgtgta taacgccatc    720
atcggcggct tcgtgaccga gagcggcgag aagatcaagg gcctgaacga gtacatcaac    780
ctgtataatc agaaaaccaa gcagaagctg cctaagttta gccactgta taagcaggtg    840
ctgagcgatc gggagtctct gagcttctac ggcgagggct atacatccga tgaggaggtg    900
ctggaggtgt ttagaaacac cctgaacaag aacagcgaga tcttcagctc catcaagaag    960
ctggagaagc tgttcaagaa ttttgacgag tactctagcg ccggcatctt tgtgaagaac   1020
ggccccgcca tcagcacaat ctccaaggat atcttcggcg agtggaacgt gatccgggac   1080
aagtggaatg ccgagtatga cgatatccac ctgaagaaga aggccgtggt gaccgagaag   1140
tacgaggacg atcggagaaa gtccttcaag aagatcggct ccttttctct ggagcagctg   1200
caggagtacg ccgacgccga tctgtctgtg gtggagaagc tgaaggagat catcatccag   1260
aaggtggatg agatctacaa ggtgtatggc tcctctgaga gctgttcga cgccgatttt   1320
gtgctggaga gagcctgaa gaagaacgac gccgtggtgg ccatcatgaa ggacctgctg   1380
gattctgtga gagcttcga gaattacatc aaggccttct ttggcgaggg caaggagaca   1440
aacagggacg agtccttcta tggcgatttt gtgctggcct acgacatcct gctgaaggtg   1500
gaccacatct acgatgccat ccgcaattat gtgacccaga gccctactc taaggataag   1560
ttcaagctgt attttcagaa ccctcagttc atgggcggct gggacaagga taaggagaca   1620
gactatcggg ccaccatcct gagatacggc tccaagtact atctggccat catggataag   1680
aagtacgcca agtgcctgca gaagatcgac aaggacgatg tgaacggcaa ttacgagaag   1740
atcaactata gctgctgcc cggccctaat aagatgctgc caaggtgtt ctttctaag    1800
aagtggatgg cctactataa ccccagcgag gacatccaga gatctacaa gaatggcaca   1860
ttcaagaagg gcgatatgtt taacctgaat gactgtcaca gctgatcga cttctttaag   1920
gatagcatct cccggtatcc aaagtggtcc aatgcctacg atttcaactt ttctgagaca   1980
gagaagtata aggacatcgc cggctttta cagagaggtgg aggagcaggg ctataaggtg   2040
agcttcgagt ctgccagcaa gaaggaggtg ataagctgg tggaggaggg caagctgtat   2100
atgttccaga tctataacaa ggacttttcc gataagtctc acggcacacc caatctgcac   2160
accatgtact tcaagctgct gtttgacgag aacaatcacg acagatcag gctgagcgga   2220
ggagcagagc tgttcatgag gcgcgcctcc ctgaagaagg aggagctggt ggtgcaccca   2280
gccaactccc ctatcgccaa caagaatcca gataatccca gaaaaccac aaccctgtcc   2340
tacgacgtgt ataaggataa gaggttttct gaggaccagt acgagctgca catcccaatc   2400
gccatcaata agtgccccaa gaacatcttc aagatcaata cagaggtgcg cgtgctgctg   2460
aagcacgacg ataaccccta tgtgatcggc atcgccaggg gcgagcgcaa tctgctgtat   2520
atcgtggtgg tggacggcaa gggcaacatc gtggagcagt attccctgaa cgagatcatc   2580
aacaacttca acggcatcag gatcaagaca gattaccact ctctgctgga caagaaggag   2640
aaggagaggt tcgaggcccg ccagaactgg acctccatcg agaatatcaa ggagctgaag   2700
gccggctata tctctcaggt ggtgcacaag atctgcgagc tggtggagaa gtacgatgcc   2760
gtgatcgccc tggaggacct gaactctggc tttaagaata gccgcgtgaa ggtggagaag   2820
caggtgtatc agaagttcga gaagatgctg atcgataagc tgaactacat ggtggacaag   2880
```

-continued

```
aagtctaatc cttgtgcaac aggcggcgcc ctgaagggct atcagatcac caataagttc   2940
gagagcttta agtccatgtc tacccagaac ggcttcatct tttacatccc tgcctggctg   3000
acatccaaga tcgatccatc taccggcttt gtgaacctgc tgaaaaccaa gtataccagc   3060
atcgccgatt ccaagaagtt catcagctcc tttgacagga tcatgtacgt gcccgaggag   3120
gatctgttcg agtttgccct ggactataag aacttctctc gcacagacgc cgattacatc   3180
aagaagtgga agctgtactc ctacggcaac cggatcagaa tcttccggaa tcctaagaag   3240
aacaacgtgt tcgactggga ggaggtgtgc ctgaccagcg cctataagga gctgttcaac   3300
aagtacggca tcaattatca gcagggcgat atcagagccc tgctgtgcga gcagtccgac   3360
aaggccttct actctagctt tatggccctg atgagcctga tgctgcagat gcggaacagc   3420
atcacaggcc gcaccgacgt ggattttctg atcagccctg tgaagaactc cgacggcatc   3480
ttctacgata gccggaacta tgaggcccag gagaatgcca tcctgccaaa gaacgccgac   3540
gccaatggcg cctataacat cgccagaaag gtgctgtggg ccatcggcca gttcaagaag   3600
gccgaggacg agaagctgga taaggtgaag atcgccatct ctaacaagga gtggctggag   3660
tacgcccaga ccagcgtgaa gcacaaaagg ccggcggcca cgaaaaaggc cggcaggca   3720 aaaaagaaaa agggatccta cccatacgat gttccagatt acgcttatcc ctacgacgtg   3780
cctgattatg catacccata tgatgtcccc gactatgccg gaagcgaggc cagcggttcc   3840
ggacgggctg acgcattgga cgattttgat ctggatatgc tgggaagtga cgccctcgat   3900
gattttgacc ttgacatgct tggttcggat gcccttgatg actttgacct cgacatgctc   3960
ggcagtgacg cccttgatga tttcgacctg gacatgctga ttaactctag aagttccgga   4020
tctccgaaaa agaaacgcaa agttggtagc cagtacctgc ccgacaccga cgaccggcac   4080
cggatcgagg aaaagcggaa gcggacctac gagacattca gagcatcat gaagaagtcc   4140 cccttcagcg gccccaccga ccctagacct ccacctagaa gaatcgccgt gcccagcaga   4200
tccagcgcca gcgtgccaaa acctgccccc cagccttacc ccttcaccag cagcctgagc   4260
accatcaact acgacgagtt ccctaccatg gtgttcccca gcggccagat ctctcaggcc   4320
tctgctctgg ctccagcccc tcctcaggtg ctgcctcagg ctcctgctcc tgcaccagct   4380
ccagccatgg tgtctgcact ggctcaggca ccagcacccg tgcctgtgct ggctcctgga   4440
cctccacagg ctgtggctcc accagcccct aaacctacac aggccggcga gggcacactg   4500
tctgaagctc tgctgcagct gcagttcgac gacgaggatc tgggagccct gctgggaaac   4560
agcaccgatc ctgccgtgtt caccgacctg gccagcgtgg acaacagcga gttccagcag   4620
ctgctgaacc agggcatccc tgtggccccc cacaccaccg agcccatgct gatggaatac   4680
cccgaggcca tcacccggct cgtgacaggc gctcagagga ctcctgatcc agctcctgcc   4740
cctctgggag caccaggcct gcctaatgga ctgctgtctg gcgacgagga cttcagctct   4800
atcgccgata tggatttctc agccttgctg ggctctggca gcggcagccg ggattccagg   4860
gaagggatgt ttttgccgaa gcctgaggcc ggctccgcta ttagtgacgt gtttgagggc   4920
cgcgaggtgt gccagccaaa acgaatccgg ccatttcatc ctccaggaag tccatgggcc   4980
aaccgcccac tccccgccag cctcgcacca acaccaaccg gtccagtaca tgagccagtc   5040
gggtcactga ccccggcacc agtccctcag ccactggatc cagcgcccgc agtgactccc   5100
gaggccagtc acctgttgga ggatcccgat gaagagacga gccaggctgt caaagccctt   5160
cgggagatgg ccgatactgt gattccccag aaggaagagg ctgcaatctg tggccaaatg   5220
```

```
gacctttccc atccgccccc aagggggccat ctggatgagc tgacaaccac acttgagtcc    5280
atgaccgagg atctgaacct ggactcaccc ctgaccccgg aattgaacga gattctggat    5340
accttcctga cgacgagtg cctcttgcat gccatgcata tcagcacagg actgtccatc    5400
ttcgacacat ctctgttt                                                   5418

<210> SEQ ID NO 53
<211> LENGTH: 4245
<212> TYPE: DNA
<213> ORGANISM: Artificial
<220> FEATURE:
<223> OTHER INFORMATION: JG674: CAG-human dLbCpf1(D832A)-NLS-3xHA-
      DmrA(X1)

<400> SEQUENCE: 53
atgagcaagc tggagaagtt tacaaactgc tactccctgt ctaagaccct gaggttcaag      60
gccatccctg tgggcaagac ccaggagaac atcgacaata gcggctgct ggtggaggac     120 gagaagagag ccgaggatta aagggcgtg aagaagctgc tggatcgcta ctatctgtct     180
tttatcaacg acgtgctgca cagcatcaag ctgaagaatc tgaacaatta catcagcctg     240
ttccggaaga aaaccagaac cgagaaggag aataaggagc tggagaacct ggagatcaat     300
ctgcggaagg agatcgccaa ggccttcaag ggcaacgagg ctacaagtc cctgtttaag     360 aaggatatca tcgagacaat cctgccagag ttcctggacg ataaggacga gatcgccctg     420
gtgaacagct tcaatggctt taccacagcc ttcaccggct tctttgataa cagagagaat     480
atgttttccg aggaggccaa gagcacatcc atcgccttca ggtgtatcaa cgagaatctg     540
acccgctaca tctctaatat ggacatcttc gagaaggtga cgccatctt tgataagcac     600 gaggtgcagg agatcaagga gagatcctg aacagcgact atgatgtgga ggatttcttt     660
gagggcgagt tctttaactt tgtgctgaca caggagggca tcgacgtgta taacgccatc     720
atcggcggct tcgtgaccga gagcggcgag aagatcaagg gcctgaacga gtacatcaac     780
ctgtataatc agaaaaccaa gcagaagctg cctaagttta gccactgta taagcaggtg     840 ctgagcgatc gggagtctct gagcttctac ggcgagggct atacatccga tgaggaggtg     900
ctggaggtgt ttagaaacac cctgaacaag aacagcgaga tcttcagctc catcaagaag     960
ctggagaagc tgttcaagaa ttttgacgag tactctagcg ccggcatctt tgtgaagaac    1020 ggcccccgcca tcagcacaat ctccaaggat atcttcggcg agtggaacgt gatccggac    1080 aagtggaatg ccgagtatga cgatatccac ctgaagaaga ggccgtggt gaccgagaag    1140 tacgaggacg atcggagaaa gtccttcaag aagatcggct ccttttctct ggagcagctg    1200
caggagtacg ccgacgccga tctgtctgtg gtggagaagc tgaaggagat catcatccag    1260 aagtggatg agatctacaa ggtgtatggc tcctctgaga gctgttcga cgccgatttt    1320 gtgctggaga gagcctgaa gaagaacgac gccgtggtgg ccatcatgaa ggacctgctg    1380
gattctgtga gagcttcga gaattacatc aaggccttct ttggcgaggg caaggagaca    1440
aacagggacg agtccttcta tggcgatttt gtgctggcct acgacatcct gctgaaggtg    1500
gaccacatct acgatgccat ccgcaattat gtgacccaga gccctactc taaggataag    1560 ttcaagctgt attttcagaa ccctcagttc atgggcggct gggacaagga taggagaca    1620 gactatcggg ccaccatcct gagatacggc tccaagtact atctggccat catggataag    1680
aagtacgcca gtgcctgca gaagatcgac aaggacgatg tgaacggcaa ttacgagaag    1740
atcaactata gctgctgcc cggccctaat aagatgctgc caaaggtgtt cttttctaag    1800
```

-continued

```
aagtggatgg cctactataa ccccagcgag gacatccaga agatctacaa gaatggcaca   1860
ttcaagaagg gcgatatgtt taacctgaat gactgtcaca agctgatcga cttctttaag   1920
gatagcatct cccggtatcc aaagtggtcc aatgcctacg atttcaactt ttctgagaca   1980
gagaagtata aggacatcgc cggcttttac agagaggtgg aggagcaggg ctataaggtg   2040
agcttcgagt ctgccagcaa gaaggaggtg gataagctgg tggaggaggg caagctgtat   2100
atgttccaga tctataacaa ggacttttcc gataagtctc acggcacacc caatctgcac   2160
accatgtact tcaagctgct gtttgacgag aacaatcacg acagatcag gctgagcgga   2220 ggagcagagc tgttcatgag gcgcgcctcc ctgaagaagg aggagctggt ggtgcaccca   2280
gccaactccc ctatcgccaa caagaatcca gataatccca agaaaaccac aaccctgtcc   2340
tacgacgtgt ataaggataa gaggttttct gaggaccagt acgagctgca catcccaatc   2400
gccatcaata agtgccccaa gaacatcttc aagatcaata cagaggtgcg cgtgctgctg   2460
aagcacgacg ataaccccta tgtgatcggc atcgccaggg gcgagcgcaa tctgctgtat   2520
atcgtggtgg tggacggcaa gggcaacatc gtggagcagt attccctgaa cgagatcatc   2580
aacaacttca acggcatcag gatcaagaca gattaccact ctctgctgga caagaaggag   2640
aaggagaggt tcgaggcccg ccagaactgg acctccatcg agaatatcaa ggagctgaag   2700
gccggctata tctctcaggt ggtgcacaag atctgcgagc tggtggagaa gtacgatgcc   2760
gtgatcgccc tggaggacct gaactctggc tttaagaata gccgcgtgaa ggtggagaag   2820
caggtgtatc agaagttcga gaagatgctg atcgataagc tgaactacat ggtggacaag   2880
aagtctaatc cttgtgcaac aggcggcgcc ctgaagggct atcagatcac caataagttc   2940
gagagcttta gtccatgtc tacccagaac ggcttcatct tttacatccc tgcctggctg   3000
acatccaaga tcgatccatc taccggcttt gtgaacctgc tgaaaaccaa gtataccagc   3060
atcgccgatt ccaagaagtt catcagctcc tttgacagga tcatgtacgt gcccgaggag   3120
gatctgttcg agtttgccct ggactataag aacttctctc gcacagacgc cgattacatc   3180
aagaagtgga agctgtactc ctacggcaac cggatcagaa tcttccggaa tcctaagaag   3240
aacaacgtgt tcgactggga ggaggtgtgc ctgaccagcg cctataagga gctgttcaac   3300
aagtacggca tcaattatca gcagggcgat atcagagccc tgctgtgcga gcagtccgac   3360 aaggcccttct actctagctt tatggcccctg atgagcctga tgctgcagat gcggaacagc   3420
atcacaggcc gcaccgacgt ggatttctg atcagccctg tgaagaactc cgacggcatc   3480
ttctacgata gccggaacta tgaggcccag gagaatgcca tcctgccaaa gaacgccgac   3540
gccaatggcg cctataacat cgccagaaag gtgctgtggg ccatcggcca gttcaagaag   3600
gccgaggacg agaagctgga taaggtgaag atcgccatct ctaacaagga gtggctggag   3660
tacgcccaga ccagcgtgaa gcacaaaagg ccggcggcca cgaaaaaggc cggccaggca   3720
aaaaagaaaa agggatccta cccatacgat gttccagatt acgcttatcc ctacgacgtg   3780
cctgattatg cataccccta tgatgtcccc gactatgcct cgagcgacta caaagaccat   3840
gacggtgatt ataaagatca tgacatcgat tacaaggatg acgatgacaa ggctgcagga   3900
ggcggtggaa gcgggagggg agtgcaggtg gaaaccatct ccccaggaga cgggcgcacc   3960
ttccccaagc gcggccagac ctgcgtggtg cactacaccg gatgcttga agatggaaag   4020 aaattgattt ctcccggga cagaaacaag ccctttaagt ttatgctagg caagcaggag   4080
gtgatccgag gctgggaaga aggggttgcc cagatgagtg tgggtcagag agccaaactg   4140
actatatctc cagattatgc ctatggtgcc actgggcacc caggcatcat cccaccacat   4200
```

```
gccactctcg tcttcgatgt ggagcttcta aaactggaag gataa              4245
```

<210> SEQ ID NO 54
<211> LENGTH: 4575
<212> TYPE: DNA
<213> ORGANISM: Artificial
<220> FEATURE:
<223> OTHER INFORMATION: JG676: CAG-human dLbCpf1(D832A)-NLS-3xHA-
      DmrA(X2)

<400> SEQUENCE: 54

```
atgagcaagc tggagaagtt tacaaactgc tactccctgt ctaagaccct gaggttcaag     60
gccatccctg tgggcaagac ccaggagaac atcgacaata gcggctgct ggtggaggac     120 gagaagagag ccgaggatta aagggcgtg aagaagctgc tggatcgcta ctatctgtct    180
tttatcaacg acgtgctgca cagcatcaag ctgaagaatc tgaacaatta catcagcctg    240
ttccggaaga aaaccagaac cgagaaggag aataaggagc tggagaaccct ggagatcaat    300 ctgcggaagg agatcgccaa ggccttcaag ggcaacgagg ctacaagtc cctgttttaag   360 aaggatatca tcgagacaat cctgccagag ttcctggacg ataaggacga gatcgccctg    420
gtgaacagct tcaatggctt taccacagcc ttcaccggct tctttgataa cagagagaat    480
atgttttccg aggaggccaa gagcacatcc atcgccttca ggtgtatcaa cgagaatctg    540
acccgctaca tctctaatat ggacatcttc gagaaggtgg acgccatctt tgataagcac    600
gaggtgcagg agatcaagga aagatcctg aacagcgact atgatgtgga ggatttctt    660 gagggcgagt tctttaactt tgtgctgaca caggagggca tcgacgtgta taacgccatc    720
atcggcggct tcgtgaccga gagcggcgag aagatcaagg gcctgaacga gtacatcaac    780
ctgtataatc agaaaaccaa gcagaagctg cctaagttta gccactgta taagcaggtg    840 ctgagcgatc gggagtctct gagcttctac ggcgagggct atacatccga tgaggaggtg    900
ctggaggtgt tagaaacac cctgaacaag aacagcgaga tcttcagctc catcaagaag    960
ctggagaagc tgttcaagaa ttttgacgag tactctagcg ccggcatctt tgtgaagaac    1020
ggccccgcca tcagcacaat ctccaaggat atcttcggcg agtggaacgt gatccgggac    1080
aagtggaatg ccgagtatga cgatatccac ctgaagaaga aggccgtggt gaccgagaag    1140
tacgaggacg atcggagaaa gtccttcaag aagatcggcc ctttctctct ggagcagctg    1200
caggagtacg ccgacgccga tctgtctgtg gtggagaagc tgaaggagat catcatccag    1260
aagtggatga gatctacaa ggtgtatggc tcctctgaga gctgttcga cgccgatttt    1320 gtgctggaga gagcctgaa gaagaacgac gccgtggtgg ccatcatgaa ggacctgctg    1380
gattctgtga gagcttcga gaattacatc aaggccttct ttggcgaggg caaggagaca    1440
aacagggacg agtccttcta tggcgatttt gtgctggcct acgacatcct gctgaaggtg    1500
gaccacatct acgatgccat ccgcaattat gtgacccaga gccctactc taaggataag    1560 ttcaagctgt attttcagaa ccctcagttc atgggcggt gggacaagga taggagaca    1620 gactatcggg ccaccatcct gagatacggc tccaagtact atctggccat catggataag    1680
aagtacgcca gtgcctgca gaagatcgac aaggacgatg tgaacggcaa ttacgagaag    1740
atcaactata gctgctgcc cggccctaat aagatgctgc caaggtgttt cttttctaag    1800
aagtggatgg cctactataa ccccagcgag gacatccaga gatctacaa gaatggcaca    1860 ttcaagaagg gcgatatgtt taacctgaat gactgtcaca gctgatcga cttctttaag    1920 gatagcatct cccggtatcc aaagtggtcc aatgcctacg atttcaactt ttctgagaca    1980
```

| | |
|---|---|
| gagaagtata aggacatcgc cggcttttac agagaggtgg aggagcaggg ctataaggtg | 2040 |
| agcttcgagt ctgccagcaa gaaggaggtg ataagctgg tggaggaggg caagctgtat | 2100 |
| atgttccaga tctataacaa ggacttttcc gataagtctc acggcacacc caatctgcac | 2160 |
| accatgtact tcaagctgct gtttgacgag aacaatcacg gacagatcag gctgagcgga | 2220 |
| ggagcagagc tgttcatgag gcgcgcctcc ctgaagaagg aggagctggt ggtgcaccca | 2280 |
| gccaactccc ctatcgccaa caagaatcca gataatccca agaaaaccac aaccctgtcc | 2340 |
| tacgacgtgt ataaggataa gaggttttct gaggaccagt acgagctgca catcccaatc | 2400 |
| gccatcaata agtgccccaa gaacatcttc aagatcaata cagaggtgcg cgtgctgctg | 2460 |
| aagcacgacg ataacccta tgtgatcggc atcgccaggg gcgagcgcaa tctgctgtat | 2520 |
| atcgtggtgg tggacggcaa gggcaacatc gtggagcagt attccctgaa cgagatcatc | 2580 |
| aacaacttca acggcatcag gatcaagaca gattaccact ctctgctgga caagaaggag | 2640 |
| aaggagaggt cgaggcccg ccagaactgg acctccatcg agaatatcaa ggagctgaag | 2700 |
| gccggctata tctctcaggt ggtgcacaag atctgcgagc tggtggagaa gtacgatgcc | 2760 |
| gtgatcgccc tggaggacct gaactctggc tttaagaata gccgcgtgaa ggtggagaag | 2820 |
| caggtgtatc agaagttcga gaagatgctg atcgataagc tgaactacat ggtggacaag | 2880 |
| aagtctaatc cttgtgcaac aggcggcgcc ctgaagggct atcagatcac caataagttc | 2940 |
| gagagcttta gtccatgtc tacccagaac ggcttcatct tttacatccc tgcctggctg | 3000 |
| acatccaaga tcgatccatc taccggcttt gtgaacctgc tgaaaaccaa gtataccagc | 3060 |
| atcgccgatt ccaagaagtt catcagctcc tttgacagga tcatgtacgt gcccgaggag | 3120 |
| gatctgttcg agtttgccct ggactataag aacttctctc gcacagacgc cgattacatc | 3180 |
| aagaagtgga agctgtactc ctacggcaac cggatcagaa tcttccggaa tcctaagaag | 3240 |
| aacaacgtgt tcgactggga ggaggtgtgc ctgaccagcg cctataagga gctgttcaac | 3300 |
| aagtacggca tcaattatca gcagggcgat atcagagccc tgctgtgcga gcagtccgac | 3360 |
| aaggccttct actctagctt tatggccctg atgagcctga tgctgcagat gcggaacagc | 3420 |
| atcacaggcc gcaccgacgt ggattttctg atcagccctg tgaagaactc cgacggcatc | 3480 |
| ttctacgata gccggaacta tgaggcccag gagaatgcca tcctgccaaa gaacgccgac | 3540 |
| gccaatggcg cctataacat cgccagaaag gtgctgtggg ccatcggcca gttcaagaag | 3600 |
| gccgaggacg agaagctgga taaggtgaag atcgccatct ctaacaagga gtggctggag | 3660 |
| tacgcccaga ccagcgtgaa gcacaaaagg ccggcggcca cgaaaaaggc cggccaggca | 3720 |
| aaaaagaaaa agggatccta cccatacgat gttccagatt acgcttatcc ctacgacgtg | 3780 |
| cctgattatg catacccata tgatgtcccc gactatgcct cgagcgacta caaagaccat | 3840 |
| gacggtgatt ataaagatca tgacatcgat tacaaggatg acgatgacaa ggctgcagga | 3900 |
| ggcggtggaa gcgggagggg agtgcaggtg gaaaccatct ccccaggaga cgggcgcacc | 3960 |
| ttccccaagc gcggccagac ctgcgtggtg cactacaccg gatgcttga agatggaaag | 4020 |
| aaatttgatt cctcccggga cagaaacaag ccctttaagt ttatgctagg caagcaggag | 4080 |
| gtgatccgag ctgggaaga aggggttgcc cagatgagtg tgggtcagag agccaaactg | 4140 |
| actatatctc cagattatgc ctatggtgcc actgggcacc caggcatcat cccaccacat | 4200 |
| gccactctcg tcttcgatgt ggagcttcta aaactggaag gttctagggg agtgcaggtg | 4260 |
| gaaaccatct ccccaggaga cgggcgcacc ttccccaagc gcggccagac ctgcgtggtg | 4320 |

| | |
|---|---:|
| cactacaccg gatgcttga agatggaaag aaatttgatt cctcccggga cagaaacaag | 4380 |
| cccttttaagt ttatgctagg caagcaggag gtgatccgag gctgggaaga aggggttgcc | 4440 |
| cagatgagtg tgggtcagag agccaaactg actatatctc cagattatgc ctatggtgcc | 4500 |
| actgggcacc caggcatcat cccaccacat gccactctcg tcttcgatgt ggagcttcta | 4560 |
| aaaactggaag gataa | 4575 |

<210> SEQ ID NO 55
<211> LENGTH: 4917
<212> TYPE: DNA
<213> ORGANISM: Artificial
<220> FEATURE:
<223> OTHER INFORMATION: JG693: CAG-human dLbCpf1(D832A)-NLS-3xHA-DmrA(X3)

<400> SEQUENCE: 55

| | |
|---|---:|
| atgagcaagc tggagaagtt tacaaactgc tactccctgt ctaagaccct gaggttcaag | 60 |
| gccatccctg tgggcaagac ccaggagaac atcgacaata gcggctgct ggtggaggac | 120 |
| gagaagagag ccgaggatta agggcgtg aagaagctgc tggatcgcta ctatctgtct | 180 |
| tttatcaacg acgtgctgca cagcatcaag ctgaagaatc tgaacaatta catcagcctg | 240 |
| ttccggaaga aaccagaac cgagaaggag aataaggagc tggagaaccct ggagatcaat | 300 |
| ctgcggaagg agatcgccaa ggccttcaag ggcaacgagg gctacaagtc cctgtttaag | 360 |
| aaggatatca tcgagacaat cctgccagag ttcctggacg ataaggacga gatcgccctg | 420 |
| gtgaacagct tcaatggctt taccacagcc ttcaccggct tctttgataa cagagagaat | 480 |
| atgttttccg aggaggccaa gagcacatcc atcgccttca ggtgtatcaa cgagaatctg | 540 |
| acccgctaca tctctaatat ggacatcttc gagaaggtgg acgccatctt tgataagcac | 600 |
| gaggtgcagg agatcaagga agatcctg aacagcgact atgatgtgga ggatttcttt | 660 |
| gagggcgagt tctttaactt tgtgctgaca caggagggca tcgacgtgta taacgccatc | 720 |
| atcggcggct tcgtgaccga gagcggcgag aagatcaagg gcctgaacga gtacatcaac | 780 |
| ctgtataatc agaaaaccaa gcagaagctg cctaagttta gccactgta taagcaggtg | 840 |
| ctgagcgatc gggagtctct gagcttctac ggcgagggct atacatccga tgaggaggtg | 900 |
| ctggaggtgt ttagaaacac cctgaacaag aacagcgaga tcttcagctc catcaagaag | 960 |
| ctggagaagc tgttcaagaa ttttgacgag tactctagcg ccggcatctt tgtgaagaac | 1020 |
| ggccccgcca tcagcacaat ctccaaggat atcttcggcg agtggaacgt gatccgggac | 1080 |
| aagtggaatg ccgagtatga cgatatccac ctgaagaaga ggccgtggt gaccgagaag | 1140 |
| tacgaggacg atcggagaaa gtccttcaag aagatcggct ccttttctct ggagcagctg | 1200 |
| caggagtacg ccgacgccga tctgtctgtg gtggagaagc tgaaggagat catcatccag | 1260 |
| aaggtggatg agatctacaa ggtgtatggc tcctctgaga gctgttcga cgccgatttt | 1320 |
| gtgctggaga gagcctgaa gaagaacgac gccgtggtgg ccatcatgaa ggacctgctg | 1380 |
| gattctgtga gagcttcga gaattacatc aaggccttct tggcgaggg caaggagaca | 1440 |
| aacagggacg agtccttcta tggcgatttt gtgctggcct acgacatcct gctgaaggtg | 1500 |
| gaccacatct acgatgccat ccgcaattat gtgacccaga gcccctactc taaggataag | 1560 |
| ttcaagctgt attttcagaa ccctcagttc atgggcggct gggacaagga taaggagaca | 1620 |
| gactatcggg ccaccatcct gagatacggg tccaagtact atctggccat catggataag | 1680 |
| aagtacgcca gtgcctgca gaagatcgac aaggacgatg tgaacggcaa ttacgagaag | 1740 |

```
atcaactata agctgctgcc cggccctaat aagatgctgc caaaggtgtt cttttctaag    1800
aagtggatgg cctactataa ccccagcgag gacatccaga agatctacaa gaatggcaca    1860
ttcaagaagg gcgatatgtt taacctgaat gactgtcaca agctgatcga cttctttaag    1920
gatagcatct cccggtatcc aaagtggtcc aatgcctacg atttcaactt ttctgagaca    1980
gagaagtata aggacatcgc cggcttttac agagaggtgg aggagcaggg ctataaggtg    2040
agcttcgagt ctgccagcaa gaaggaggtg gataagctgg tggaggaggg caagctgtat    2100
atgttccaga tctataacaa ggactttttcc gataagtctc acggcacacc caatctgcac    2160
accatgtact tcaagctgct gtttgacgag aacaatcacg acagatcag gctgagcgga    2220 ggagcagagc tgttcatgag gcgcgcctcc ctgaagaagg aggagctggt ggtgcaccca    2280
gccaactccc ctatcgccaa caagaatcca gataatccca gaaaaccac aaccctgtcc    2340 tacgacgtgt ataaggataa gaggttttct gaggaccagt acgagctgca catcccaatc    2400
gccatcaata agtgccccaa gaacatcttc aagatcaata cagaggtgcg cgtgctgctg    2460
aagcacgacg ataacccta tgtgatcggc atcgccaggg gcgagcgcaa tctgctgtat    2520
atcgtggtgg tggacggcaa gggcaacatc gtggagcagt attccctgaa cgagatcatc    2580
aacaacttca cggcatcag gatcaagaca gattaccact ctctgctgga caagaaggag    2640
aaggagaggt tcgaggcccg ccagaactgg acctccatcg agaatatcaa ggagctgaag    2700
gccggctata tctctcaggt ggtgcacaag atctgcgagc tggtggagaa gtacgatgcc    2760
gtgatcgccc tggaggacct gaactctggc tttaagaata gccgcgtgaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta gtccatgtc tacccagaac ggcttcatct tttacatccc tgcctggctg    3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagacgc cgattacatc    3180
aagaagtgga gctgtactc ctacggcaac cggatcagaa tcttccggaa tcctaagaag    3240
aacaacgtgt tcgactggga ggaggtgtgc ctgaccagcg cctataagga gctgttcaac    3300
aagtacggca tcaattatca gcagggcgat atcagagccc tgctgtgcga gcagtccgac    3360
aaggccttct actctagctt tatggcccctg atgagcctga tgctgcagat gcggaacagc    3420
atcacaggcc gcaccgacgt ggattttctg atcagccctg tgaagaactc cgacggcatc    3480
ttctacgata gccggaacta tgaggcccag agaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcacaaaagg ccggcggcca cgaaaaaggc cggccaggca    3720
aaaaagaaaa agggatccta cccatacgat gttccagatt acgcttatcc ctacgacgtg    3780
cctgattatg catacccata tgatgtcccc gactatgcct cgagcgacta caaagaccat    3840
gacggtgatt ataaagatca tgacatcgat tacaaggatg acgatgacaa ggctgcagga    3900
ggcggtggaa gcgggagggg agtgcaggtg gaaaccatct ccccaggaga cgggcgcacc    3960
ttccccaagc gcggccagac ctgcgtggtg cactacaccg gatgcttga agatggaaag    4020 aaatttgatt cctcccggga cagaaacaag ccctttaagt ttatgctagg caagcaggag    4080
gtgatccgag gctgggaaga aggggttgcc cagatgagtg tgggtcagag agccaaactg    4140
```

```
actatatctc cagattatgc ctatggtgcc actgggcacc caggcatcat cccaccacat    4200
gccactctcg tcttcgatgt ggagcttcta aaactggaag gatctggtgg aagcgggagg    4260
ggagtgcagg tggaaaccat ctccccagga gacgggcgca ccttccccaa gcgcggccag    4320
acctgcgtgg tgcactacac cgggatgctt gaagatggaa agaaatttga ttcctcccgg    4380
gacagaaaca gccctttaa gtttatgcta ggcaagcagg aggtgatccg aggctgggaa     4440
gaaggggttg cccagatgag tgtgggtcag agagccaaac tgactatatc tccagattat    4500
gcctatggtg ccactgggca cccaggcatc atcccaccac atgccactct cgtcttcgat    4560
gtggagcttc taaaactgga aggttctagg ggagtgcagg tggaaaccat ctccccagga    4620
gacgggcgca ccttccccaa gcgcggccag acctgcgtgg tgcactacac cgggatgctt    4680
gaagatggaa agaaatttga ttcctcccgg gacagaaaca gccctttaa gtttatgcta     4740 ggcaagcagg aggtgatccg aggctgggaa gaaggggttg cccagatgag tgtgggtcag    4800
agagccaaac tgactatatc tccagattat gcctatggtg ccactgggca cccaggcatc    4860
atcccaccac atgccactct cgtcttcgat gtggagcttc taaaactgga aggataa       4917
```

<210> SEQ ID NO 56
<211> LENGTH: 5253
<212> TYPE: DNA
<213> ORGANISM: Artificial
<220> FEATURE:
<223> OTHER INFORMATION: YET1000: CAG-human dLbCpf1(D832A)-NLS-3xHA-
      DmrA(X4)

<400> SEQUENCE: 56

```
atgagcaagc tggagaagtt tacaaactgc tactccctgt ctaagaccct gaggttcaag     60
gccatccctg tgggcaagac ccaggagaac atcgacaata gcggctgct ggtggaggac    120 gagaagagag ccgaggatta agggcgtg aagaagctgc tggatcgcta ctatctgtct    180
tttatcaacg acgtgctgca cagcatcaag ctgaagaatc tgaacaatta catcagcctg    240
ttccggaaga aaaccagaac cgagaaggag aataaggagc tggagaacct ggagatcaat    300
ctgcggaagg agatcgccaa ggccttcaag ggcaacgagg gctacaagtc cctgtttaag    360
aaggatatca tcgagacaat cctgccagag ttcctggacg ataaggacga gatcgccctg    420
gtgaacagct tcaatggctt taccacagcc ttcaccggct tctttgataa cagagagaat    480
atgttttccg aggaggccaa gagcacatcc atcgccttca ggtgtatcaa cgagaatctg    540
acccgctaca tctctaatat ggacatcttc gagaaggtgg acgccatctt tgataagcac    600
gaggtgcagg agatcaagga agatctcctg aacagcgact atgatgtgga ggatttcttt    660
gagggcgagt tctttaactt tgtgctgaca caggagggca tcgacgtgta taacgccatc    720
atcggcggct tcgtgaccga gagcggcgag aagatcaagg gcctgaacga gtacatcaac    780
ctgtataatc agaaaaccaa gcagaagctg cctaagttta agccactgta taagcaggtg    840
ctgagcgatc gggagtctct gagcttctac ggcgagggct atacatccga tgaggaggtg    900
ctggaggtgt ttagaaacac cctgaacaag acagcgaga tcttcagctc catcaagaag     960
ctggagaagc tgttcaagaa ttttgacgag tactctagcg ccggcatctt tgtgaagaac    1020
ggccccgcca tcagcacaat ctccaaggat atcttcggcg agtggaacgt gatccgggac    1080
aagtggaatg ccgagtatga cgatatccac ctgaagaaga aggccgtggt gaccgagaag    1140
tacgaggaca tcggagaaaa gtccttcaag aagatcggc cttttctct ggagcagctg     1200 caggagtacg ccgacgccga tctgtctgtg gtggagaagc tgaaggagat catcatccag    1260
```

```
aaggtggatg agatctacaa ggtgtatggc tcctctgaga agctgttcga cgccgatttt   1320
gtgctggaga agagcctgaa gaagaacgac gccgtggtgg ccatcatgaa ggacctgctg   1380
gattctgtga agagcttcga gaattacatc aaggccttct ttggcgaggg caaggagaca   1440
aacagggacg agtccttcta tggcgatttt gtgctggcct acgacatcct gctgaaggtg   1500
gaccacatct acgatgccat ccgcaattat gtgacccaga agccctactc taaggataag   1560
ttcaagctgt attttcagaa ccctcagttc atgggcggct gggacaagga taaggagaca   1620
gactatcggg ccaccatcct gagatacggc tccaagtact atctggccat catggataag   1680
aagtacgcca agtgcctgca agatcgac aaggacgatg tgaacggcaa ttacgagaag   1740
atcaactata agctgctgcc cggccctaat aagatgctgc caaggtgtt cttttctaag   1800 aagtggatgg cctactataa ccccagcgag gacatccaga agatctacaa gaatggcaca   1860
ttcaagaagg gcgatatgtt taacctgaat gactgtcaca agctgatcga cttctttaag   1920
gatagcatct cccggtatcc aaagtggtcc aatgcctacg atttcaactt ttctgagaca   1980
gagaagtata aggacatcgc cggcttttac agagaggtgg aggagcaggg ctataaggtg   2040
agcttcgagt ctgccagcaa gaaggaggtg ataagctgg tggaggaggg caagctgtat   2100
atgttccaga tctataacaa ggacttttcc gataagtctc acggcacacc caatctgcac   2160
accatgtact tcaagctgct gtttgacgag aacaatcacg gacagatcag gctgagcgga   2220
ggagcagagc tgttcatgag gcgcgcctcc ctgaagaagg aggagctggt ggtgcaccca   2280
gccaactccc ctatcgccaa caagaatcca gataatccca gaaaaccac aaccctgtcc   2340 tacgacgtgt ataaggataa gaggtttct gaggaccagt acgagctgca catcccaatc   2400
gccatcaata gtgccccaa gaacatcttc aagatcaata cagaggtgcg cgtgctgctg   2460
aagcacgacg ataacccta tgtgatcggc atcgccaggg gcgagcgcaa tctgctgtat   2520
atcgtggtgg tggacggcaa gggcaacatc gtggagcagt attccctgaa cgagatcatc   2580
aacaacttca cggcatcag gatcaagaca gattaccact ctctgctgga caagaaggag   2640
aaggagaggt tcgaggcccg ccagaactgg acctccatcg agaatatcaa ggagctgaag   2700
gccggctata tctctcaggt ggtgcacaag atctgcgagc tggtggagaa gtacgatgcc   2760
gtgatcgccc tggaggacct gaactctggc tttaagaata gccgcgtgaa ggtggagaag   2820
caggtgtatc agaagttcga gaagatgctg atcgataag tgaactacat ggtggacaag   2880
aagtctaatc cttgtgcaac aggcggcgcc ctgaagggct atcagatcac caataagttc   2940 gagagctta agtccatgtc tacccagaac ggcttcatct tttacatccc tgcctggctg   3000
acatccaaga tcgatccatc taccggcttt gtgaacctgc tgaaaaccaa gtataccagc   3060
atcgccgatt ccaagaagtt catcagctcc tttgacagga tcatgtacgt gcccgaggag   3120
gatctgttcg agtttgccct ggactataag aacttctctc gcacagacgc cgattacatc   3180
aagaagtgga gctgtactc ctacggcaac cggatcagaa tcttccggaa tcctaagaag   3240
aacaacgtgt tcgactggga ggaggtgtgc ctgaccagcg cctataagga gctgttcaac   3300
aagtacggca tcaattatca gcaggcgat atcagagccc tgctgtgcga gcagtccgac   3360
aaggccttct actctagctt tatggccctg atgagcctga ctgctgcagat gcggaacagc   3420 atcacaggcc gcaccgacgt ggattttctg atcagccctg tgaagaactc cgacggcatc   3480
ttctacgata gccggaacta tgaggcccag gagaatgcca tcctgccaaa gaacgccgac   3540
gccaatggcg cctataacat cgccagaaag gtgctgtggg ccatcggcca gttcaagaag   3600
```

```
gccgaggacg agaagctgga taaggtgaag atcgccatct ctaacaagga gtggctggag      3660
tacgcccaga ccagcgtgaa gcacaaaagg ccggcggcca cgaaaaaggc cggccaggca      3720
aaaaagaaaa agggatccta cccatacgat gttccagatt acgcttatcc ctacgacgtg      3780
cctgattatg catacccata tgatgtcccc gactatgcct cgagcgacta caaagaccat      3840
gacggtgatt ataaagatca tgacatcgat tacaaggatg acgatgacaa ggctgcagga      3900
ggcggtggaa gcgggggaag gggagtgcag gtggaaaacca tctcccccagg agacgggcgc      3960 accttcccca gcgcggcca gacctgcgtg gtgcactaca ccgggatgct tgaagatgga      4020
aagaaatttg attcctcccg gacagaaac aagccctta gtttatgct aggcaagcag      4080 gaggtgatcc gaggctggga agaaggggtt gcccagatga gtgtgggtca gagagccaaa      4140
ctgactatat ctccagatta tgcctatggt gccactgggc acccaggcat catcccacca      4200
catgccactc tcgtcttcga tgtggagctt ctaaaactgg aaggttctag gggagtgcag      4260 gtggaaaacca tctcccccagg agacgggcgc accttcccca gcgcggcca gacctgcgtg      4320 gtgcactaca ccgggatgct tgaagatgga aagaaatttg attcctcccg gacagaaac      4380 aagccctta gtttatgct aggcaagcag gaggtgatcc gaggctggga agaaggggtt      4440
gcccagatga gtgtgggtca gagagccaaa ctgactatat ctccagatta tgcctatggt      4500
gccactgggc acccaggcat catcccacca catgccactc tcgtcttcga tgtggagctt      4560
ctaaaactgg aagggggaag cggtggaagc gggaggggga tgcaggtgga aaccatctcc      4620
ccaggagacg ggcgcacctt ccccaagcgc ggccagacct gcgtggtgca ctacaccggg      4680
atgcttgaag atgaaagaa atttgattcc tcccgggaca gaaacaagcc ctttaagttt      4740
atgctaggca agcaggaggt gatccgaggc tgggaagaag gggttgccca gatgagtgtg      4800
ggtcagagag ccaaactgac tatatctcca gattatgcct atggtgccac tgggcaccca      4860
ggcatcatcc caccacatgc cactctcgtc ttcgatgtgg agcttctaaa actggaaggt      4920
tctaggggag tgcaggtgga aaccatctcc ccaggagacg ggcgcacctt ccccaagcgc      4980
ggccagacct gcgtggtgca ctacaccggg atgcttgaag atgaaagaa atttgattcc      5040 tcccgggaca gaaacaagcc ctttaagttt atgctaggca agcaggaggt gatccgaggc      5100
tgggaagaag gggttgccca gatgagtgtg ggtcagagag ccaaactgac tatatctcca      5160
gattatgcct atggtgccac tgggcaccca ggcatcatcc caccacatgc cactctcgtc      5220
ttcgatgtgg agcttctaaa actggaagga taa                                  5253

<210> SEQ ID NO 57
<211> LENGTH: 367
<212> TYPE: DNA
<213> ORGANISM: Artificial
<220> FEATURE:
<223> OTHER INFORMATION: BPK3082: U6-Lb-crRNA-BsmBIcassette

<400> SEQUENCE: 57
tgtacaaaaa agcaggcttt aaaggaacca attcagtcga ctggatccgg taccaaggtc       60
gggcaggaag agggcctatt tcccatgatt ccttcatatt tgcatatacg atacaaggct      120
gttagagaga taattagaat taatttgact gtaaacacaa agatattagt acaaaatacg      180
tgacgtagaa agtaataatt tcttgggtag tttgcagttt taaaattatg ttttaaaatg      240
gactatcata tgcttaccgt aacttgaaag tatttcgatt tcttggcttt atatatcttg      300
tggaaaggac gaaacaccga atttctacta agtgtagatg agacgattaa tgcgtctcc      360 ttttttt                                                               367
```

```
<210> SEQ ID NO 58
<211> LENGTH: 397
<212> TYPE: DNA
<213> ORGANISM: Artificial
<220> FEATURE:
<223> OTHER INFORMATION: crRNAs from Figure 2b

<400> SEQUENCE: 58
gagggcctat ttcccatgat tccttcatat ttgcatatac gatacaaggc tgttagagag      60
ataattagaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg aatttctact aagtgtagat tactgatggt atggggccaa aatttctact     300
aagtgtagat ctctaggaac cctcagcccc aatttctact aagtgtagat aagcctcggg     360
aaactgccct aatttctact aagtgtagat tttttt                                397
```

INDUCIBLE, TUNABLE, AND MULTIPLEX HUMAN GENE REGULATION USING CRISPR-CPF1

CLAIM OF PRIORITY

This application is a national stage application under 35 USC § 371 of International Application No. PCT/US2018/028898, filed Apr. 23, 2018, which claims the benefit of U.S. Patent Application Ser. No. 62/488,585, filed on Apr. 21, 2017. The entire contents of the foregoing are hereby incorporated by reference.

FEDERALLY SPONSORED RESEARCH OR DEVELOPMENT

This invention was made with Government support under Grant Nos. GM107427 and GM118158 awarded by the National Institutes of Health. The Government has certain rights in the invention.

TECHNICAL FIELD

Described herein are drug-inducible, tunable, and multiplexable Cpf1-based activators, and methods of use thereof.

BACKGROUND

RNA-guided CRISPR nucleases have revolutionized both biology and therapeutics with their ease of reprogrammability to recognize target DNA sequences. The widely used Cas9 from *Streptococcus pyogenes* (SpCas9) can be targeted to a specific DNA sequence with an associated complementary guide RNA (gRNA) provided that a protospacer adjacent motif (PAM) of the form NGG is also present.

SUMMARY

The present invention is based, at least in part, on the development of constitutively active and chemically inducible dCpf1-based transcriptional activator platforms, and methods of use thereof, including methods that use multiplex Cpf1 gRNA expression to achieve synergistic or combinatorial activation of endogenous genes in human cells.

Thus, provided herein are fusion proteins that include a catalytically inactive (i.e., catalytically inactive for DNA endonuclease activity) Clustered Regularly Interspaced Short Palindromic Repeats from *Prevotella* and *Francisella* 1 (Cpf1) from Lachnospiraceae bacterium ND2006 protein Cpf1 (dLbCpf1) fused to at least one activation domain (e.g., 1, 2, 3, 4, or more activation domains), preferably wherein the activation domain is a synthetic VPR activator (i.e., comprising four copies of VP16, a human NF-KB p65 activation domain, and an Epstein-Barr virus R transactivator (Rta)). Other activation domains include VP64, Rta, NF-κB p65, and p300, with optional intervening linkers between the Cpf1 and/or each activation domain.

Further, provided herein are fusion proteins that include a catalytically inactive Lachnospiraceae bacterium ND2006 Cpf1 (dLbCpf1) fused to a conditional dimerization domain, with optional intervening linkers between the Cpf1 and/or each activation domain. In some embodiments, the conditional dimerization domain is DmrA or DmrC. These fusion proteins can be provided in compositions or kits that also include a second fusion protein comprising at least one activation domain (e.g., 1, 2, 3, 4, or more activation domains) fused to a second conditional dimerization domain that dimerizes with the conditional dimerization in the fusion protein of claim 2 in the presence of a dimerizing agent, with an optional intervening linker between each of the activation domain(s) and/or the second dimerizing domain. In some embodiments, the conditional dimerization in the fusion protein of claim 2 is DmrA, and the second conditional dimerization domain is DmrC, or (ii) the conditional dimerization in the fusion protein of claim 2 is DmrC, and the second conditional dimerization domain is DmrA. In some embodiments, the activation domain is VP64, Rta, NF-κB p65, VPR, or p300.

Also provided are kits comprising the fusion proteins, and/or nucleic acids encoding a fusion protein as described herein, optionally with the dimerizing agent.

Also provided herein are nucleic acids encoding the fusion proteins described herein, vectors comprising the nucleic acids, and cells comprising the nucleic acids and/or vectors and optionally expressing the fusion proteins.

Further, provided are methods for increasing expression of a target gene in a cell, the method comprising contacting the cell with, or expressing in the cell, one or more of:

(i) a fusion protein that includes a catalytically inactive Lachnospiraceae bacterium ND2006 protein Cpf1 (dLbCpf1) fused to at least one activation domain (e.g., 1, 2, 3, 4, or more activation domains), and at least one crRNA that directs the fusion protein to a regulatory region, e.g., a promoter region, of the target gene; and/or (ii) a first fusion protein that includes a catalytically inactive Lachnospiraceae bacterium ND2006 Cpf1 (dLbCpf1) fused to a conditional dimerization domain, with optional intervening linkers between the Cpf1 and/or each activation domain, and a second fusion protein comprising an activation domain fused to a second conditional dimerization domain that dimerizes with the conditional dimerization in the first fusion protein in the presence of a dimerizing agent (with an optional intervening linker between the activation domain and the second dimerizing domain), and at least one crRNA that directs the fusion protein to a regulatory region, e.g., a promoter region, of the target gene.

Also provided are methods of increasing expression of a plurality of target genes (e.g., two, three, four, or more) in a cell, the method comprising contacting the cell with, or expressing in the cell, one or more of:

(i) a fusion protein that includes a catalytically inactive Lachnospiraceae bacterium ND2006 protein Cpf1 (dLbCpf1) fused to at least one activation domain (e.g., 1, 2, 3, 4, or more activation domains), and at least one nucleic acid encoding a plurality of crRNAs that each direct the fusion protein to a regulatory region, e.g., a promoter region, of one of the target genes;

(ii) a first fusion protein that includes a catalytically inactive Lachnospiraceae bacterium ND2006 Cpf1 (dLbCpf1) fused to a conditional dimerization domain, with optional intervening linkers between the Cpf1 and/or each activation domain, and a second fusion protein comprising an activation domain fused to a second conditional dimerization domain that dimerizes with the conditional dimerization in the first fusion protein in the presence of a dimerizing agent, and at least one nucleic acid encoding a plurality of crRNAs that each direct the fusion protein to a regulatory region, e.g., a promoter region, of one of the target genes.

In some embodiments, the cell is a mammalian cell, e.g., a human cell.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-1E. Targeted human endogenous gene regulation using individual crRNAs with dLbCpf1-based activators (A) Schematic showing direct dLbCpf1-VPR and dLbCpf-p65 activator fusion proteins. (B) Activities of dLbCpf1-p65 or dLbCpf1-VPR using single crRNAs at three endogenous human genes (HBB, AR, and NPY1R) in human HEK293 cells. Relative activation of the indicated gene promoters was measured by RT-qPCR. Three separate individual crRNAs were targeted within promoter sequence 1 kb upstream of the transcription start site for each gene. Relative mRNA expression is calculated by comparison to the control sample in which no crRNA is expressed. (C) Analysis of various crRNAs targeted to the human CD5 and CD22 promoters. 32 crRNAs (16 for each gene) were designed to target sites located within promoter sequences 1 kb upstream or 500 bps downstream of the TSS of each gene. Repetitive sequences were not targeted. After 72 hours post-transfection, cells were stained with fluorescently labeled antibody for CD5 or CD22 protein and fluorescent-positive cells were quantified by flow cytometry. Error bars represent s.e.m. for three biological replicates. Black circles indicate samples that are significantly different (Student t-test, two-tailed test assuming equal variance, p<0.05) compared to controls in which no crRNA was expressed. (D) Schematic illustrating drug-inducible bi-partite dLbCpf1-based activator fusion proteins. dLbCpf1 is fused to one to four DmrA domains and VPR or p65 is fused to a DmrC domain. Because DmrA and DmrC interact only in the presence of an A/C-heterodimerizer drug (red diamond), the bi-partite activator is only reconstituted in the presence of the drug. (E) Activities of drug-inducible bi-partite dLbCpf1-based activators using single crRNAs at three endogenous human genes (HBB, AR, and NPY1R) in human HEK293 cells. Relative activation of the indicated gene promoters was measured by RT-qPCR. The crRNA used for each promoters was the one that showed the highest activity in (B) above. Data shown in (B) and (E) represent three biological independent replicates and error bars indicate standard deviation (SD) of three technical replicates.

FIGS. 2A-2I. Multiplex and synergistic regulation of endogenous human genes by dLbCpf1-based activators (A) Schematic of an expression cassette designed to express multiple gRNAs encoded on a single transcript. The arrows indicate cleavage sites being processed by the RNase activity of dLbCpf1. (B) Schematic illustrating multiplex expression of three crRNAs each targeted to a different endogenous gene promoter in a single cell. (C) Simultaneous activation of three endogenous human genes using crRNAs expressed from a multiplex transcript or from individual transcripts with dLbCpf1-VPR direct fusions (left panel), dLbCpf1-DmrA(×4) and DmrC-VPR fusions (middle panel), and dLbCpf1-DmrA(×4) and DmrC-p65 fusions (right panel). Transcripts were measured in HEK293 cells using RT-qPCR with relative mRNA expression calculated by comparison to the control sample in which no crRNA is expressed. (D) Activities of MST crRNA with different dLbCpf1-based activators in human U2OS cells. Graphs showing activation of three endogenous human genes with dLbCpf1-VPR direct fusions, dLbCpf1-DmrA(×4) and DmrC-p65 fusions, and dLbCpf1-DmrA(×4) and DmrC-VPR fusions and crRNAs expressed from a multiplex single transcript (MST) or from transcripts encoding a single crRNA. RNA expression was measured by RT-qPCR and relative expression shown was calculated by comparison to a control sample in which no crRNA is expressed. (E) Schematic illustrating multiplex expression of three crRNAs each targeted to the same endogenous gene promoter in the same cell. (F) Activities of direct dLbCpf1-p65 or dLbCpf1-VPR fusions with sets of three crRNAs expressed from a multiplex transcript or from individual transcripts on the HBB, AR, or NPY1R endogenous gene promoters. Transcripts were measured in HEK293 cells using RT-qPCR with relative mRNA expression calculated by comparison to the control sample in which no crRNA is expressed. (G) Activities of dLbCpf1-DmrA(×4) and DmrC-VPR fusions or with dLbCpf1-DmrA(×4) and DmrC-p65 fusions with sets of three crRNAs expressed from a multiplex transcript or from individual transcripts on the HBB, AR, or NPY1R endogenous gene promoters. Transcripts were measured in HEK293 cells using RT-qPCR with relative mRNA expression calculated by comparison to the control sample in which no crRNA is expressed. Data shown in (C), (D), (F) and (G) represent three biological independent replicates and error bars indicate standard deviation (SD) of three technical replicates. hU6, human U6 Polymerase III promoter; DR; direct repeat sequence. (H) Inducibility and reversibility of A/C heterodimerizer drug-regulated dLbCpf1-based activators. To measure the kinetics of activator induction, HEK293 cells were transfected with plasmids expressing dLbCpf1-DmrA(×4), DmrC-p65, and MST crRNAs targeting the human HBB or AR promoters. 34 hours after transfection, these cells were split into two cultures: one with media containing A/C heterodimerizer (500 uM) (top, black) and one with media lacking the A/C heterodimerizer (bottom, grey). Cells were collected at various time points and relative mRNA expression levels were measured by RT-qPCR compared to a negative control. (I) To measure the kinetics of reversibility, HEK293 cells were transfected as in (H). 24 hours after transfection, A/C heterodimerzer (500 uM) was added to the medium. 10 hours later, these cells were split into two cultures: one with media containing A/C heterodimerizer (500 uM) (top, blue) and one with media lacking the A/C heterodimerizer (bottom, purple). Cells were collected at various time points and relative mRNA expression levels were measured by RT-qPCR compared to a negative control. Error bars represent s.e.m. of three biological replicates.

DETAILED DESCRIPTION

Figure 1A:
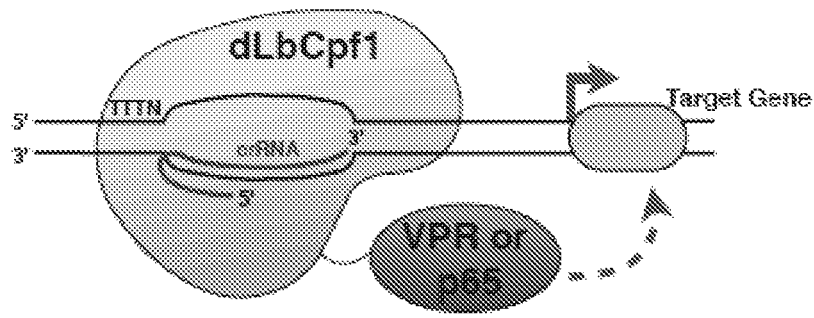

Catalytically inactive forms of SpCas9 ("dead" SpCas9 or dSpCas9) nucleases have been fused with transcriptional activator or repressor domains to alter the expression of genes individually or genome-wide for library screens in mammalian cells[1-4], although efficient activation has required multiple regulatory domains to be recruited to a single promoter[5]. Both small molecule- and light-inducible dCas9-based gene regulatory fusions have also been described, providing additional important capabilities to this platform[6-10]. Recently described CRISPR-Cpf1 nucleases offer important additional capabilities beyond those of SpCas9 including shorter length gRNAs, the capability to target alternative T-rich PAM sequences, and processing of multiple guide RNAs from a single transcript by the Cpf1 nuclease itself[11]. However, to the present inventors' knowledge "dead" Cpf1-based gene regulators have only been used to date to repress gene expression in bacteria[12] and a plant (*Arabidopsis*)[13] and have not been shown to work in mammalian cells or for activating a target gene. Herein we describe constitutively active and chemically inducible dCpf1-based transcriptional activator platforms and show that multiplex Cpf1 gRNA expression can be leveraged to achieve synergistic or combinatorial activation of endogenous genes in human cells.

To our knowledge, the results reported here provide the first demonstrations that RNA-guided Cpf1-based fusions can be used to activate endogenous gene expression in any cell type and the first use of Cpf1-derived gene regulatory proteins in human cells. The orthogonal PAM recognition specificities of LbCpf1 compared with SpCas9 (TTTN versus NGG) open up a new range of targetable sequences for RNA-guided activator proteins. Given the reported higher genome-wide specificities of LbCpf1 compared with SpCas9[14, 15], dLbCpf1 activators may have comparable specificities to dSpCas9 activators, which have been shown by RNA-seq to cause few, if any, off-target gene activation events.

The present work also established drug-inducible dLbCpf1 activators that can be used to control gene regulation in multiple ways. These activators include paired fusion proteins, a first fusion protein that includes a catalytically inactive Lachnospiraceae bacterium ND2006 Cpf1 (dLbCpf1) fused to a conditional dimerization domain, with optional intervening linkers between the Cpf1 and/or each activation domain, and a second fusion protein comprising an activation domain fused to a second conditional dimerization domain that dimerizes with the conditional dimerization in the first fusion protein in the presence of a dimerizing agent, with an optional intervening linker between the activation domain and the second dimerizing domain. The bi-partite nature of these activators enables turning their activity on or off with a cell-permeable A/C dimerizer drug, which provides a useful capability for experimental systems. In addition, the level of activation desired can be tuned by increasing the number of DmrA dimerizer domains fused to dLbCpf1, which presumably leads to recruitment of increasing numbers of DmrC-activator fusions to a given promoter. Changing the activation domain used in the DmrC fusion influenced the extent of activation observed. Somewhat surprisingly and in contrast to previous results with dSpCas9-based activators, the p65 domain (with individual crRNAs) more consistently activated the three gene promoters examined than did the synthetic VPR activator (which contains six strong activation domains). With multiple crRNAs directed to a target promoter, the p65 domain provided stronger activation for the two genes on which synergism was observed. The ability to use the naturally occurring p65 activation domain rather than the synthetic VPR is advantageous as it avoids undesirable side effects (e.g., squelching) caused by very potent activators[16, 17]. Beyond its utility for gene activation, this drug-inducible, multiplex dCpf1-based platform can be used to enable targeted recruitment of other heterologous proteins or functional domains to any endogenous genomic locus of interest.

The present work also demonstrated that a key advantage of the Cpf1 platform, the ability to more simply encode multiple crRNAs on a single transcript, can be leveraged to achieve multiplex activation of endogenous human genes in the same single cell. Multiplex regulation using dSpCas9 gene regulatory proteins is challenging due to substantial recombination between promoters if gRNAs are expressed from separate promoters[18] or the need for additional accessory RNA sequences, promoters, or trans-acting factors if multiple gRNAs are expressed from a single transcript[19-25]. By contrast, the shorter ~40 nt length of crRNAs used by Cpf1 enables two or three crRNAs to be readily encoded on a single oligonucleotide thereby enabling the leveraging of chip-based synthesis to construct precise user-specified combinations of crRNAs targeted to genes of interest; doing the same with dSpCas9 gRNAs is more challenging due to the longer-length (~100 nt) guide RNAs required and the accessory sequences and factors required to enable processing from a single transcript. Thus, these results demonstrate the feasibility of performing methods including multiplex library screens in which the expression of two or more genes are simultaneously regulated, thereby enabling the analysis of more complex cellular phenotypes using this approach.

Cpf1

Clustered, regularly interspaced, short palindromic repeat (CRISPR) systems encode RNA-guided endonucleases that are essential for bacterial adaptive immunity[26]. CRISPR-associated (Cas) nucleases can be readily programmed to cleave target DNA sequences for genome editing in various organisms[27-30]. One class of these nucleases, referred to as Cas9 proteins, complex with two short RNAs: a crRNA and a trans-activating crRNA (tracrRNA)[31, 32]. The most commonly used Cas9 ortholog, SpCas9, uses a crRNA that has 20 nucleotides (nt) at its 5' end that are complementary to the "protospacer" region of the target DNA site. Efficient cleavage also requires that SpCas9 recognizes a protospacer adjacent motif (PAM). The crRNA and tracrRNA are usually combined into a single ~100-nt guide RNA (gRNA)[31, 33-35] that directs the DNA cleavage activity of SpCas9. The genome-wide specificities of SpCas9 nucleases paired with different gRNAs have been characterized using many different approaches[36-39]. SpCas9 variants with substantially improved genome-wide specificities have also been engineered[40, 41].

Recently, a Cas protein named Cpf1 has been identified that can also be programmed to cleave target DNA sequences[42-45]. Unlike SpCas9, Cpf1 requires only a single 42-nt crRNA, which has 23 nt at its 3' end that are complementary to the protospacer of the target DNA sequence[44]. Furthermore, whereas SpCas9 recognizes an NGG PAM sequence that is 3' of the protospacer, AsCpf1 and LbCp1 recognize TTTN PAMs that are found 5' of the protospacer[44]. Early experiments with AsCpf1 and LbCpf1 showed that these nucleases can be programmed to edit target sites in human cells[44] but they were tested on only a small number of sites. On-target activities and genome-wide specificities of both AsCpf1 and LbCpf1 were characterized in Kleinstiver & Tsai et al., Nature Biotechnology 2016.

Provided herein are fusion proteins comprising LbCpf1.
The LbCpf1 wild type protein sequence is as follows:

---

LbCpf1 - Type V CRISPR-associated protein Cpf1 [*Lachnospiraceae bacterium* ND2006], GenBank Acc No. WP_051666128.1

---

```
   1 MLKNVGIDRL DVEKGRKN MS KLEKFTNCYS LSKTLRFKAI PVGKTQENID NKRLLVEDEK

61 RAEDYKGVKK LLDRYYLSFI NDVLHSIKLK NLNNYISLFR KKTRTEKENK ELENLEINLR

121 KEIAKAFKGN EGYKSLFKKD IIETILPEFL DDKDEIALVN SFNGFTTAFT GFFDNRENMF

181 SEEAKSTSIA FRCINENLTR YISNMDIFEK VDAIFDKHEV QEIKEKILNS DYDVEDFFEG

241 EFFNFVLTQE GIDVYNAIIG GFVTESGEKI KGLNEYINLY NQKTKQKLPK FKPLYKQVLS

301 DRESLSFYGE GYTSDEEVLE VFRNTLNKNS EIFSSIKKLE KLFKNFDEYS SAGIFVKNGP

361 AISTISKDIF GEWNVIRDKW NAEYDDIHLK KKAVVTEKYE DDRRKSFKKI GSFSLEQLQE

421 YADADLSVVE KLKEIIIQKV DEIYKVYGSS EKLFDADFVL EKSLKKNDAV VAIMKDLLDS

481 VKSFENYIKA FFGEGKETNR DESFYGDFVL AYDILLKVDH IYDAIRNYVT QKPYSKDKFK

541 LYFQNPQFMG GWDKDKETDY RATILRYGSK YYLAIMDKKY AKCLQKIDKD DVNGNYEKIN

601 YKLLPGPNKM LPKVFFSKKW MAYYNPSEDI QKIYKNGTFK KGDMFNLNDC HKLIDFFKDS

661 ISRYPKWSNA YDFNFSETEK YKDIAGFYRE VEEQGYKVSF ESASKKEVDK LVEEGKLYMF

721 QIYNKDFSDK SHGTPNLHTM YFKLLFDENN HGQIRLSGGA ELFMRRASLK KEELVVHPAN

781 SPIANKNPDN PKKTTTLSYD VYKDKRFSED QYELHIPIAI NKCPKNIFKI NTEVRVLLKH

841 DDNPYVIGID RGERNLLYIV VVDGKGNIVE QYSLNEIINN FNGIRIKTDY HSLLDKKEKE

901 RFEARQNWTS IENIKELKAG YISQVVHKIC ELVEKYDAVI ALEDLNSGFK NSRVKVEKQV

961 YQKFEKMLID KLNYMVDKKS NPCATGGALK GYQITNKFES FKSMSTQNGF IFYIPAWLTS

1021 KIDPSTGFVN LLKTKYTSIA DSKKFISSFD RIMYVPEEDL FEFALDYKNF SRTDADYIKK

1081 WKLYSYGNRI RIFRNPKKNN VFDWEEVCLT SAYKELFNKY GINYQQGDIR ALLCEQSDKA

1141 FYSSFMALMS LMLQMRNSIT GRTDVDFLIS PVKNSDGIFY DSRNYEAQEN AILPKNADAN

1201 GAYNIARKVL WAIGQFKKAE DEKLDKVKIA ISNKEWLEYA QTSVKH
```

Mature LbCpf1 without 18 amino acid signal sequence:

(SEQ ID NO: 2)

MSKLEKFTNCYSLSKTLRFKAIPVGKTQENIDNKRLLVEDEKRAEDYKGVKKLL

DRYYLSFINDVLHSIKLKNLNNYISLFRKKTRTEKENKELENLEINLRKEIAKAFK

GNEGYKSLFKKDIIETILPEFLDDKDEIALVNSFNGFTTAFTGFFDNRENMFSEEA

KSTSIAFRCINENLTRYISNMDIFEKVDAIFDKHEVQEIKEKILNSDYDVEDFFEGE

FFNFVLTQEGIDVYNAIIGGFVTESGEKIKGLNEYINLYNQKTKQKLPKFKPLYKQ

VLSDRESLSFYGEGYTSDEEVLEVFRNTLNKNSEIFSSIKKLEKLFKNFDEYSSAG

IFVKNGPAISTISKDIFGEWNVIRDKWNAEYDDIHLKKKAVVTEKYEDDRRKSFK

KIGSFSLEQLQEYADADLSVVEKLKEIIIQKVDEIYKVYGSSEKLFDADFVLEKSL

KKNDAVVAIMKDLLDSVKSFENYIKAFFGEGKETNRDESFYGDFVLAYDILLKV

DHIYDAIRNYVTQKPYSKDKFKLYFQNPQFMGGWDKDKETDYRATILRYGSKY

YLAIMDKKYAKCLQKIDKDDVNGNYEKINYKLLPGPNKMLPKVFFSKKWMAY

YNPSEDIQKIYKNGTFKKGDMFNLNDCHKLIDFFKDSISRYPKWSNAYDFNFSET

EKYKDIAGFYREVEEQGYKVSFESASKKEVDKLVEEGKLYMFQIYNKDFSDKSH

GTPNLHTMYFKLLFDENNHGQIRLSGGAELFMRRASLKKEELVVHPANSPIANK

NPDNPKKTTTLSYDVYKDKRFSEDQYELHIPIAINKCPKNIFKINTEVRVLLKHD

| LbCpf1 - Type V CRISPR-associated protein Cpf1 [*Lachnospiraceae bacterium* ND2006], GenBank Acc No. WP_051666128.1 |
|---|
| DNPYVIGIDRGERNLLYIVVVDGKGNIVEQYSLNEIINNFNGIRIKTDYHSLLDKK |
| EKERFEARQNWTSIENIKELKAGYISQVVHKICELVEKYDAVIALEDLNSGFKNS |
| RVKVEKQVYQKFEKMLIDKLNYMVDKKSNPCATGGALKGYQITNKFESFKSMS |
| TQNGFIFYIPAWLTSKIDPSTGFVNLLKTKYTSIADSKKFISSFDRIMYVPEEDLFEF |
| ALDYKNFSRTDADYIKKWKLYSYGNRIRIFRNPKKNNVFDWEEVCLTSAYKELF |
| NKYGINYQQGDIRALLCEQSDKAFYSSFMALMSLMLQMRNSITGRTDVDFLISP |
| VKNSDGIFYDSRNYEAQENAILPKNADANGAYNIARKVLWAIGQFKKAEDEKL |
| DKVKIAISNKEWLEYAQTSVKH |

The LbCpf1 variants described herein can include the amino acid sequence of SEQ ID NO:1, e.g., at least comprising amino acids 23-1246 of SEQ ID NO:1, with mutations (i.e., replacement of the native amino acid with a different amino acid, e.g., alanine, glycine, or serine), at one or more of the positions in Table A; amino acids 19-1246 of SEQ ID NO:1 are identical to amino acids 1-1228 of SEQ ID NO:2 (amino acids 1-1246 of SEQ ID NO:1 are referred to herein as LbCPF1 (+18)). In some embodiments, the LbCpf1 variants are at least 80%, e.g., at least 85%, 90%, or 95% identical to the amino acid sequence of SEQ ID NO:2, e.g., have differences at up to 5%, 10%, 15%, or 20% of the residues of SEQ ID NO:2 replaced, e.g., with conservative mutations, in addition to the mutations described herein. In preferred embodiments, the variant retains desired activity of the parent, e.g., the nuclease activity (except where the parent is a nickase or a dead Cpf1), and/or the ability to interact with a guide RNA and target DNA). The version of LbCpf1 used in the present working examples is SEQ ID NO:2, omitting the first 18 amino acids boxed above as described in Zetsche et al. Cell 163, 759-771 (2015).

In some embodiments, the Cpf1 variants also include one of the following mutations listed in Table A, which reduce or destroy the nuclease activity of the Cpf1 (i.e., render them catalytically inactive):

TABLE A

|  | LbCpf1 (+18) | LbCpf1 |
|---|---|---|
| Residues involved in DNA and RNA catalysis | | |
| DNA targeting | D850 | D832 |
|  | E853 | E835 |
|  | N855 | N837 |
|  | Y858 | Y840 |
|  | E943 | E925 |
|  | RH56 | R1138 |
|  | S1158 | S1140 |
|  | D1166 | D1148 |
|  | D1198 | D1180 |
|  | H777 | H759 |
| RNA processing | K786 | K768 |
|  | K803 | K785 |
|  | F807 | F789 |
| Mutations that turn Cpf1 into a nickase | | |
|  | R1156A | R1138A |

See, e.g., Yamano et al., Cell. 2016 May 5; 165(4):949-62; Fonfara et al., Nature. 2016 Apr. 28; 532(7600):517-21; Dong et al., Nature. 2016 Apr. 28; 532(7600):522-6; and Zetsche et al., Cell. 2015 Oct. 22; 163(3):759-71. Note that "LbCpf1 (+18)" refers to the full sequence of amino acids 1-1246 of SEQ ID NO:1, while the LbCpf1 refers to the sequence of LbCpf1 in Zetsche et al., also shown herein as amino acids 1-1228 of SEQ ID NO:2 and amino acids 19-1246 of SEQ ID NO:1. Thus, in some embodiments, for LbCpf1 catalytic activity-destroying mutations are made at D832 and E925, e.g., D832A and E925A.

The Cpf1 variants, preferably comprising one or more nuclease-reducing or killing mutation, can be fused on the N or C terminus of the Cpf1 to a transcriptional activation domain (e.g., a transcriptional activation domain from the VP16 domain form herpes simplex virus (Sadowski et al., 1988, Nature, 335:563-564) or VP64; the p65 domain from the cellular transcription factor NF-kappaB (Ruben et al., 1991, Science, 251:1490-93); a tripartite effector fused to dCas9, composed of activators VP64, p65, and Rta (VPR) linked in tandem, Chavez et al., Nat Methods. 2015 April; 12(4):326-8); or the p300 HAT domain. p300/CBP is a histone acetyltransferase (HAT) whose function is critical for regulating gene expression in mammalian cells. The p300 HAT domain (1284-1673) is catalytically active and can be fused to nucleases for targeted epigenome editing. See Hilton et al., Nat Biotechnol. 2015 May; 33(5):510-7.

Any inducible protein dimerizing system can be used, e.g., based on the FK506-binding protein (FKBP), see, e.g., Rollins et al., Proc Natl Acad Sci USA. 2000 Jun. 20; 97(13): 7096-7101; the iDIMERIZE™ Inducible Heterodimer System from Clontech/Takara, wherein the proteins of interest are fused to the DmrA and DmrC binding domains respectively, and dimerization is induced by adding the A/C Heterodimerizer (AP21967). Others are also known, e.g., FKBP with CyP-Fas and FKCsA dimerizing agent (see Belshaw et al., Proceedings of the National Academy of Sciences of the United States of America. 93 (10): 4604-7 (1996)); FKBP and FRB domain of mTOR with Rapamycin dimerizing agent (Rivera et al., Nature Medicine. 2 (9): 1028-32 (1996)); GyrB domain with coumermycin dimerizing agent (Farrar et al., Nature. 383 (6596): 178-81 (1996)); gibberellin-induced dimerization (see Miyamoto et al., Nature Chemical Biology. 8 (5): 465-70 (2012); Miyamoto et al., Nature Chemical Biology. 8 (5): 465-70 (2012)); and protein heterodimerization system based on small molecules cross-linking fusion proteins derived from HaloTags and SNAP-tags (Erhart et al., Chemistry and Biology. 20 (4): 549-57 (2013).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

In some embodiments, the mutants have alanine in place of the wild type amino acid. In some embodiments, the mutants have any amino acid other than arginine or lysine (or the native amino acid).

Also provided herein are isolated nucleic acids encoding the Cpf1 fusion proteins, vectors comprising the isolated nucleic acids, optionally operably linked to one or more regulatory domains for expressing the variant proteins, and host cells, e.g., mammalian host cells, comprising the nucleic acids, and optionally expressing the variant proteins.

The fusion proteins described herein can be used for altering the genome of a cell; the methods generally include expressing the variant proteins in the cells, along with a guide RNA having a region complementary to a selected portion of the genome of the cell. Methods for selectively altering the genome of a cell are known in the art, see, e.g., U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US20160024529; US20160024524; US20160024523; US20160024510; US20160017366; US20160017301; US20150376652; US20150356239; US20150315576; US20150291965; US20150252358; US20150247150; US20150232883; US20150232882; US20150203872; US20150191744; US20150184139; US20150176064; US20150167000; US20150166969; US20150159175; US20150159174; US20150093473; US20150079681; US20150067922; US20150056629; US20150044772; US20150024500; US20150024499; US20150020223; US20140356867; US20140295557; US20140273235; US20140273226; US20140273037; US20140189896; US20140113376; US20140093941; US20130330778; US20130288251; US20120088676; US20110300538; US20110236530; US20110217739; US20110002889; US20100076057; US20110189776; US20110223638; US20130130248; US20150050699; US20150071899; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; WO/2008/108989; WO/2010/054108; WO/2012/164565; WO/2013/098244; WO/2013/176772; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

The fusion proteins described herein can be used in place of or in addition to any of the Cas9 or Cpf1 proteins described in the foregoing references, or in combination with analogous mutations described therein, with a guide RNA appropriate for the selected Cpf1, i.e., with guide RNAs that target selected sequences.

In addition, the fusion proteins described herein can be used in place of the wild-type Cas9, Cpf1 or other Cas9 or Cpf1 mutations (such as the dCpf1 or Cpf1 nickase) as known in the art, e.g., a fusion protein with a heterologous functional domain as described in U.S. Pat. No. 8,993,233;

US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US 20150071899 and WO 2014/124284.

In some embodiments, the fusion proteins include a linker between the Cpf1 variant and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:3) or GGGGS (SEQ ID NO:4), e.g., two, three, four, or more repeats of the GGGS (SEQ ID NO:3) or GGGGS (SEQ ID NO:4) unit. Other linker sequences can also be used.

In some embodiments, the variant protein includes a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49.

Cell penetrating peptides (CPPs) are short peptides that facilitate the movement of a wide range of biomolecules across the cell membrane into the cytoplasm or other organelles, e.g. the mitochondria and the nucleus. Examples of molecules that can be delivered by CPPs include therapeutic drugs, plasmid DNA, oligonucleotides, siRNA, peptide-nucleic acid (PNA), proteins, peptides, nanoparticles, and liposomes. CPPs are generally 30 amino acids or less, are derived from naturally or non-naturally occurring protein or chimeric sequences, and contain either a high relative abundance of positively charged amino acids, e.g. lysine or arginine, or an alternating pattern of polar and non-polar amino acids. CPPs that are commonly used in the art include Tat (Frankel et al., (1988) Cell. 55:1189-1193, Vives et al., (1997) J. Biol. Chem. 272:16010-16017), penetratin (Derossi et al., (1994) J. Biol. Chem. 269:10444-10450), polyarginine peptide sequences (Wender et al., (2000) Proc. Natl. Acad. Sci. USA 97:13003-13008, Futaki et al., (2001) J. Biol. Chem. 276:5836-5840), and transportan (Pooga et al., (1998) Nat. Biotechnol. 16:857-861).

CPPs can be linked with their cargo through covalent or non-covalent strategies. Methods for covalently joining a CPP and its cargo are known in the art, e.g. chemical cross-linking (Stetsenko et al., (2000) J. Org. Chem. 65:4900-4909, Gait et al. (2003) Cell. Mol. Life. Sci. 60:844-853) or cloning a fusion protein (Nagahara et al., (1998) Nat. Med. 4:1449-1453). Non-covalent coupling between the cargo and short amphipathic CPPs comprising polar and non-polar domains is established through electrostatic and hydrophobic interactions.

CPPs have been utilized in the art to deliver potentially therapeutic biomolecules into cells. Examples include cyclosporine linked to polyarginine for immunosuppression (Rothbard et al., (2000) Nature Medicine 6(11):1253-1257), siRNA against cyclin B1 linked to a CPP called MPG for inhibiting tumorigenesis (Crombez et al., (2007) Biochem Soc. Trans. 35:44-46), tumor suppressor p53 peptides linked to CPPs to reduce cancer cell growth (Takenobu et al., (2002) Mol. Cancer Ther. 1(12):1043-1049, Snyder et al., (2004) PLoS Biol. 2:E36), and dominant negative forms of Ras or phosphoinositol 3 kinase (PI3K) fused to Tat to treat asthma (Myou et al., (2003) J. Immunol. 171:4399-4405).

CPPs have been utilized in the art to transport contrast agents into cells for imaging and biosensing applications. For example, green fluorescent protein (GFP) attached to Tat has been used to label cancer cells (Shokolenko et al., (2005) DNA Repair 4(4):511-518). Tat conjugated to quantum dots have been used to successfully cross the blood-brain barrier for visualization of the rat brain (Santra et al., (2005) Chem. Commun. 3144-3146). CPPs have also been combined with magnetic resonance imaging techniques for cell imaging (Liu et al., (2006) Biochem. and Biophys. Res. Comm. 347(1):133-140). See also Ramsey and Flynn, Pharmacol Ther. 2015 Jul. 22. pii: S0163-7258(15)00141-2.

Alternatively or in addition, the variant proteins can include a nuclear localization sequence, e.g., SV40 large T antigen NLS (PKKKRRV (SEQ ID NO:5)) and nucleoplasmin NLS (KRPAATKKAGQAKKKK (SEQ ID NO:6)). Other NLSs are known in the art; see, e.g., Cokol et al., EMBO Rep. 2000 Nov. 15; 1(5): 411-415; Freitas and Cunha, Curr Genomics. 2009 December; 10(8): 550-557.

In some embodiments, the variants include a moiety that has a high affinity for a ligand, for example GST, FLAG or hexahistidine sequences. Such affinity tags can facilitate the purification of recombinant variant proteins.

For methods in which the variant proteins are delivered to cells, the proteins can be produced using any method known in the art, e.g., by in vitro translation, or expression in a suitable host cell from nucleic acid encoding the variant protein; a number of methods are known in the art for producing proteins. For example, the proteins can be produced in and purified from yeast, E. coli, insect cell lines, plants, transgenic animals, or cultured mammalian cells; see, e.g., Palomares et al., "Production of Recombinant Proteins: Challenges and Solutions," Methods Mol Biol. 2004; 267: 15-52. In addition, the variant proteins can be linked to a moiety that facilitates transfer into a cell, e.g., a lipid nanoparticle, optionally with a linker that is cleaved once the protein is inside the cell. See, e.g., LaFountaine et al., Int J Pharm. 2015 Aug. 13; 494(1):180-194.

Expression Systems

To use the Cpf1 fusion proteins described herein, it may be desirable to express them from a nucleic acid that encodes them. This can be performed in a variety of ways. For example, the nucleic acid encoding the Cpf1 fusion proteins can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the Cpf1 fusion proteins for production of the Cpf1 fusion proteins. The nucleic acid encoding the Cpf1 fusion proteins can also be cloned into an expression vector, for administration to a plant cell, animal cell, preferably a mammalian cell or a human cell, fungal cell, bacterial cell, or protozoan cell.

To obtain expression, a sequence encoding a Cpf1 fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the Cpf1 fusion protein is to be administered in vivo for gene regulation, either a constitutive or an inducible promoter can be used, depending on the particular use of the Cpf1 fusion protein. In addition, a preferred promoter for administration of the Cpf1 fusion protein can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the Cpf1 fusion proteins, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the Cpf1 fusion proteins, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the Cpf1 fusion proteins can include RNA Pol III promoters to drive expression of the guide RNAs, e.g., the H1, U6 or 7SK promoters. These human promoters allow for expression of Cpf1 fusion proteins in mammalian cells following plasmid transfection.

In some embodiments, a single nucleic acid encoding a plurality of Cpf1 gRNAs is used, e.g., as follows (SEQ ID NO: 7)
GAGGGCCTATTTCCCATGATTOOTTCATATTTGCATATACGATACAAGG

CTGTTAGAGAGATAATTAGAATTAATTTGACTGTAAACACAAAGATATT

AGTACAAAATACGTGACGTAGAAAGTAATAATTTCTTGGGTAGTTTGCA

GTTTTAAAATTATGTTTTAAAATGGACTATCATATGCTTACCGTAACTT

GAAAGTATTTCGATTTCTTGGCTTTATATATCTTGTGGAAAGGACGAAA

CACC*GAATTTCTACTAAGTGTAGAT*[spacer_sequence_1]*AATTT*

*CTACTAAGTGTAGAT*[spacer_sequence_2]*AATTTCTACTAAGTG*

*TAGAT*[spacer_sequence_3]*AATTTCTACTAAGTGTAGAT*

*TTTTTTT*

The hU6 promoter is shown in bold above.

The Lb crRNA direct repeats are AATTTCTACTAAGTGTAGAT (SEQ ID NO:38, shown in italics above. The spacer sequences of 17-20 nts (preferably 20) that direct the Cpf1 to the target gene are indicated as spacer sequence 1, 2, or 3.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the Cpf1 variant.

The present invention also includes the vectors and cells comprising the vectors, and cells and transgenic animals expressing the fusion proteins.

EXAMPLES

The invention is further described in the following examples, which do not limit the scope of the invention described in the claims.

Methods

The following materials and methods were used in the Examples below.

Plasmids and Oligonucleotides.

A list of plasmids, and related sequences used in this study are found in the Sequences section, below; LbCpf1 crRNA information is in Table 1.

TABLE 1

Single Cpf1 crRNAs

| Name | Spacer Sequence with Cpf1 PAM | SEQ ID NO | Genomic coordinates |
|---|---|---|---|
| HBB_P_1 guide | TTTGTACTGATGGTATGGGGCCAA | 39 | Chr11: 5248505-5248528 |
| HBB_P_2 guide | TTTGAAGTCCAACTCCTAAGCCAG | 40 | Chr11: 5248452-5248475 |
| HBB_P_3 guide | TTTGCAAGTGTATTTACGTAATAT | 41 | Chr11: 5248550-5248573 |
| AR_P_1 guide | TTTGAGAGTCTGGATGAGAAATGC | 42 | ChrX: 66763209-66763232 |
| AR_P_2 guide | TTTCTACCCTCTTCTCTGCCTTTC | 43 | ChrX: 66763260-66763283 |
| AR_P_3 guide | TTTGCTCTAGGAACCCTCAGCCCC | 44 | ChrX: 66763299-66763322 |
| NPY1R_P_1 guide | TTTCAAGCCTCGGGAAACTGCCCT | 45 | Chr4: 164254005-164254028 |
| NPY1R_P_2 guide | TTTCTTTGTTTGCAGGTCAGTGCC | 46 | Chr4: 164254048-164254071 |
| NPY1R_P_3 guide | TTTGGGCTGGCGCTCGAGCTCTCC | 47 | Chr4: 164254099-164254122 | dLbCpf1-p65 and dLbCpf1-VPR plasmids (JG1202 and JG1211, respectively) were constructed by cloning p65 and VPR into dLbCpf1 (MMW1578) using BstZ17I and Not I sites through Gibson assembly. VPR was amplified from SP-dCas9-VPR which was a gift from George Church (Addgene plasmid #63798)[46]. dLbCpf1-DmrA(X1) to dLbCpf1-DmrA(X4) (JG674, JG676, JG693, and YET1000, respectively) were generated by inserting dLbCpf1 into AgeI and XhoI digested constructs that have different numbers of DmrA domains (BPK1019, BPK1033, BPK1140, BPK1179 for dCas9-DmrA(X1) to dCas9-DmrA(X4), respectively) using Gibson cloning method. A previously described plasmid encoding DmrC was digested with NruI and p65 or VPR with G4S-linker were added via Gibson assembly for DmrC-P65 (BPK1169) and DmrC-VPR (MMW948). For constructing single crRNA plasmids, oligonucleotide pairs for crRNA spacers were annealed and ligated into BsmBI-digested LbCpf1 crRNA backbone plasmid, BPK3082 (Addgene #78742)[14]. For the cloning of multiplexed crRNAs used in this study, three pairs of oligonucleotides were designed to have overhangs. Each oligonucleotides pair was annealed in the presence of T4 PNK, and all three oligo pairs are ligated to BsmBI and HindIII-digested LbCpf1 crRNA backbone plasmid, BPK3082 in one reaction. Sequences for all oligo pairs are listed in Tables 2A-B.

TABLE 2A

Multiplexed Cpf1 crRNAs targeting a single promoter

| Name | Pair # | Oligonucleotides sequences to be ordered | Orientation | SEQ ID NO: |
|---|---|---|---|---|
| HBB_ Multiplexed | Pair1 | AGATTACTGATGGTATGGGGCCAAA | Top | 8 |
| | | TAGTAGAAATTTTGGCCCCATACCATCAGTA | Bottom | 9 |
| | Pair 2 | ATTTCTACTAAGTGTAGATAAGTCCAA CTCCTAAGCCAGAATTTCTACTAA | Top | 10 |
| | | ATCTACACTTAGTAGAAATTCTGGCTT AGGAGTTGGACTTATCTACACT | Bottom | 11 |
| | Pair 3 | GTGTAGATCAAGTGTATTTACGTAATA TAATTTCTACTAAGTGTAGATTTTTTTA | Top | 12 |
| | | AGCTTAAAAAAATCTACACTTAGTAG AAATTATATTACGTAAATACACTTG | Bottom | 13 |

TABLE 2A-continued

Multiplexed Cpf1 crRNAs targeting a single promoter

| Name | Pair # | Oligonucleotides sequences to be ordered | Orientation | SEQ ID NO: |
|---|---|---|---|---|
| AR_ Multiplexed | Pair1 | AGATAGAGTCTGGATGAGAAATGCA | Top | 14 |
| | | TAGTAGAAATTGCATTTCTCATCCAGACTCT | Bottom | 15 |
| | Pair 2 | ATTTCTACTAAGTGTAGATTACCCTCTT CTCTGCCTTTCAATTTCTACTAA | Top | 16 |
| | | ATCTACACTTAGTAGAAATTGAAAGGCAG AGAAGAGGGTAATCTACACT | Bottom | 17 |
| | Pair 3 | GTGTAGATCTCTAGGAACCCTCAGCCCCAA TTTCTACTAAGTGTAGATTTTTTTA | Top | 18 |
| | | AGCTTAAAAAAAATCTACACTTAGTAGAAA TTGGGGCTGAGGGTTCCTAGAG | Bottom | 19 |
| NPY1R_ Multiplexed | Pair1 | AGATAAGCCTCGGGAAACTGCCCTA | Top | 20 |
| | | TAGTAGAAATTAGGGCAGTTTCCCGAGGCTT | Bottom | 21 |
| | Pair 2 | ATTTCTACTAAGTGTAGATTTTGTTTGCAGGT CAGTGCCAATTTCTACTAA | Top | 22 |
| | | ATCTACACTTAGTAGAAATTGGCACTGACCT GCAAACAAAATCTACACT | Bottom | 23 |
| | Pair 3 | GTGTAGATGGCTGGCGCTCGAGCTCTCCAA TTTCTACTAAGTGTAGATTTTTTTA | Top | 24 |
| | | AGCTTAAAAAAAATCTACACTTAGTAGAAA TTGGAGAGCTCGAGCGCCAGCC | Bottom | 25 |

TABLE 2B

Multiplexed Cpf1 crRNAs targeting multiple promoters

| Name | Pair # | Oligonucleotides sequences to be ordered | Orientation | SEQ ID NO: |
|---|---|---|---|---|
| HBB_AR_ NPY1R_ Multiplexed | Pair1 | AGATTACTGATGGTATGGGGCCAAA | Top | 26 |
| | | TAGTAGAAATTTTGGCCCCATACCATCAGTA | Bottom | 27 |
| | Pair 2 | ATTTCTACTAAGTGTAGATCTCTAGGAACC CTCAGCCCCAATTTCTACTAA | Top | 28 |
| | | ATCTACACTTAGTAGAAATTGGGGCTGAG GGTTCCTAGAGATCTACACT | Bottom | 29 |
| | Pair 3 | GTGTAGATAAGCCTCGGGAAACTGCCCTAA TTTCTACTAAGTGTAGATTTTTTTA | Top | 30 |
| | | AGCTTAAAAAAAATCTACACTTAGTAGAAA TTAGGGCAGTTTCCCGAGGCTT | Bottom | 31 |

Human Cell Culture and Transfection.

HEK293 cells were grown at 37°, in 5% CO2 in Dulbecco's Modified Eagle Medium (DMEM) with 10% fetal bovine serum and 1% penicillin and streptomycin. 750 ng of dLbCpf1-p65/VPR with 250 ng of LbCpf1 crRNAs were co-transfected using a 3 ul of TransIT®-LT1 Transfection Reagent (Minis, cat #MIR2300) into HEK293 cells in a 12-well plate. 400 ng of dLbCpf1 fused with different numbers of DmrA, 200 ng of DmrC-p65/VPR, and 400 ng of LbCpf1 crRNAs were co-transfected using 3 ul of LT-1 into HEK293 cells in a 12-well plate.

Reverse Transcription Quantitative PCR.

Total RNA was extracted from the transfected cells 72 hours post-transfection using the NucleoSpin® RNA Plus (Clontech, cat #740984.250), and 250 ng of purified RNA was used for cDNA synthesis using High-Capacity RNA-cDNA kit (ThermoFisher, cat #4387406). cDNA was diluted 1:20 and 3 ul of cDNA was used for quantitative PCR (qPCR). qPCR reaction samples were prepared using cDNA, SYBR (ThermoFisher, cat #4385612), and primers detecting each target transcript. Primer sequences are listed in Table 3. qPCR was performed using Roche LightCycler480. When Ct values are over 35, we considered them as 35, because Ct values fluctuate for very low expressed transcripts. Samples that were transfected with LbCpf1 crRNA backbone plasmid, BPK3082 were used as negative controls, and the levels of fold activation over negative controls were normalized to the expression of HPRT1.

TABLE 3

RT-qPCR primers

| Primer name | Sequence | SEQ ID NO: | Orien- tation | Target Gene |
|---|---|---|---|---|
| oET_173 | ATGGTGAGCAGAGTGCCCTATC | 32 | F | NPY1R |
| oET_174 | ATGGTCCCTGGCAGTCTCCAAA | 33 | R | |
| oET_175 | CCATCGGACTCTCATAGGTTGTC | 34 | F | AR |
| oET_176 | GACCTGTACTTATTGTCTCTCATC | 35 | R | |
| oET_225 | GCACGTGGATCCTGAGAACT | 36 | F | HBB |
| oET_226 | ATTGGACAGCAAGAAAGCGAG | 37 | R | |

F, Forward; R, Reverse

Figure 1B:
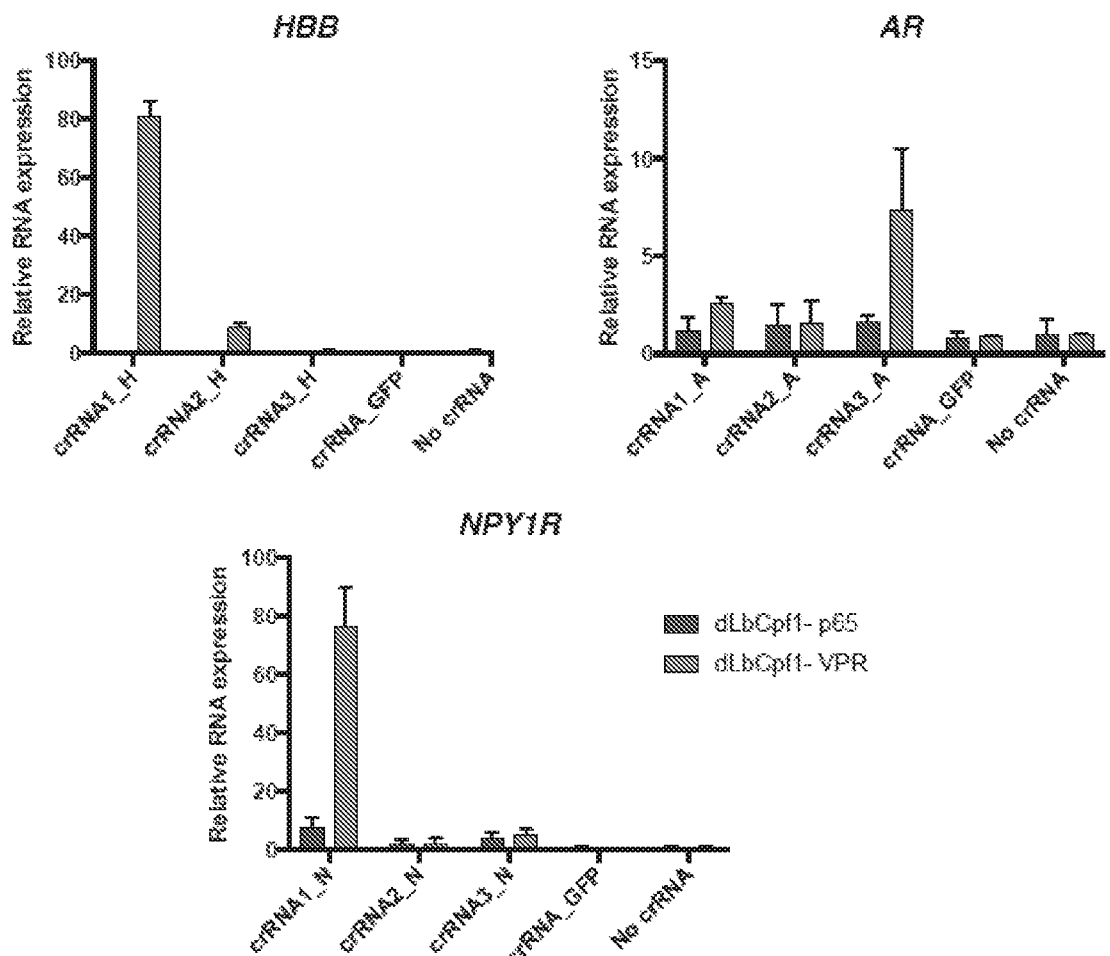

Example 1. Targeted Human Endogenous Gene Regulation Using Individual crRNAs with dLbCpf1-Based Activators In initial experiments, we tested whether direct fusions of a catalytically inactive Cpf1 nuclease to transcriptional activation domains (FIG. 1A) could activate endogenous human gene promoters. We targeted the promoters of three different endogenous genes that are not expressed in human HEK293 cells (HBB, AR, and NPY1R) by designing three crRNAs for each promoter (See Tables 2A-B). We used a catalytically inactive nuclease-dead version of Cpf1 from Lachnospiraceae bacterium ND2006 (dLbCpf1) because we and others have shown this has higher nuclease activities compared to the other Cpf1 nuclease reported to be active in human cells (AsCpf1 from Acidaminococcus sp. BV3L6)[14, 36, 44]. dLbCpf1 fusions to a single human NF-KB p65 activation domain tested with the nine individual crRNAs either failed to increase or only weakly increased transcription from the three human gene target promoters (FIG. 1B), consistent with previously published results with single activation domain fusions to dSpCas9[46]. By contrast, dLbCpf1 fusions to the synthetic multimerized VPR activator (consisting of four copies of the viral-based VP16 activator, the human NF-KB p65 activation domain, and the Epstein-Barr virus R transactivator Rta) could significantly activate transcription with at least one crRNA for each of the three target genes (FIG. 1B). This result is similar to previous experiments with dSpCas9 activators, which demonstrated the need to recruit multiple transcriptional activation domains to achieve efficient upregulation of target gene promoter activity[46, 47].

We also tested a larger series of 32 crRNAs positioned within 1 kb upstream or 500 bp downstream of the TSSs of two additional endogenous genes, CD5 and CD22, which encode cell surface proteins. Most of the 32 crRNAs tested could significantly activate the target gene promoter when positioned between ~600 bp upstream and ~400 bp downstream of the TSSs (FIG. 1C), consistent with results obtained using dSpCas9 activators[3]. The levels of activation observed with dLbCpf1-based activators are comparable to what might be observed in naturally occurring biological systems and are similar to what has been reported previously for analogous dCas9-based activators.

Figure 1D:
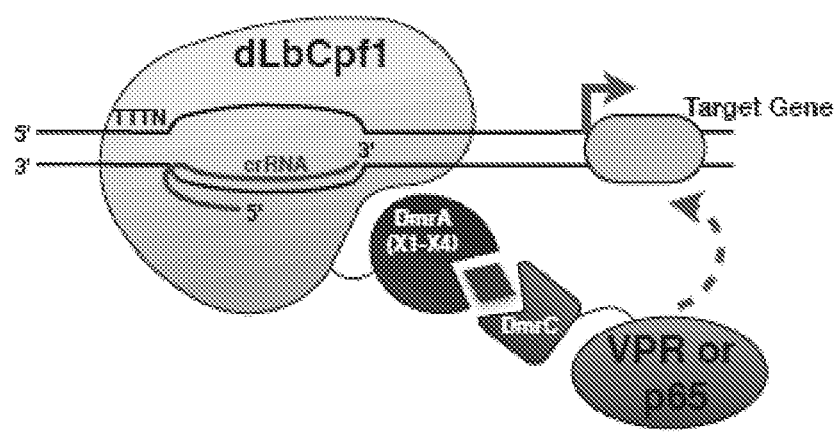
Figure 1E:
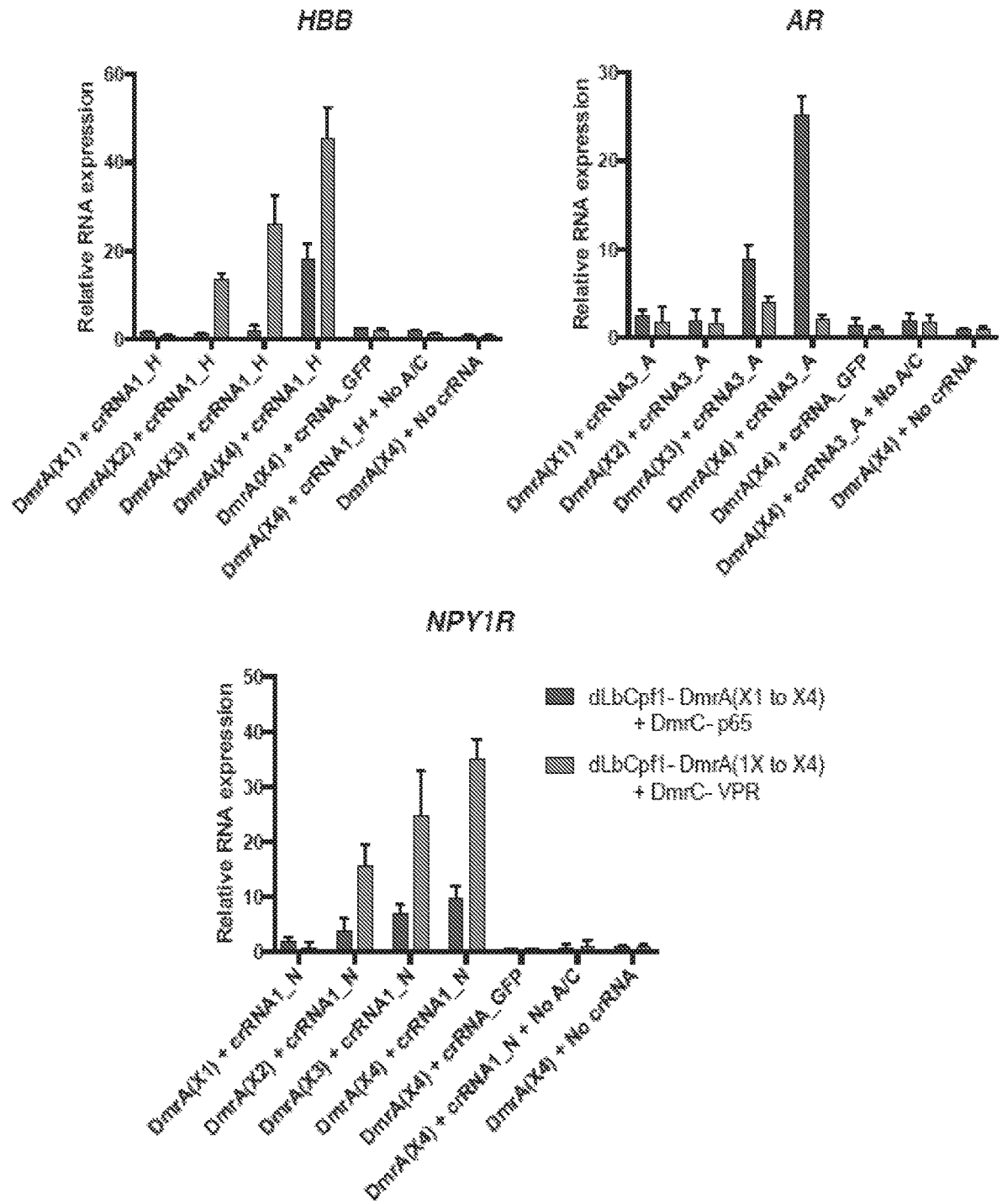

We next sought to develop chemically inducible, bipartite dLbCpf1-based transcriptional activators. We envisioned using a dimerization system of fragments of the FK506-binding protein (FKBP) and FKBP-rapamycin-binding protein (FRB) known as the DmrA and DmrC domains, respectively, that interact only in the presence of a rapamycin analog known as the A/C heterodimerizer[48], to split dLbCpf1 activators into two parts that would assemble only in the presence of the A/C drug (FIG. 1D). dLbCpf1 fused to a single DmrA domain together with a DmrC domain fused to either NF-KB p65 or VPR failed to activate transcription of the HBB, AR, or NPY1R genes with any of the single crRNAs that had worked efficiently at these promoters with the direct dLbCpf1 activator fusions (FIG. 1E). Reasoning that increasing the number of DmrA domains linked to dLbCpf1 might increase the efficiency of gene activation, we constructed fusions harboring two, three or four DmrA domains. Testing of these fusions with DmrC-VPR with single crRNAs revealed activation at two of the three endogenous gene promoters (HBB and NPY1R; FIG. 1E), with increasing effects observed with more DmrA domains and with maximum levels reaching approximately half of that observed with direct dLbCpf1-VPR fusions. This maximal level of activation was dependent on the presence of the A/C heterodimerizer drug (FIG. 1E), demonstrating that this system is drug-inducible.

Surprisingly, these dLbCpf1 fusions together with DmrC-p65 could robustly activate transcription from all three target gene promoters using single crRNAs (FIG. 1E), an unexpected finding given the lack of activation observed with direct dLbCpf1-p65 fusions with the same crRNAs (FIG. 1B). For the AR promoter, DmrC-p65 could activate transcription by ~25-fold compared with the lack of an effect by DmrC-VPR. For the HBB and NPY1R promoters, the levels of activation observed with DmrC-p65 were somewhat less (~50% and ~30%, respectively) than those obtained with DmrC-VPR but still robust in absolute terms (~20-fold and ~10-fold activation). Maximal activation with DmrC-p65 fusions was again dependent on the presence of A/C heterodimerizer drug. Taken together, these findings demonstrate that p65 can provide an important alternative to VPR for the drug-inducible dLbCpf1 activator platform.

Figure 2A:
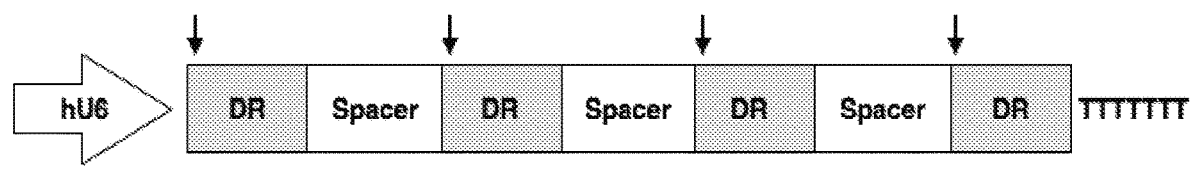
Figure 2B:
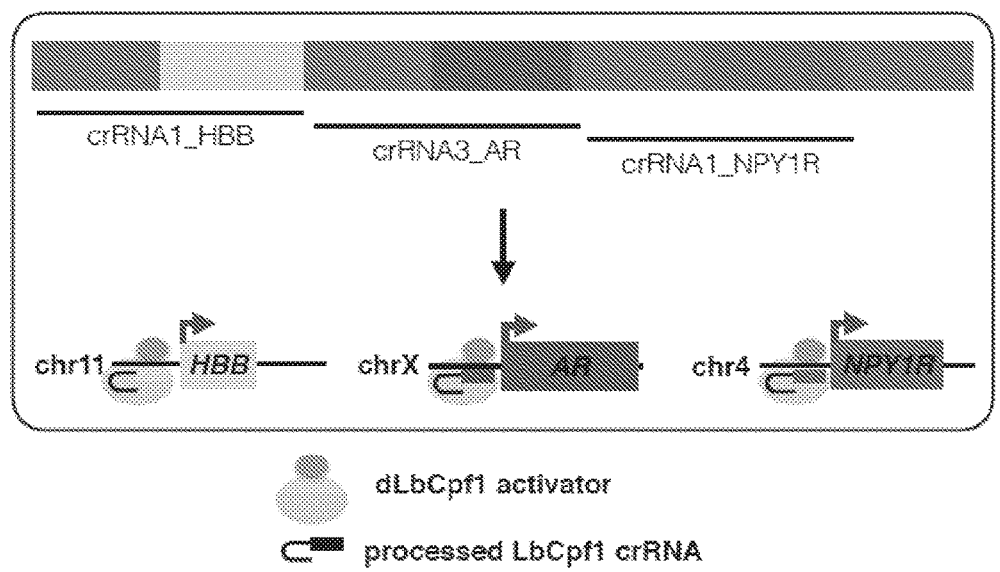
Figure 2C:
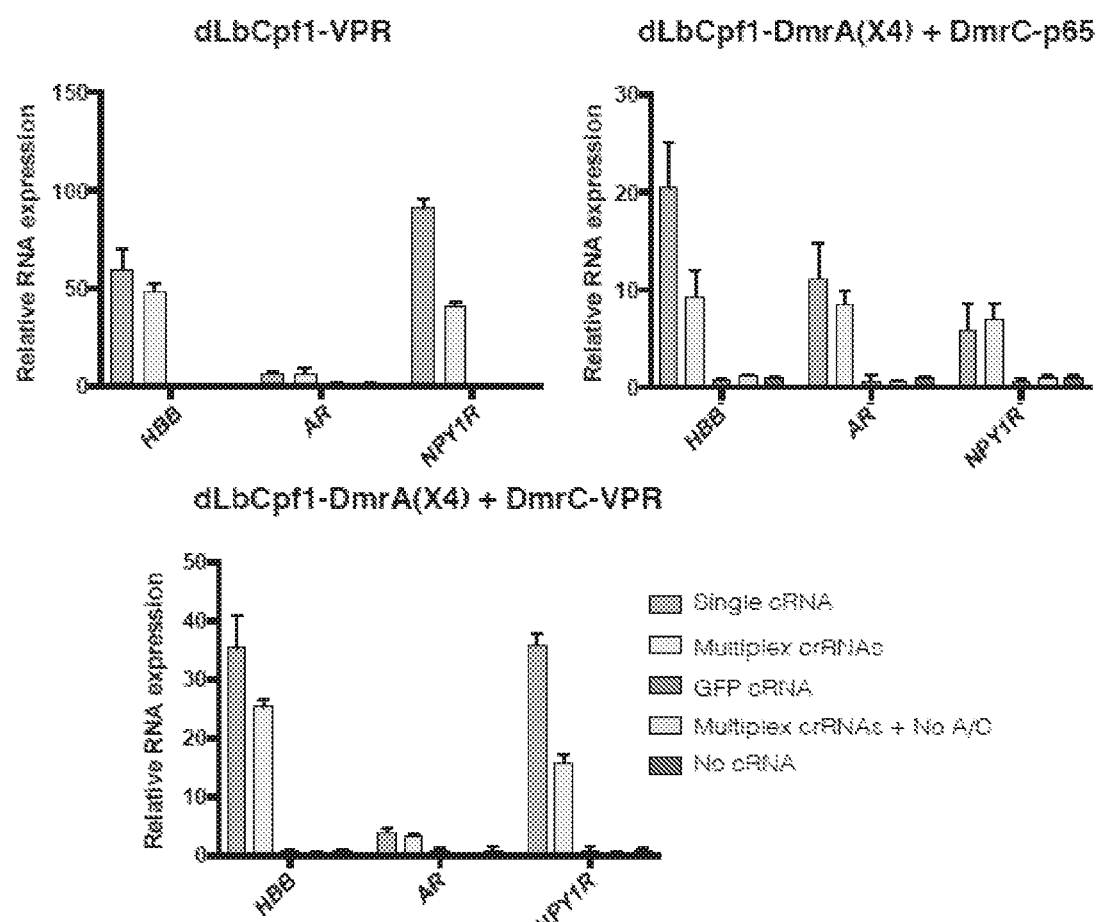

Example 2. Multiplex and Synergistic Regulation of Endogenous Human Genes by dLbCpf1-Based Activators A major advantage of Cpf1 nuclease relative to Cas9 nuclease is the ability to more easily express more than one guide RNA for multiplex applications. Previous work has shown that multiple crRNAs encoded in a single transcript driven by a U6 promoter can be processed into individual crRNAs by Cpf1 itself (FIG. 2A), enabling multiplex induction of mutagenic genome editing events[49]. We tested whether we could use dLbCpf1-based systems to activate three different endogenous human genes using three crR- NAs, each already shown to be active with a dLbCpf1-based activator and all encoded on a single transcript (FIG. 2B). Testing of these multiplex crRNA transcripts revealed that these could be used together with dLbCpf1-VPR direct fusions, with dLbCpf1-DmrA(×4) and DmrC-VPR fusions, and with dLbCpf1-DmrA(×4) and DmrC-p65 fusions to mediate transcriptional activation of multiple endogenous gene promoters in human HEK293 cells (FIG. 2C). The magnitudes of activation observed with the multiplex crRNAs were somewhat lower (~18 to 55%) than those observed with expression of a single crRNA. One possible explanation for this difference might be greater competition for binding to dLbCpf1 fusion proteins due to the presumably three-fold higher levels of crRNA present in cells expressing the multiplex transcript. Nonetheless, these results demonstrate that as many as three crRNAs encoded in a larger multiplex transcript can be used to activate transcription of multiple gene targets using dLbCpf1-based activators.

Figure 2D:
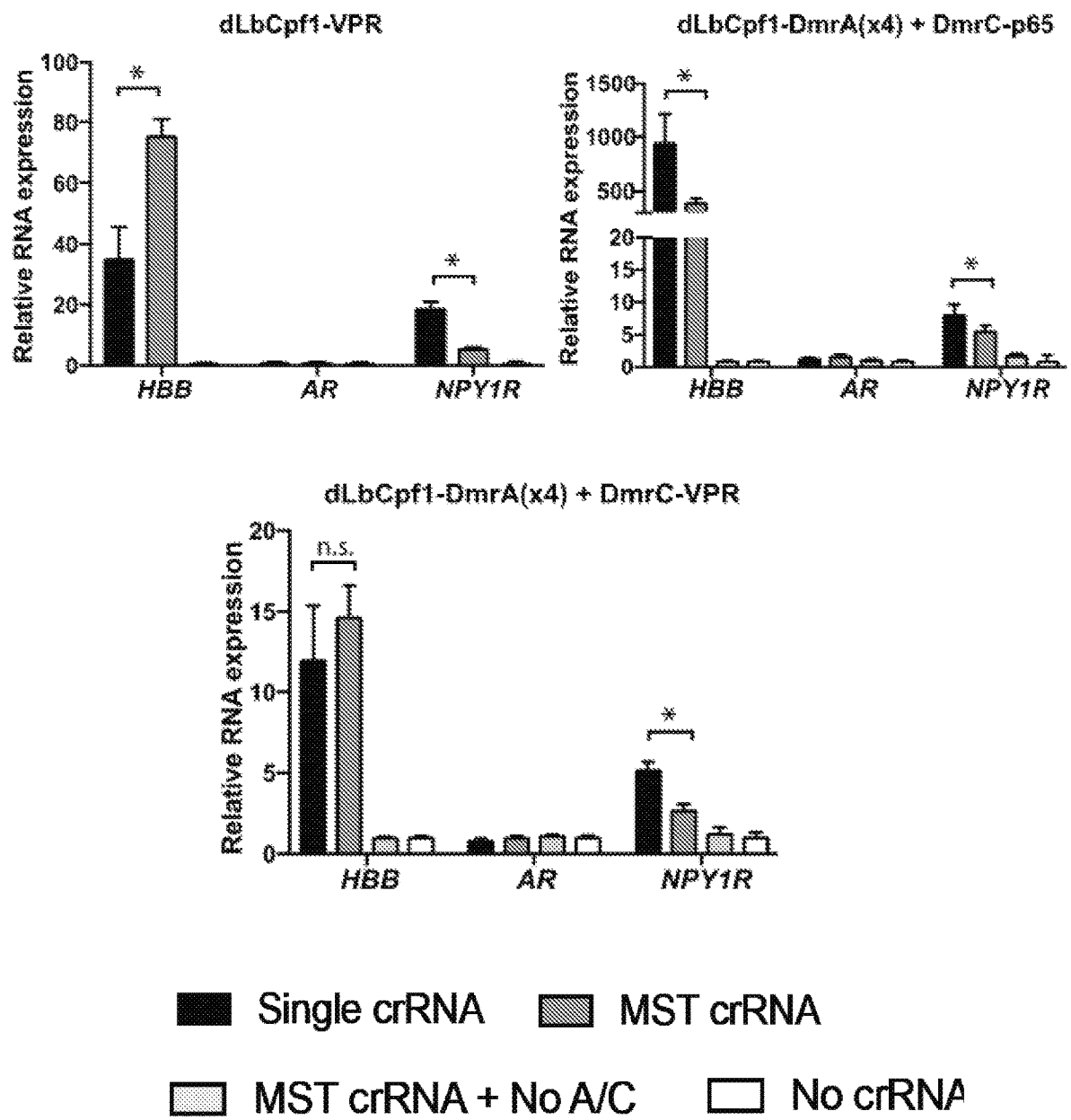

To extend our findings to another human cell line, we also tested the direct VPR activator fusions and drug-regulated VPR and p65 activators in human U2OS cells, targeting the same genes (HBB, AR, and NPY1R) with MST crRNAs and single crRNAs (FIG. 2D). We observed that HBB and NPY1R were highly upregulated and that HBB activation with DmrC-p65 was even greater than in HEK293s. We did not observe activation of the AR gene but this is likely because its baseline expression is already highly elevated in U2OS cells (with a basal quantitative RT-PCR Ct value of ~28). Relative differences in the efficacies of crRNAs expressed singly or in MSTs were similar to what we observed in HEK293s.

Figure 2E:
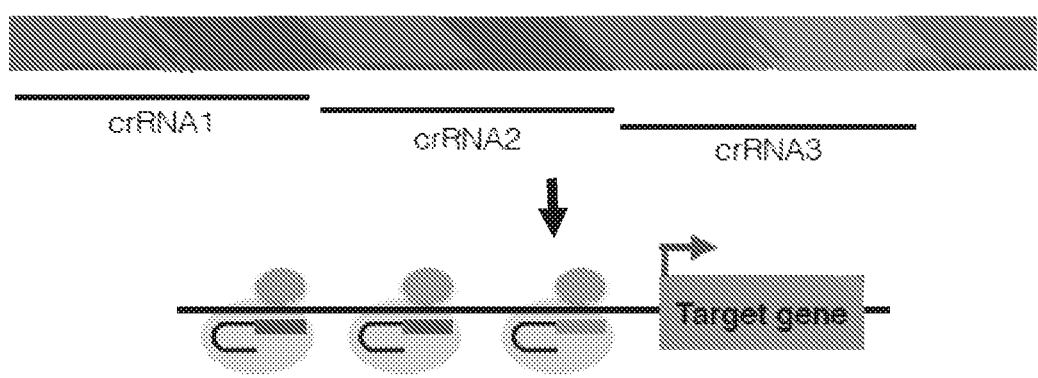
Figure 2F:
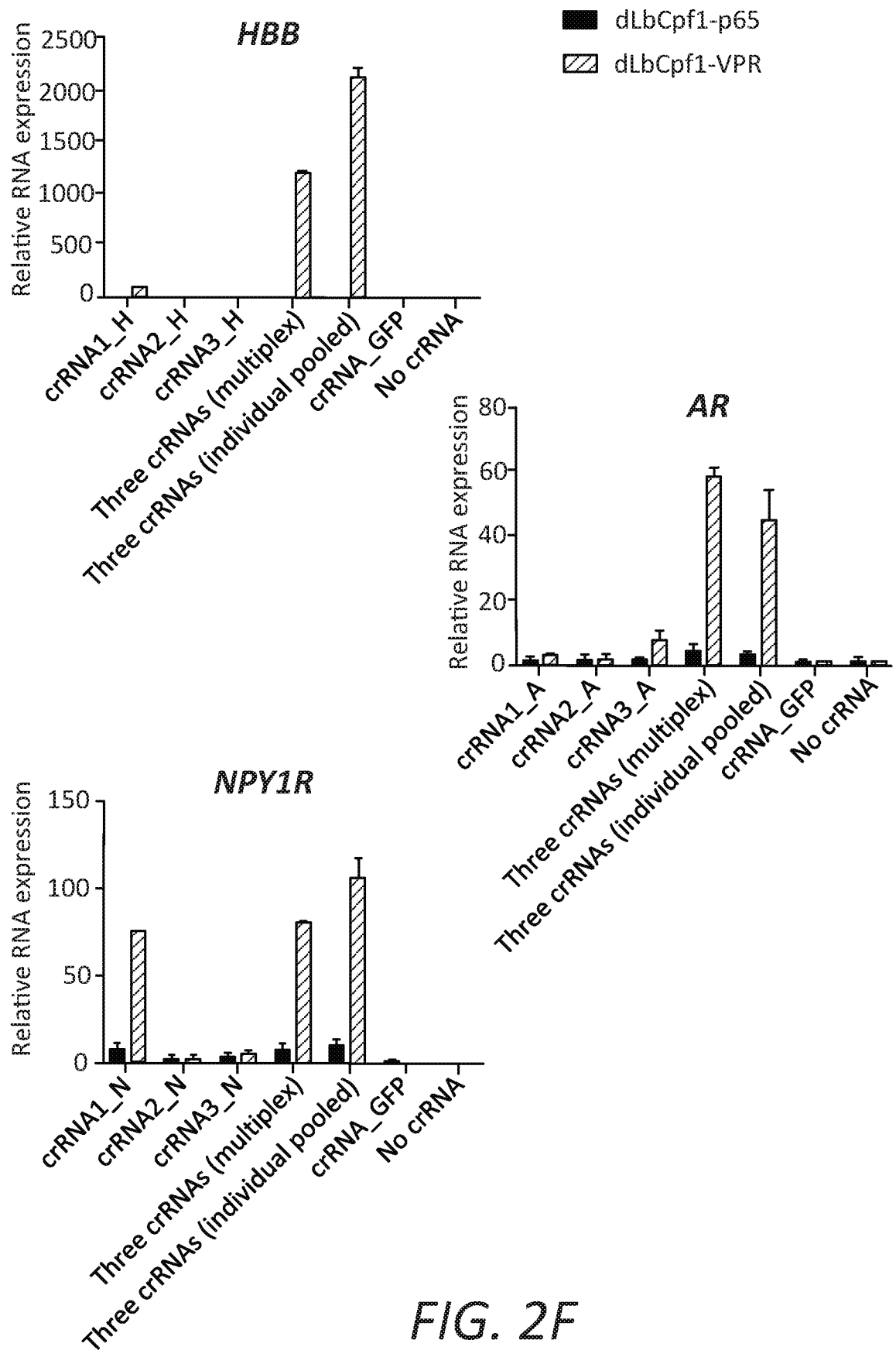
Figure 2G:
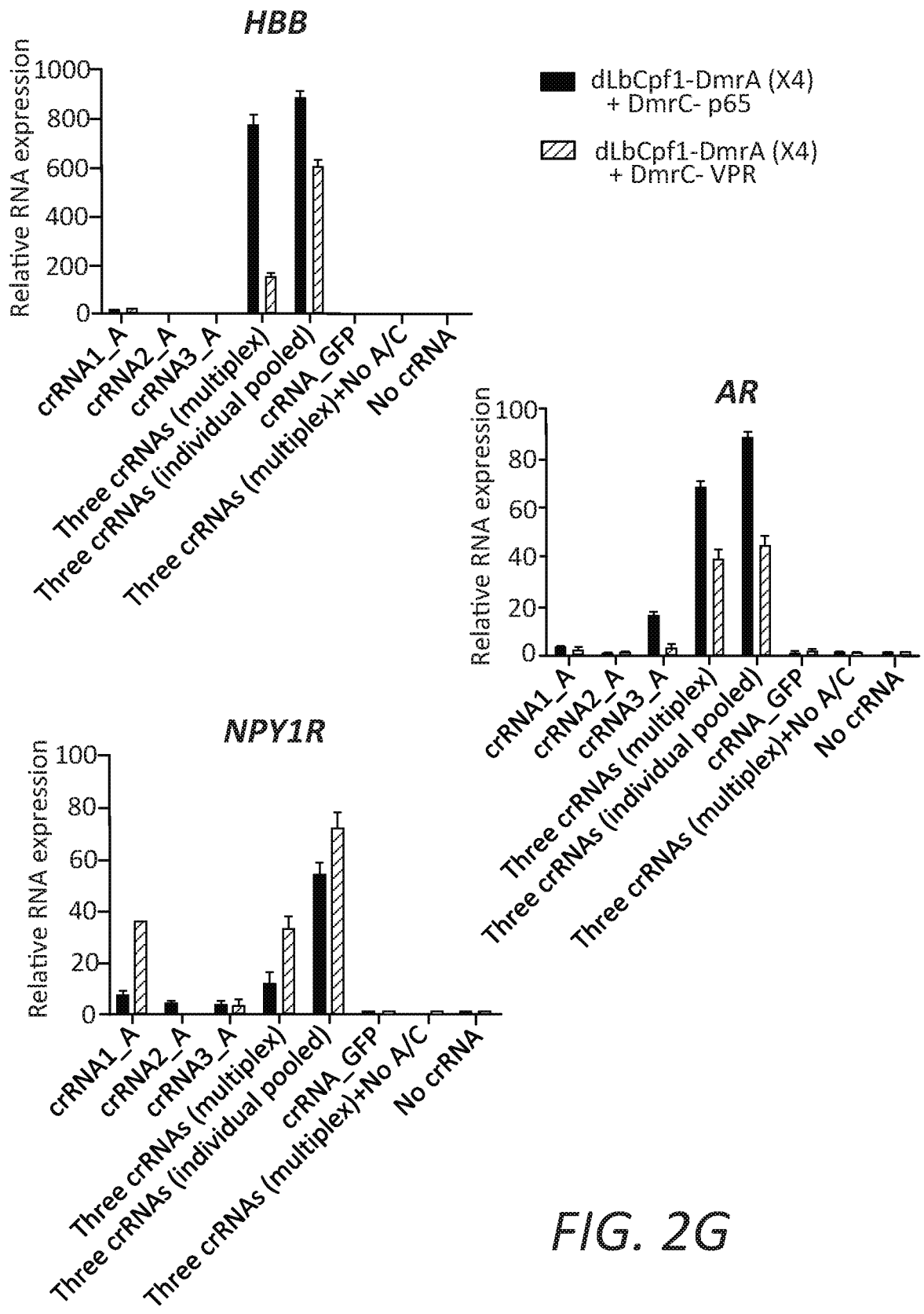

We also sought to determine whether multiple crRNAs expressed from a single construct are actually active in the same cell. Because our experiments were performed on populations of cells with transient transfection of expression vectors, it is formally possible that the multiplex gene activation we observed above was due to different crRNAs being active in different cells within the population of transfected cells. To rule out this possibility, we reasoned that if multiple crRNAs designed against sites within the same gene promoter are expressed from the same transcript within a single cell, this should lead to synergistic increases in transcription from the target gene promoter (FIG. 2E) (synergistic activation is defined as greater than additive effects or two or more activators acting on the same promoter[2]). With direct fusions of VPR to dLbCpf1, we observed synergistic activation using three crRNAs expressed in a single transcript for two of the three endogenous gene promoters we examined (HBB and AR; FIG. 2F). For the third gene promoter (NPY1R), we did not observe synergistic activation with the three crRNAs when expressed from the same transcript but did see synergy in a control experiment when they were expressed as separate RNAs introduced simultaneously (FIG. 2F). We also did not observe synergistic activation with direct fusions of p65 to dLbCpf1 at any of the three genes with three crRNAs expressed either from the same transcript or from separate transcripts (FIG. 2F). With the drug-inducible dLbCpf1 and VPR activator system, we again observed synergy at the HBB and AR promoters but only with the transcripts expressed separately at the NPY1R promoter (FIG. 2G). A similar pattern of results was observed with the drug-inducible LbCpf1 and p65 system (FIG. 2G). Importantly, the synergistic activation levels observed with the p65 activation domain on the HBB and AR genes were again higher than in comparable experiments performed with the VPR activator (FIG. 2G). Taken together, we conclude that multiple active crRNAs can be expressed from a single transcript in the same cell, albeit with somewhat lower activity than if they are expressed from multiple separate expression vectors.

Figure 2H:
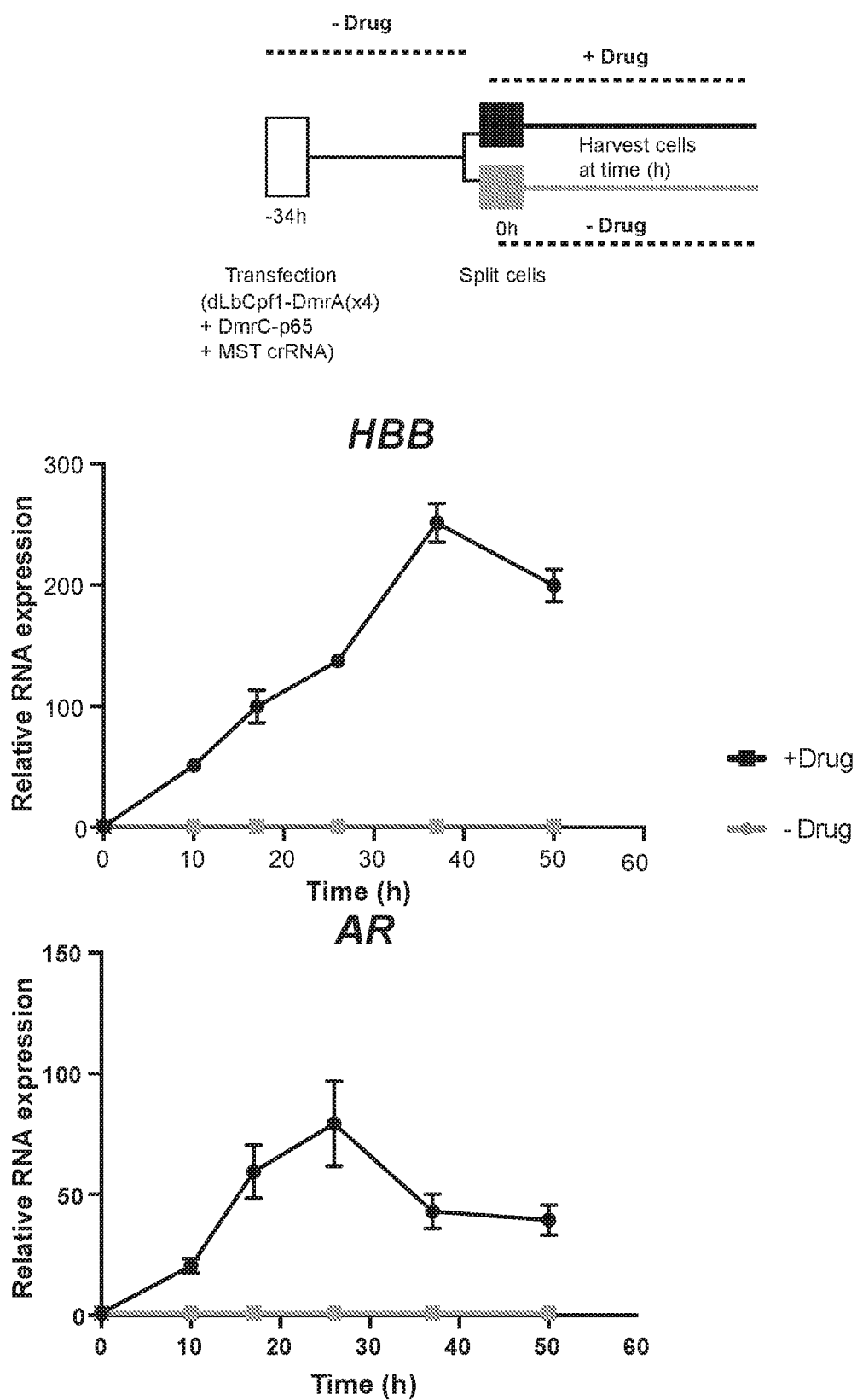
Figure 21:
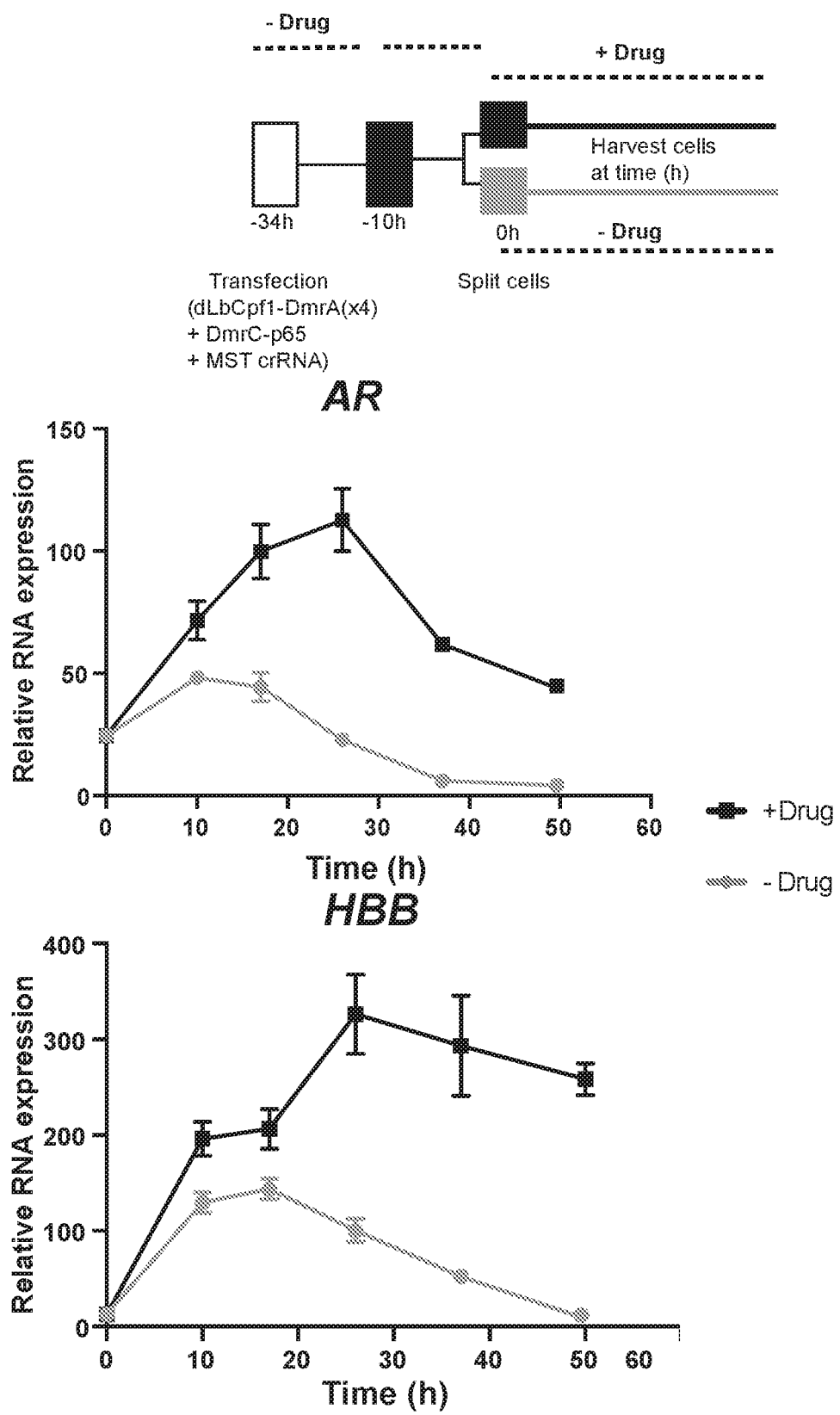

In addition, we assessed the kinetics of activator effects to the addition and withdrawal of A/C heterodimerizer. We found that maximum activation of the HBB and AR genes was observed ~25 to 35 hours after the addition of drug (FIG. 2H) and return of activated gene expression to baseline occurred ~35 to 45 hours after withdrawal of the drug (FIG. 2I). We envision that drug-inducibility could be easily extended to other orthologues and we have successfully used these same strategies to regulate and tune dSpCas9-based activators Sequences

| Name | Addgene # | Description |
| --- | --- | --- |
| MMW1578 | 104563 | CAG-human dLbCpf1(D832A)-NLS-3xHA |
| BPK1169 | | CAG-DmrC-NLS-FLAG-P65 |
| MMW948 | 104565 | CAG-DmrC-NLS-FLAG-VPR |
| JG1202 | | CAG-human dLbCpf1(D832A)-NLS-3xHA-P65 |
| JG1211 | 104567 | CAG-human dLbCpf1(D832A)-NLS-3xHA-VPR |
| JG674 | 104568 | CAG-human dLbCpf1(D832A)-NLS-3xHA-DmrA(X1) |
| JG676 | 104569 | CAG-human dLbCpf1(D832A)-NLS-3xHA-DmrA(X2) |
| JG693 | 104570 | CAG-human dLbCpf1(D832A)-NLS-3xHA-DmrA(X3) |
| YET1000 | 104571 | CAG-human dLbCpf1(D832A)-NLS-3xHA-DmrA(X4) |
| BPK3082 | 78742 | U6-LbCpf1-crRNA-BsmBIcassette |

1. MMW1578: CAG-Human dLbCpf1(D832A)-NLS-3×HA

Human codon optimized dLbCpf1: bold, NLS: italic, 3xHA: lower case
(SEQ ID NO: 48)

```
ATGAGCAAGCTGGAGAAGTTTACAAACTGCTACTCCCTGTCTAAGACCCTGAGG

TTCAAGGCCATCCCTGTGGGCAAGACCCAGGAGAACATCGACAATAAGCGGCT

GCTGGTGGAGGACGAGAAGAGAGCCGAGGATTATAAGGGCGTGAAGAAGCTGC

TGGATCGCTACTATCTGTCTTTTATCAACGACGTGCTGCACAGCATCAAGCTGAA

GAATCTGAACAATTACATCAGCCTGTTCCGGAAGAAAACCAGAACCGAGAAGGA

GAATAAGGAGCTGGAGAACCTGGAGATCAATCTGCGGAAGGAGATCGCCAAGG

CCTTCAAGGGCAACGAGGGCTACAAGTCCCTGTTTAAGAAGGATATCATCGAGA
```

-continued

```
CAATCCTGCCAGAGTTCCTGGACGATAAGGACGAGATCGCCCTGGTGAACAGCT

TCAATGGCTTTACCACAGCCTTCACCGGCTTCTTTGATAACAGAGAGAATATGTT

TTCCGAGGAGGCCAAGAGCACATCCATCGCCTTCAGGTGTATCAACGAGAATCT

GACCCGCTACATCTCTAATATGGACATCTTCGAGAAGGTGGACGCCATCTTTGAT

AAGCACGAGGTGCAGGAGATCAAGGAGAAGATCCTGAACAGCGACTATGATGT

GGAGGATTTCTTTGAGGGCGAGTTCTTTAACTTTGTGCTGACACAGGAGGGCATC

GACGTGTATAACGCCATCATCGGCGGCTTCGTGACCGAGAGCGGCGAGAAGAT

CAAGGGCCTGAACGAGTACATCAACCTGTATAATCAGAAAACCAAGCAGAAGCT

GCCTAAGTTTAAGCCACTGTATAAGCAGGTGCTGAGCGATCGGGAGTCTCTGAG

CTTCTACGGCGAGGGCTATACATCCGATGAGGAGGTGCTGGAGGTGTTTAGAAA

CACCCTGAACAAGAACAGCGAGATCTTCAGCTCCATCAAGAAGCTGGAGAAGCT

GTTCAAGAATTTTGACGAGTACTCTAGCGCCGGCATCTTTGTGAAGAACGGCCC

CGCCATCAGCACAATCTCCAAGGATATCTTCGGCGAGTGGAACGTGATCCGGGA

CAAGTGGAATGCCGAGTATGACGATATCCACCTGAAGAAGAAGGCCGTGGTGA

CCGAGAAGTACGAGGACGATCGGAGAAAGTCCTTCAAGAAGATCGGCTCCTTTT

CTCTGGAGCAGCTGCAGGAGTACGCCGACGCCGATCTGTCTGTGGTGGAGAAG

CTGAAGGAGATCATCATCCAGAAGGTGGATGAGATCTACAAGGTGTATGGCTCC

TCTGAGAAGCTGTTCGACGCCGATTTTGTGCTGGAGAAGAGCCTGAAGAAGAAC

GACGCCGTGGTGGCCATCATGAAGGACCTGCTGGATTCTGTGAAGAGCTTCGAG

AATTACATCAAGGCCTTCTTTGGCGAGGGCAAGGAGACAAACAGGGACGAGTC

CTTCTATGGCGATTTTGTGCTGGCCTACGACATCCTGCTGAAGGTGGACCACATC

TACGATGCCATCCGCAATTATGTGACCCAGAAGCCCTACTCTAAGGATAAGTTCA

AGCTGTATTTTCAGAACCCTCAGTTCATGGGCGGCTGGGACAAGGATAAGGAGA

CAGACTATCGGGCCACCATCCTGAGATACGGCTCCAAGTACTATCTGGCCATCA

TGGATAAGAAGTACGCCAAGTGCCTGCAGAAGATCGACAAGGACGATGTGAAC

GGCAATTACGAGAAGATCAACTATAAGCTGCTGCCCGGCCCTAATAAGATGCTG

CCAAAGGTGTTCTTTTCTAAGAAGTGGATGGCCTACTATAACCCCAGCGAGGAC

ATCCAGAAGATCTACAAGAATGGCACATTCAAGAAGGGCGATATGTTTAACCTG

AATGACTGTCACAAGCTGATCGACTTCTTTAAGGATAGCATCTCCCGGTATCCAA

AGTGGTCCAATGCCTACGATTTCAACTTTTCTGAGACAGAGAAGTATAAGGACAT

CGCCGGCTTTTACAGAGAGGTGGAGGAGCAGGGCTATAAGGTGAGCTTCGAGT

CTGCCAGCAAGAAGGAGGTGGATAAGCTGGTGGAGGAGGGCAAGCTGTATATG

TTCCAGATCTATAACAAGGACTTTTCCGATAAGTCTCACGGCACACCCAATCTGC

ACACCATGTACTTCAAGCTGCTGTTTGACGAGAACAATCACGGACAGATCAGGC

TGAGCGGAGGAGCAGAGCTGTTCATGAGGCGCGCCTCCCTGAAGAAGGAGGAG

CTGGTGGTGCACCCAGCCAACTCCCCTATCGCCAACAAGAATCCAGATAATCCC

AAGAAAACCACAACCCTGTCCTACGACGTGTATAAGGATAAGAGGTTTTCTGAG

GACCAGTACGAGCTGCACATCCCAATCGCCATCAATAAGTGCCCCAAGAACATC

TTCAAGATCAATACAGAGGTGCGCGTGCTGCTGAAGCACGACGATAACCCCTAT

GTGATCGGCATCGCCAGGGGCGAGCGCAATCTGCTGTATATCGTGGTGGTGGAC

GGCAAGGGCAACATCGTGGAGCAGTATTCCCTGAACGAGATCATCAACAACTTC
```

-continued

```
AACGGCATCAGGATCAAGACAGATTACCACTCTCTGCTGGACAAGAAGGAGAA
GGAGAGGTTCGAGGCCCGCCAGAACTGGACCTCCATCGAGAATATCAAGGAGC
TGAAGGCCGGCTATATCTCTCAGGTGGTGCACAAGATCTGCGAGCTGGTGGAGA
AGTACGATGCCGTGATCGCCCTGGAGGACCTGAACTCTGGCTTTAAGAATAGCC
GCGTGAAGGTGGAGAAGCAGGTGTATCAGAAGTTCGAGAAGATGCTGATCGAT
AAGCTGAACTACATGGTGGACAAGAAGTCTAATCCTTGTGCAACAGGCGGCGCC
CTGAAGGGCTATCAGATCACCAATAAGTTCGAGAGCTTTAAGTCCATGTCTACCC
AGAACGGCTTCATCTTTTACATCCCTGCCTGGCTGACATCCAAGATCGATCCATC
TACCGGCTTTGTGAACCTGCTGAAAACCAAGTATACCAGCATCGCCGATTCCAA
GAAGTTCATCAGCTCCTTTGACAGGATCATGTACGTGCCCGAGGAGGATCTGTT
CGAGTTTGCCCTGGACTATAAGAACTTCTCTCGCACAGACGCCGATTACATCAA
GAAGTGGAAGCTGTACTCCTACGGCAACCGGATCAGAATCTTCCGGAATCCTAA
GAAGAACAACGTGTTCGACTGGGAGGAGGTGTGCCTGACCAGCGCCTATAAGG
AGCTGTTCAACAAGTACGGCATCAATTATCAGCAGGGCGATATCAGAGCCCTGC
TGTGCGAGCAGTCCGACAAGGCCTTCTACTCTAGCTTTATGGCCCTGATGAGCCT
GATGCTGCAGATGCGGAACAGCATCACAGGCCGCACCGACGTGGATTTTCTGAT
CAGCCCTGTGAAGAACTCCGACGGCATCTTCTACGATAGCCGGAACTATGAGGC
CCAGGAGAATGCCATCCTGCCAAAGAACGCCGACGCCAATGGCGCCTATAACA
TCGCCAGAAAGGTGCTGTGGGCCATCGGCCAGTTCAAGAAGGCCGAGGACGAG
AAGCTGGATAAGGTGAAGATCGCCATCTCTAACAAGGAGTGGCTGGAGTACGCC
CAGACCAGCGTGAAGCACAAAAGGCCGGCGGCCACGAAAAAGGCCGGCCAGGC
AAAAAAGAAAAAGGGATCCtacccatacgatgttccagattacgcttatccctacgacgtgcctgattatgcata
cccatatgatgtccccgactatgccTAA
```

2. BPK1169: CAG-DmrC-NLS-FLAG-P65

DmrC: bold, NLS-Flag: italic, P65: lower case (SEQ ID NO: 49)

```
ATGGGATCCAGAATCCTCTGGCATGAGATGTGGCATGAAGGCCTGGAAGAGGC
ATCTCGTTTGTACTTTGGGGAAAGGAACGTGAAAGGCATGTTTGAGGTGCTGGA
GCCCTTGCATGCTATGATGGAACGGGACCCCAGACTCTGAAGGAAACATCCTT
TAATCAGGCCTATGGTCGAGATTTAATGGAGGCCCAAGAGTGGTGCAGGAAGTA
CATGAAATCAGGGAATGTCAAGGACCTCCTCCAAGCCTGGGACCTCTATTATCA
TGTGTTCCGACGAATCTCAAAGGCGGCGGATCCCCCAAGAAGAAGAGGAAAGT
CTCGAGCGACTACAAAGACCATGACGGTGATTATAAAGATCATGACATCGATTACA
AGGATGACGATGACAAGGCTGCAGGAGGCGGTGGAAGCGGGatggagttccagtacctgc
cagatacagacgatcgtcaccggattgaggagaaacgtaaaaggacatatgagaccttcaagagcatcatgaagaag
agtcctttcagcggacccaccgaccccggcctccacctcgacgcattgctgtgccttcccgcagctcagcttctgtcccca
agccagcacccagccctatccctttacgtcatccctgagcaccatcaactatgatgagtttccaccatggtgtttccttctg
ggcagatcagccaggcctcggccttggccccggcccctcccaagtcctgccccaggctccagccctgccctgctcc
agccatggtatcagctctggcccaggcccagcccctgtcccagtcctagccccaggccctcctcaggctgtggccccac
ctgcccccaagcccaccccaggctggggaaggaacgctgtcagaggccctgctgcagctgcagtttgatgatgaagacc
```

-continued tgggggccttgcttggcaacagcacagacccagctgtgttcacagacctggcatccgtcgataactccgagtttcagcag ctgctgaaccagggcatacctgtggccccccacacaactgagcccatgctgatggagtaccctgaggctataactcgcct agtgacaggggcccagaggccccccgacccagctcctgctccactgggggccccggggctcccaatggcctcctttc aggagatgaagacttctcctccattgcggacatggacttctcagccctgctgagtcagatcagctctTAA

3. MMW948: CAG-DmrC-NLS-FLAG-VPR

DmrC: bold, NLS-Flag: italic, VPR: lowercase (SEQ ID NO: 50)

ATGGGATCCAGAATCCTCTGGCATGAGATGTGGCATGAAGGCCTGGAAGAGGC

ATCTCGTTTGTACTTTGGGGAAAGGAACGTGAAAGGCATGTTTGAGGTGCTGGA

GCCCTTGCATGCTATGATGGAACGGGGACCCCAGACTCTGAAGGAAACATCCTT

TAATCAGGCCTATGGTCGAGATTTAATGGAGGCCCAAGAGTGGTGCAGGAAGTA

CATGAAATCAGGGAATGTCAAGGACCTCCTCCAAGCCTGGGACCTCTATTATCA

TGTGTTCCGACGAATCTCAAAGGGCGGCGGATCCCCCAAGAAGAAGAGGAAAGT

*CTCGAGCGACTACAAAGACCATGACGGTGATTATAAAGATCATGACATCGATTACA*

*AGGATGACGATGACAAGGCTGCAGGAGGCGGTGGAAGCGGGTCG*gaggccagcggttc cggacgggctgacgcattggacgattttgatctggatatgctgggaagtgacgccctcgatgattttgaccttgacatgcttg gttcggatgcccttgatgactttgacctcgacatgctcggcagtgacgcccttgatgatttcgacctggacatgctgattaact ctagaagttccggatctccgaaaaagaaacgcaaagttggtagccagtacctgcccgacaccgacgaccggcaccgg atcgaggaaaagcggaagcggacctacgagacattcaagagcatcatgaagaagtccccccttcagcggccccaccg accctagacctccacctagaagaatcgccgtgcccagcagatccagcgccagcgtgccaaaacctgcccccagcctt acccccttcaccagcagcctgagcaccatcaactacgacgagttccctaccatggtgttccccagcggccagatctctcag gcctctgctctggctccagcccctcctcaggtgctgcctcaggctcctgctcctgcaccagctccagccatggtgtctgcact ggctcaggcaccagcacccgtgcctgtgctggctcctggacctccacaggctgtggctccaccagcccctaaacctaca caggccggcgagggcacactgtctgaagctctgctgcagctgcagttcgacgacgaggatctgggagccctgctggga aacagcaccgatcctgccgtgttcaccgacctggccagcgtggacaacagcgagttccagcagctgctgaaccagggc atccctgtggcccctcacaccaccgagcccatgctgatggaataccccgaggccatcacccggctcgtgacaggcgctc agaggcctcctgatccagctcctgcccctctgggagcaccaggcctgcctaatggactgctgtctggcgacgaggacttc agctctatcgccgatatggatttctcagccttgctgggctctggcagcggcagcggattccagggaagggatgttttttgcc gaagcctgaggccggctccgctattagtgacgtgtttgagggccgcgaggtgtgccagccaaaacgaatccggccatttc atcctccaggaagtccatgggccaaccgcccactccccgccagcctcgcaccaacaccaaccggtccagtacatgag ccagtcgggtcactgaccccggcaccagtccctcagccactggatccagcgcccgcagtgactcccgaggccagtcac ctgttggaggatcccgatgaagagacgagccaggctgtcaaagcccttcgggagatggccgatactgtgattccccaga aggaagaggctgcaatctgtgccaaatggacctttcccatccgccccaaggggccatctggatgagctgacaacca cacttgagtccatgaccgaggatctgaacctggactcacccctgaccccggaattgaacgagattctggataccttcctga acgacgagtgcctcttgcatgccatgcatatcagcacaggactgtccatcttcgacacatctctgTTT 4. JG1202: CAG-human dLbCpf1(D832A)-NLS-3×HA-P65

```
Human codon optimized dLbCpf1: bold, NLS: italic, 3xHA: lower case, P65:
lower case and bold
                                                        (SEQ ID NO: 51)
ATGAGCAAGCTGGAGAAGTTTACAAACTGCTACTCCCTGTCTAAGACCCTGAGG

TTCAAGGCCATCCCTGTGGGCAAGACCCAGGAGAACATCGACAATAAGCGGCT

GCTGGTGGAGGACGAGAAGAGAGCCGAGGATTATAAGGGCGTGAAGAAGCTGC

TGGATCGCTACTATCTGTCTTTTATCAACGACGTGCTGCACAGCATCAAGCTGAA

GAATCTGAACAATTACATCAGCCTGTTCCGGAAGAAAACCAGAACCGAGAAGGA

GAATAAGGAGCTGGAGAACCTGGAGATCAATCTGCGGAAGGAGATCGCCAAGG

CCTTCAAGGGCAACGAGGGCTACAAGTCCCTGTTTAAGAAGGATATCATCGAGA

CAATCCTGCCAGAGTTCCTGGACGATAAGGACGAGATCGCCCTGGTGAACAGCT

TCAATGGCTTTACCACAGCCTTCACCGGCTTCTTTGATAACAGAGAGAATATGTT

TTCCGAGGAGGCCAAGAGCACATCCATCGCCTTCAGGTGTATCAACGAGAATCT

GACCCGCTACATCTCTAATATGGACATCTTCGAGAAGGTGGACGCCATCTTTGAT

AAGCACGAGGTGCAGGAGATCAAGGAGAAGATCCTGAACAGCGACTATGATGT

GGAGGATTTCTTTGAGGGCGAGTTCTTTAACTTTGTGCTGACACAGGAGGGCATC

GACGTGTATAACGCCATCATCGGCGGCTTCGTGACCGAGAGCGGCGAGAAGAT

CAAGGGCCTGAACGAGTACATCAACCTGTATAATCAGAAAACCAAGCAGAAGCT

GCCTAAGTTTAAGCCACTGTATAAGCAGGTGCTGAGCGATCGGGAGTCTCTGAG

CTTCTACGGCGAGGGCTATACATCCGATGAGGAGGTGCTGGAGGTGTTTAGAAA

CACCCTGAACAAGAACAGCGAGATCTTCAGCTCCATCAAGAAGCTGGAGAAGCT

GTTCAAGAATTTTGACGAGTACTCTAGCGCCGGCATCTTTGTGAAGAACGGCCC

CGCCATCAGCACAATCTCCAAGGATATCTTCGGCGAGTGGAACGTGATCCGGGA

CAAGTGGAATGCCGAGTATGACGATATCCACCTGAAGAAGAAGGCCGTGGTGA

CCGAGAAGTACGAGGACGATCGGAGAAAGTCCTTCAAGAAGATCGGCTCCTTTT

CTCTGGAGCAGCTGCAGGAGTACGCCGACGCCGATCTGTCTGTGGTGGAGAAG

CTGAAGGAGATCATCATCCAGAAGGTGGATGAGATCTACAAGGTGTATGGCTCC

TCTGAGAAGCTGTTCGACGCCGATTTTGTGCTGGAGAAGAGCCTGAAGAAGAAC

GACGCCGTGGTGGCCATCATGAAGGACCTGCTGGATTCTGTGAAGAGCTTCGAG

AATTACATCAAGGCCTTCTTTGGCGAGGGCAAGGAGACAAACAGGGACGAGTC

CTTCTATGGCGATTTTGTGCTGGCCTACGACATCCTGCTGAAGGTGGACCACATC

TACGATGCCATCCGCAATTATGTGACCCAGAAGCCCTACTCTAAGGATAAGTTCA

AGCTGTATTTTCAGAACCCTCAGTTCATGGGCGGCTGGGACAAGGATAAGGAGA

CAGACTATCGGGCCACCATCCTGAGATACGGCTCCAAGTACTATCTGGCCATCA

TGGATAAGAAGTACGCCAAGTGCCTGCAGAAGATCGACAAGGACGATGTGAAC

GGCAATTACGAGAAGATCAACTATAAGCTGCTGCCCGGCCCTAATAAGATGCTG

CCAAAGGTGTTCTTTTCTAAGAAGTGGATGGCCTACTATAACCCCAGCGAGGAC

ATCCAGAAGATCTACAAGAATGGCACATTCAAGAAGGGCGATATGTTTAACCTG

AATGACTGTCACAAGCTGATCGACTTCTTTAAGGATAGCATCTCCCGGTATCCAA

AGTGGTCCAATGCCTACGATTTCAACTTTTCTGAGACAGAGAAGTATAAGGACAT

CGCCGGCTTTTACAGAGAGGTGGAGGAGCAGGGCTATAAGGTGAGCTTCGAGT
```

-continued

CTGCCAGCAAGAAGGAGGTGGATAAGCTGGTGGAGGAGGGCAAGCTGTATATG
TTCCAGATCTATAACAAGGACTTTTCCGATAAGTCTCACGGCACACCCAATCTGC
ACACCATGTACTTCAAGCTGCTGTTTGACGAGAACAATCACGGACAGATCAGGC
TGAGCGGAGGAGCAGAGCTGTTCATGAGGCGCGCCTCCCTGAAGAAGGAGGAG
CTGGTGGTGCACCCAGCCAACTCCCCTATCGCCAACAAGAATCCAGATAATCCC
AAGAAAACCACAACCCTGTCCTACGACGTGTATAAGGATAAGAGGTTTTCTGAG
GACCAGTACGAGCTGCACATCCCAATCGCCATCAATAAGTGCCCCAAGAACATC
TTCAAGATCAATACAGAGGTGCGCGTGCTGCTGAAGCACGACGATAACCCCTAT
GTGATCGGCATCGCCAGGGGCGAGCGCAATCTGCTGTATATCGTGGTGGTGGAC
GGCAAGGGCAACATCGTGGAGCAGTATTCCCTGAACGAGATCATCAACAACTTC
AACGGCATCAGGATCAAGACAGATTACCACTCTCTGCTGGACAAGAAGGAGAA
GGAGAGGTTCGAGGCCCGCCAGAACTGGACCTCCATCGAGAATATCAAGGAGC
TGAAGGCCGGCTATATCTCTCAGGTGGTGCACAAGATCTGCGAGCTGGTGGAGA
AGTACGATGCCGTGATCGCCCTGGAGGACCTGAACTCTGGCTTTAAGAATAGCC
GCGTGAAGGTGGAGAAGCAGGTGTATCAGAAGTTCGAGAAGATGCTGATCGAT
AAGCTGAACTACATGGTGGACAAGAAGTCTAATCCTTGTGCAACAGGCGGCGCC
CTGAAGGGCTATCAGATCACCAATAAGTTCGAGAGCTTTAAGTCCATGTCTACCC
AGAACGGCTTCATCTTTTACATCCCTGCCTGGCTGACATCCAAGATCGATCCATC
TACCGGCTTTGTGAACCTGCTGAAAACCAAGTATACCAGCATCGCCGATTCCAA
GAAGTTCATCAGCTCCTTTGACAGGATCATGTACGTGCCCGAGGAGGATCTGTT
CGAGTTTGCCCTGGACTATAAGAACTTCTCTCGCACAGACGCCGATTACATCAA
GAAGTGGAAGCTGTACTCCTACGGCAACCGGATCAGAATCTTCCGGAATCCTAA
GAAGAACAACGTGTTCGACTGGGAGGAGGTGTGCCTGACCAGCGCCTATAAGG
AGCTGTTCAACAAGTACGGCATCAATTATCAGCAGGGCGATATCAGAGCCCTGC
TGTGCGAGCAGTCCGACAAGGCCTTCTACTCTAGCTTTATGGCCCTGATGAGCCT
GATGCTGCAGATGCGGAACAGCATCACAGGCCGCACCGACGTGGATTTTCTGAT
CAGCCCTGTGAAGAACTCCGACGGCATCTTCTACGATAGCCGGAACTATGAGGC
CCAGGAGAATGCCATCCTGCCAAAGAACGCCGACGCCAATGGCGCCTATAACA
TCGCCAGAAAGGTGCTGTGGGCCATCGGCCAGTTCAAGAAGGCCGAGGACGAG
AAGCTGGATAAGGTGAAGATCGCCATCTCTAACAAGGAGTGGCTGGAGTACGCC
CAGACCAGCGTGAAGCAC*AAAAGGCCGGCGGCCACGAAAAAGGCCGGCCAGGC
AAAAAAGAAAAAGGGATCC*tacccatacgatgttccagattacgcttatccctacgacgtgcctgattatgcata
cccatatgatgtccccgactatgccGGAAGCatggagttccagtacctgccagatacagacgatcgtcaccgga
ttgaggagaaacgtaaaaggacatatgagaccttcaagagcatcatgaagaagagtcctttcagcggacccac
cgacccccggcctccacctcgacgcattgctgtgccttcccgcagctcagcttctgtccccaagccagcaccc
cagccctatcccttttacgtcatccctgagcaccatcaactatgatgagtttcccaccatggtgtttccttctgggca
gatcagccaggcctcggccttggcccggcccctccccaagtcctgcccaggctccagccctgccctgc
tccagccatggtatcagctctggcccaggcccagccctgtcccagtcctagccccaggccctcctcaggct
gtggccccacctgcccccaagcccacccaggctggggaaggaacgctgtcagaggccctgctgcagctgc
agtttgatgatgaagacctgggggccttgcttggcaacagcacagacccagctgtgttcacagacctggcatcc -continued

```
gtcgataactccgagtttcagcagctgctgaaccagggcatacctgtggcccccacacaactgagcccatgc tgatggagtaccctgaggctataactcgcctagtgacaggggcccagaggccccccgacccagctcctgctc cactgggggccccggggctccccaatggcctcctttcaggagatgaagacttctcctccattgcggacatgga cttctcagccctgctgagtcagatcagctctTAA
```

5. JG1211: CAG-human dLbCpf1(D832A)-NLS-3×HA-VPR

```
Human codon optimized dLbCpf1: bold, NLS: italic, 3xHA: lower case, VPR:
lower case and bold
                                                              (SEQ ID NO: 52)
ATGAGCAAGCTGGAGAAGTTTACAAACTGCTACTCCCTGTCTAAGACCCTGAGG

TTCAAGGCCATCCCTGTGGGCAAGACCCAGGAGAACATCGACAATAAGCGGCT

GCTGGTGGAGGACGAGAAGAGAGCCGAGGATTATAAGGGCGTGAAGAAGCTGC

TGGATCGCTACTATCTGTCTTTTATCAACGACGTGCTGCACAGCATCAAGCTGAA

GAATCTGAACAATTACATCAGCCTGTTCCGGAAGAAAACCAGAACCGAGAAGGA

GAATAAGGAGCTGGAGAACCTGGAGATCAATCTGCGGAAGGAGATCGCCAAGG

CCTTCAAGGGCAACGAGGGCTACAAGTCCCTGTTTAAGAAGGATATCATCGAGA

CAATCCTGCCAGAGTTCCTGGACGATAAGGACGAGATCGCCCTGGTGAACAGCT

TCAATGGCTTTACCACAGCCTTCACCGGCTTCTTTGATAACAGAGAGAATATGTT

TTCCGAGGAGGCCAAGAGCACATCCATCGCCTTCAGGTGTATCAACGAGAATCT

GACCCGCTACATCTCTAATATGGACATCTTCGAGAAGGTGGACGCCATCTTTGAT

AAGCACGAGGTGCAGGAGATCAAGGAGAAGATCCTGAACAGCGACTATGATGT

GGAGGATTTCTTTGAGGGCGAGTTCTTTAACTTTGTGCTGACACAGGAGGGCATC

GACGTGTATAACGCCATCATCGGCGGCTTCGTGACCGAGAGCGGCGAGAAGAT

CAAGGGCCTGAACGAGTACATCAACCTGTATAATCAGAAAACCAAGCAGAAGCT

GCCTAAGTTTAAGCCACTGTATAAGCAGGTGCTGAGCGATCGGGAGTCTCTGAG

CTTCTACGGCGAGGGCTATACATCCGATGAGGAGGTGCTGGAGGTGTTTAGAAA

CACCCTGAACAAGAACAGCGAGATCTTCAGCTCCATCAAGAAGCTGGAGAAGCT

GTTCAAGAATTTTGACGAGTACTCTAGCGCCGGCATCTTTGTGAAGAACGGCCC

CGCCATCAGCACAATCTCCAAGGATATCTTCGGCGAGTGGAACGTGATCCGGGA

CAAGTGGAATGCCGAGTATGACGATATCCACCTGAAGAAGAAGGCCGTGGTGA

CCGAGAAGTACGAGGACGATCGGAGAAAGTCCTTCAAGAAGATCGGCTCCTTTT

CTCTGGAGCAGCTGCAGGAGTACGCCGACGCCGATCTGTCTGTGGTGGAGAAG

CTGAAGGAGATCATCATCCAGAAGGTGGATGAGATCTACAAGGTGTATGGCTCC

TCTGAGAAGCTGTTCGACGCCGATTTTGTGCTGGAGAAGAGCCTGAAGAAGAAC

GACGCCGTGGTGGCCATCATGAAGGACCTGCTGGATTCTGTGAAGAGCTTCGAG

AATTACATCAAGGCCTTCTTTGGCGAGGGCAAGGAGACAAACAGGGACGAGTC

CTTCTATGGCGATTTTGTGCTGGCCTACGACATCCTGCTGAAGGTGGACCACATC

TACGATGCCATCCGCAATTATGTGACCCAGAAGCCCTACTCTAAGGATAAGTTCA

AGCTGTATTTTCAGAACCCTCAGTTCATGGGCGGCTGGGACAAGGATAAGGAGA

CAGACTATCGGGCCACCATCCTGAGATACGGCTCCAAGTACTATCTGGCCATCA

TGGATAAGAAGTACGCCAAGTGCCTGCAGAAGATCGACAAGGACGATGTGAAC
```

```
GGCAATTACGAGAAGATCAACTATAAGCTGCTGCCCGGCCCTAATAAGATGCTG

CCAAAGGTGTTCTTTTCTAAGAAGTGGATGGCCTACTATAACCCCAGCGAGGAC

ATCCAGAAGATCTACAAGAATGGCACATTCAAGAAGGGCGATATGTTTAACCTG

AATGACTGTCACAAGCTGATCGACTTCTTTAAGGATAGCATCTCCCGGTATCCAA

AGTGGTCCAATGCCTACGATTTCAACTTTTCTGAGACAGAGAAGTATAAGGACAT

CGCCGGCTTTTACAGAGAGGTGGAGGAGCAGGGCTATAAGGTGAGCTTCGAGT

CTGCCAGCAAGAAGGAGGTGGATAAGCTGGTGGAGGAGGGCAAGCTGTATATG

TTCCAGATCTATAACAAGGACTTTTCCGATAAGTCTCACGGCACACCCAATCTGC

ACACCATGTACTTCAAGCTGCTGTTTGACGAGAACAATCACGGACAGATCAGGC

TGAGCGGAGGAGCAGAGCTGTTCATGAGGCGCGCCTCCCTGAAGAAGGAGGAG

CTGGTGGTGCACCCAGCCAACTCCCCTATCGCCAACAAGAATCCAGATAATCCC

AAGAAAACCACAACCCTGTCCTACGACGTGTATAAGGATAAGAGGTTTTCTGAG

GACCAGTACGAGCTGCACATCCCAATCGCCATCAATAAGTGCCCCAAGAACATC

TTCAAGATCAATACAGAGGTGCGCGTGCTGCTGAAGCACGACGATAACCCCTAT

GTGATCGGCATCGCCAGGGGCGAGCGCAATCTGCTGTATATCGTGGTGGTGGAC

GGCAAGGGCAACATCGTGGAGCAGTATTCCCTGAACGAGATCATCAACAACTTC

AACGGCATCAGGATCAAGACAGATTACCACTCTCTGCTGGACAAGAAGGAGAA

GGAGAGGTTCGAGGCCCGCCAGAACTGGACCTCCATCGAGAATATCAAGGAGC

TGAAGGCCGGCTATATCTCTCAGGTGGTGCACAAGATCTGCGAGCTGGTGGAGA

AGTACGATGCCGTGATCGCCCTGGAGGACCTGAACTCTGGCTTTAAGAATAGCC

GCGTGAAGGTGGAGAAGCAGGTGTATCAGAAGTTCGAGAAGATGCTGATCGAT

AAGCTGAACTACATGGTGGACAAGAAGTCTAATCCTTGTGCAACAGGCGGCGCC

CTGAAGGGCTATCAGATCACCAATAAGTTCGAGAGCTTTAAGTCCATGTCTACCC

AGAACGGCTTCATCTTTTACATCCCTGCCTGGCTGACATCCAAGATCGATCCATC

TACCGGCTTTGTGAACCTGCTGAAAACCAAGTATACCAGCATCGCCGATTCCAA

GAAGTTCATCAGCTCCTTTGACAGGATCATGTACGTGCCCGAGGAGGATCTGTT

CGAGTTTGCCCTGGACTATAAGAACTTCTCTCGCACAGACGCCGATTACATCAA

GAAGTGGAAGCTGTACTCCTACGGCAACCGGATCAGAATCTTCCGGAATCCTAA

GAAGAACAACGTGTTCGACTGGGAGGAGGTGTGCCTGACCAGCGCCTATAAGG

AGCTGTTCAACAAGTACGGCATCAATTATCAGCAGGGCGATATCAGAGCCCTGC

TGTGCGAGCAGTCCGACAAGGCCTTCTACTCTAGCTTTATGGCCCTGATGAGCCT

GATGCTGCAGATGCGGAACAGCATCACAGGCCGCACCGACGTGGATTTTCTGAT

CAGCCCTGTGAAGAACTCCGACGGCATCTTCTACGATAGCCGGAACTATGAGGC

CCAGGAGAATGCCATCCTGCCAAAGAACGCCGACGCCAATGGCGCCTATAACA

TCGCCAGAAAGGTGCTGTGGGCCATCGGCCAGTTCAAGAAGGCCGAGGACGAG

AAGCTGGATAAGGTGAAGATCGCCATCTCTAACAAGGAGTGGCTGGAGTACGCC

CAGACCAGCGTGAAGCAC*AAAAGGCCGGCGGCCACGAAAAAGGCCGGCCAGGC*

*AAAAAAGAAAAAGGGATCC*tacccatacgatgttccagattacgcttatccctacgacgtgcctgattatgcata cccatatgatgtccccgactatgccGGAAGCgaggccagcggttccggacgggctgacgcattggacgatttt gatctggatatgctgggaagtgacgccctcgatgattttgaccttgacatgcttggttcggatgcccttgatgactttt gacctcgacatgctcggcagtgacgcccttgatgatttcgacctggacatgctgattaactctagaagttccggat
```

-continued

```
ctccgaaaaagaaacgcaaagttggtagccagtacctgcccgacaccgacgaccggcaccggatcgagga
aaagcggaagcggacctacgagacattcaagagcatcatgaagaagtccccttcagcggccccaccgacc
ctagacctccacctagaagaatcgccgtgcccagcagatccagcgccagcgtgccaaaacctgcccccag
ccttacccttcaccagcagcctgagcaccatcaactacgacgagttccctaccatggtgttccccagcggcca
gatctctcaggcctctgctctggctccagcccctcctcaggtgctgcctcaggctcctgctcctgcaccagctcc
agccatggtgtctgcactggctcaggcaccagcacccgtgcctgtgctggctcctggacctccacaggctgtg
gctccaccagcccctaaacctacacaggccggcgagggcacactgtctgaagctctgctgcagctgcagttc
gacgacgaggatctgggagccctgctgggaaacagcaccgatcctgccgtgttcaccgacctggccagcgt
ggacaacagcgagttccagcagctgctgaaccagggcatccctgtggcccctcacaccaccgagcccatgct
gatggaataccccgaggccatcacccggctcgtgacaggcgctcagaggcctcctgatccagctcctgcccc
tctgggagcaccaggcctgcctaatggactgctgtctggcgacgaggacttcagctctatcgccgatatggattt
ctcagccttgctgggctctggcagcggcagccgggattccagggaagggatgttttttgccgaagcctgaggcc
ggctccgctattagtgacgtgtttgagggccgcgaggtgtgccagccaaaacgaatccggccatttcatcctcc
aggaagtccatgggccaaccgcccactccccgccagcctcgccaacaccaaccggtccagtacatgagc
cagtcgggtcactgaccccggcaccagtccctcagccactggatccagcgcccgcagtgactcccgaggcc
agtcacctgttggaggatcccgatgaagagacgagccaggctgtcaaagcccttcggggagatggccgatact
gtgattccccagaaggaagaggctgcaatctgtggccaaatggacctttcccatccgcccccaagggggccatc
tggatgagctgacaaccacacttgagtccatgaccgaggatctgaacctggactcacccctgaccccggaatt
gaacgagattctggataccttcctgaacgacgagtgcctcttgcatgccatgcatatcagcacaggactgtccat
cttcgacacatctctgTTT
```

6. JG674: CAG-human dLbCpf1(D832A)-NLS-3×HA-DmrA(X1)[35]

Human codon optimized dLbCpf1: bold, NLS: italic, 3xHA: lowercase, DmrA: lowercase and bold (SEQ ID NO: 53)

```
ATGAGCAAGCTGGAGAAGTTTACAAACTGCTACTCCCTGTCTAAGACCCTGAGG
TTCAAGGCCATCCCTGTGGGCAAGACCCAGGAGAACATCGACAATAAGCGGCT
GCTGGTGGAGGACGAGAAGAGAGCCGAGGATTATAAGGGCGTGAAGAAGCTGC
TGGATCGCTACTATCTGTCTTTTATCAACGACGTGCTGCACAGCATCAAGCTGAA
GAATCTGAACAATTACATCAGCCTGTTCCGGAAGAAAACCAGAACCGAGAAGGA
GAATAAGGAGCTGGAGAACCTGGAGATCAATCTGCGGAAGGAGATCGCCAAGG
CCTTCAAGGGCAACGAGGGCTACAAGTCCCTGTTTAAGAAGGATATCATCGAGA
CAATCCTGCCAGAGTTCCTGGACGATAAGGACGAGATCGCCCTGGTGAACAGCT
TCAATGGCTTTACCACAGCCTTCACCGGCTTCTTTGATAACAGAGAGAATATGTT
TTCCGAGGAGGCCAAGAGCACATCCATCGCCTTCAGGTGTATCAACGAGAATCT
GACCCGCTACATCTCTAATATGGACATCTTCGAGAAGGTGGACGCCATCTTTGAT
AAGCACGAGGTGCAGGAGATCAAGGAGAAGATCCTGAACAGCGACTATGATGT
GGAGGATTTCTTTGAGGGCGAGTTCTTTAACTTTGTGCTGACACAGGAGGGCATC
GACGTGTATAACGCCATCATCGGCGGCTTCGTGACCGAGAGCGGCGAGAAGAT
CAAGGGCCTGAACGAGTACATCAACCTGTATAATCAGAAAACCAAGCAGAAGCT
GCCTAAGTTTAAGCCACTGTATAAGCAGGTGCTGAGCGATCGGGAGTCTCTGAG
```

-continued

```
CTTCTACGGCGAGGGCTATACATCCGATGAGGAGGTGCTGGAGGTGTTTAGAAA
CACCCTGAACAAGAACAGCGAGATCTTCAGCTCCATCAAGAAGCTGGAGAAGCT
GTTCAAGAATTTTGACGAGTACTCTAGCGCCGGCATCTTTGTGAAGAACGGCCC
CGCCATCAGCACAATCTCCAAGGATATCTTCGGCGAGTGGAACGTGATCCGGGA
CAAGTGGAATGCCGAGTATGACGATATCCACCTGAAGAAGAAGGCCGTGGTGA
CCGAGAAGTACGAGGACGATCGGAGAAAGTCCTTCAAGAAGATCGGCTCCTTTT
CTCTGGAGCAGCTGCAGGAGTACGCCGACGCCGATCTGTCTGTGGTGGAGAAG
CTGAAGGAGATCATCATCCAGAAGGTGGATGAGATCTACAAGGTGTATGGCTCC
TCTGAGAAGCTGTTCGACGCCGATTTTGTGCTGGAGAAGAGCCTGAAGAAGAAC
GACGCCGTGGTGGCCATCATGAAGGACCTGCTGGATTCTGTGAAGAGCTTCGAG
AATTACATCAAGGCCTTCTTTGGCGAGGGCAAGGAGACAAACAGGGACGAGTC
CTTCTATGGCGATTTTGTGCTGGCCTACGACATCCTGCTGAAGGTGGACCACATC
TACGATGCCATCCGCAATTATGTGACCCAGAAGCCCTACTCTAAGGATAAGTTCA
AGCTGTATTTTCAGAACCCTCAGTTCATGGGCGGCTGGGACAAGGATAAGGAGA
CAGACTATCGGGCCACCATCCTGAGATACGGCTCCAAGTACTATCTGGCCATCA
TGGATAAGAAGTACGCCAAGTGCCTGCAGAAGATCGACAAGGACGATGTGAAC
GGCAATTACGAGAAGATCAACTATAAGCTGCTGCCCGGCCCTAATAAGATGCTG
CCAAAGGTGTTCTTTTCTAAGAAGTGGATGGCCTACTATAACCCCAGCGAGGAC
ATCCAGAAGATCTACAAGAATGGCACATTCAAGAAGGGCGATATGTTTAACCTG
AATGACTGTCACAAGCTGATCGACTTCTTTAAGGATAGCATCTCCCGGTATCCAA
AGTGGTCCAATGCCTACGATTTCAACTTTTCTGAGACAGAGAAGTATAAGGACAT
CGCCGGCTTTTACAGAGAGGTGGAGGAGCAGGGCTATAAGGTGAGCTTCGAGT
CTGCCAGCAAGAAGGAGGTGGATAAGCTGGTGGAGGAGGGCAAGCTGTATATG
TTCCAGATCTATAACAAGGACTTTTCCGATAAGTCTCACGGCACACCCAATCTGC
ACACCATGTACTTCAAGCTGCTGTTTGACGAGAACAATCACGGACAGATCAGGC
TGAGCGGAGGAGCAGAGCTGTTCATGAGGCGCGCCTCCCTGAAGAAGGAGGAG
CTGGTGGTGCACCCAGCCAACTCCCCTATCGCCAACAAGAATCCAGATAATCCC
AAGAAAACCACAACCCTGTCCTACGACGTGTATAAGGATAAGAGGTTTTCTGAG
GACCAGTACGAGCTGCACATCCCAATCGCCATCAATAAGTGCCCCAAGAACATC
TTCAAGATCAATACAGAGGTGCGCGTGCTGCTGAAGCACGACGATAACCCCTAT
GTGATCGGCATCGCCAGGGGCGAGCGCAATCTGCTGTATATCGTGGTGGTGGAC
GGCAAGGGCAACATCGTGGAGCAGTATTCCCTGAACGAGATCATCAACAACTTC
AACGGCATCAGGATCAAGACAGATTACCACTCTCTGCTGGACAAGAAGGAGAA
GGAGAGGTTCGAGGCCCGCCAGAACTGGACCTCCATCGAGAATATCAAGGAGC
TGAAGGCCGGCTATATCTCTCAGGTGGTGCACAAGATCTGCGAGCTGGTGGAGA
AGTACGATGCCGTGATCGCCCTGGAGGACCTGAACTCTGGCTTTAAGAATAGCC
GCGTGAAGGTGGAGAAGCAGGTGTATCAGAAGTTCGAGAAGATGCTGATCGAT
AAGCTGAACTACATGGTGGACAAGAAGTCTAATCCTTGTGCAACAGGCGGCGCC
CTGAAGGGCTATCAGATCACCAATAAGTTCGAGAGCTTTAAGTCCATGTCTACCC
AGAACGGCTTCATCTTTTACATCCCTGCCTGGCTGACATCCAAGATCGATCCATC
```

-continued

```
TACCGGCTTTGTGAACCTGCTGAAAACCAAGTATACCAGCATCGCCGATTCCAA

GAAGTTCATCAGCTCCTTTGACAGGATCATGTACGTGCCCGAGGAGGATCTGTT

CGAGTTTGCCCTGGACTATAAGAACTTCTCTCGCACAGACGCCGATTACATCAA

GAAGTGGAAGCTGTACTCCTACGGCAACCGGATCAGAATCTTCCGGAATCCTAA

GAAGAACAACGTGTTCGACTGGGAGGAGGTGTGCCTGACCAGCGCCTATAAGG

AGCTGTTCAACAAGTACGGCATCAATTATCAGCAGGGCGATATCAGAGCCCTGC

TGTGCGAGCAGTCCGACAAGGCCTTCTACTCTAGCTTTATGGCCCTGATGAGCCT

GATGCTGCAGATGCGGAACAGCATCACAGGCCGCACCGACGTGGATTTTCTGAT

CAGCCCTGTGAAGAACTCCGACGGCATCTTCTACGATAGCCGGAACTATGAGGC

CCAGGAGAATGCCATCCTGCCAAAGAACGCCGACGCCAATGGCGCCTATAACA

TCGCCAGAAAGGTGCTGTGGGCCATCGGCCAGTTCAAGAAGGCCGAGGACGAG

AAGCTGGATAAGGTGAAGATCGCCATCTCTAACAAGGAGTGGCTGGAGTACGCC

CAGACCAGCGTGAAGCAC```*AAAAGGCCGGCGGCCACGAAAAAGGCCGGCCAGGC*

*AAAAAAGAAAAAGGGATCC*tacccatacgatgttccagattacgcttatccctacgacgtgcctgattatgcata cccatatgatgtccccgactatgcc```TCGAGCGACTACAAAGACCATGACGGTGATTATAAAGAT

CATGACATCGATTACAAGGATGACGATGACAAGGCTGCAGGAGGCGGTGGAAGC

GGG```agggagtgcaggtggaaaccatctccccaggagacgggcgcaccttccccaagcgcggccagac ctgcgtggtgcactacaccgggatgcttgaagatggaaagaaatttgattcctcccgggacagaaacaagccc tttaagtttatgctaggcaagcaggaggtgatccgaggctgggaagaagggggttgcccagatgagtgtgggtc agagagccaaactgactatatctccagattatgcctatggtgccactgggcacccaggcatcatcccaccacat gccactctcgtcttcgatgtggagcttctaaaactggaa```GGATAA
```
35

7. JG676: CAG-human dLbCpf1(D832A)-NLS-3×HA-DmrA(X2)

Human codon optimized dLbCpf1: bold, NLS: italic, 3xHA: lowercase, DmrA: lowercase and bold (SEQ ID NO: 54)

```
ATGAGCAAGCTGGAGAAGTTTACAAACTGCTACTCCCTGTCTAAGACCCTGAGG

TTCAAGGCCATCCCTGTGGGCAAGACCCAGGAGAACATCGACAATAAGCGGCT

GCTGGTGGAGGACGAGAAGAGAGCCGAGGATTATAAGGGCGTGAAGAAGCTGC

TGGATCGCTACTATCTGTCTTTTATCAACGACGTGCTGCACAGCATCAAGCTGAA

GAATCTGAACAATTACATCAGCCTGTTCCGGAAGAAAACCAGAACCGAGAAGGA

GAATAAGGAGCTGGAGAACCTGGAGATCAATCTGCGGAAGGAGATCGCCAAGG

CCTTCAAGGGCAACGAGGGCTACAAGTCCCTGTTTAAGAAGGATATCATCGAGA

CAATCCTGCCAGAGTTCCTGGACGATAAGGACGAGATCGCCCTGGTGAACAGCT

TCAATGGCTTTACCACAGCCTTCACCGGCTTCTTTGATAACAGAGAGAATATGTT

TTCCGAGGAGGCCAAGAGCACATCCATCGCCTTCAGGTGTATCAACGAGAATCT

GACCCGCTACATCTCTAATATGGACATCTTCGAGAAGGTGGACGCCATCTTTGAT

AAGCACGAGGTGCAGGAGATCAAGGAGAAGATCCTGAACAGCGACTATGATGT

GGAGGATTTCTTTGAGGGCGAGTTCTTTAACTTTGTGCTGACACAGGAGGGCATC

GACGTGTATAACGCCATCATCGGCGGCTTCGTGACCGAGAGCGGCGAGAAGAT

CAAGGGCCTGAACGAGTACATCAACCTGTATAATCAGAAAACCAAGCAGAAGCT
```

-continued

```
GCCTAAGTTTAAGCCACTGTATAAGCAGGTGCTGAGCGATCGGGAGTCTCTGAG

CTTCTACGGCGAGGGCTATACATCCGATGAGGAGGTGCTGGAGGTGTTTAGAAA

CACCCTGAACAAGAACAGCGAGATCTTCAGCTCCATCAAGAAGCTGGAGAAGCT

GTTCAAGAATTTTGACGAGTACTCTAGCGCCGGCATCTTTGTGAAGAACGGCCC

CGCCATCAGCACAATCTCCAAGGATATCTTCGGCGAGTGGAACGTGATCCGGGA

CAAGTGGAATGCCGAGTATGACGATATCCACCTGAAGAAGAAGGCCGTGGTGA

CCGAGAAGTACGAGGACGATCGGAGAAAGTCCTTCAAGAAGATCGGCTCCTTTT

CTCTGGAGCAGCTGCAGGAGTACGCCGACGCCGATCTGTCTGTGGTGGAGAAG

CTGAAGGAGATCATCATCCAGAAGGTGGATGAGATCTACAAGGTGTATGGCTCC

TCTGAGAAGCTGTTCGACGCCGATTTTGTGCTGGAGAAGAGCCTGAAGAAGAAC

GACGCCGTGGTGGCCATCATGAAGGACCTGCTGGATTCTGTGAAGAGCTTCGAG

AATTACATCAAGGCCTTCTTTGGCGAGGGCAAGGAGACAAACAGGGACGAGTC

CTTCTATGGCGATTTTGTGCTGGCCTACGACATCCTGCTGAAGGTGGACCACATC

TACGATGCCATCCGCAATTATGTGACCCAGAAGCCCTACTCTAAGGATAAGTTCA

AGCTGTATTTTCAGAACCCTCAGTTCATGGGCGGCTGGGACAAGGATAAGGAGA

CAGACTATCGGGCCACCATCCTGAGATACGGCTCCAAGTACTATCTGGCCATCA

TGGATAAGAAGTACGCCAAGTGCCTGCAGAAGATCGACAAGGACGATGTGAAC

GGCAATTACGAGAAGATCAACTATAAGCTGCTGCCCGGCCCTAATAAGATGCTG

CCAAAGGTGTTCTTTTCTAAGAAGTGGATGGCCTACTATAACCCCAGCGAGGAC

ATCCAGAAGATCTACAAGAATGGCACATTCAAGAAGGGCGATATGTTTAACCTG

AATGACTGTCACAAGCTGATCGACTTCTTTAAGGATAGCATCTCCCGGTATCCAA

AGTGGTCCAATGCCTACGATTTCAACTTTTCTGAGACAGAGAAGTATAAGGACAT

CGCCGGCTTTTACAGAGAGGTGGAGGAGCAGGGCTATAAGGTGAGCTTCGAGT

CTGCCAGCAAGAAGGAGGTGGATAAGCTGGTGGAGGAGGGCAAGCTGTATATG

TTCCAGATCTATAACAAGGACTTTTCCGATAAGTCTCACGGCACACCCAATCTGC

ACACCATGTACTTCAAGCTGCTGTTTGACGAGAACAATCACGGACAGATCAGGC

TGAGCGGAGGAGCAGAGCTGTTCATGAGGCGCGCCTCCCTGAAGAAGGAGGAG

CTGGTGGTGCACCCAGCCAACTCCCCTATCGCCAACAAGAATCCAGATAATCCC

AAGAAAACCACAACCCTGTCCTACGACGTGTATAAGGATAAGAGGTTTTCTGAG

GACCAGTACGAGCTGCACATCCCAATCGCCATCAATAAGTGCCCCAAGAACATC

TTCAAGATCAATACAGAGGTGCGCGTGCTGCTGAAGCACGACGATAACCCCTAT

GTGATCGGCATCGCCAGGGGCGAGCGCAATCTGCTGTATATCGTGGTGGTGGAC

GGCAAGGGCAACATCGTGGAGCAGTATTCCCTGAACGAGATCATCAACAACTTC

AACGGCATCAGGATCAAGACAGATTACCACTCTCTGCTGGACAAGAAGGAGAA

GGAGAGGTTCGAGGCCCGCCAGAACTGGACCTCCATCGAGAATATCAAGGAGC

TGAAGGCCGGCTATATCTCTCAGGTGGTGCACAAGATCTGCGAGCTGGTGGAGA

AGTACGATGCCGTGATCGCCCTGGAGGACCTGAACTCTGGCTTTAAGAATAGCC

GCGTGAAGGTGGAGAAGCAGGTGTATCAGAAGTTCGAGAAGATGCTGATCGAT

AAGCTGAACTACATGGTGGACAAGAAGTCTAATCCTTGTGCAACAGGCGGCGCC

CTGAAGGGCTATCAGATCACCAATAAGTTCGAGAGCTTTAAGTCCATGTCTACCC

AGAACGGCTTCATCTTTTACATCCCTGCCTGGCTGACATCCAAGATCGATCCATC
```

-continued

```
TACCGGCTTTGTGAACCTGCTGAAAACCAAGTATACCAGCATCGCCGATTCCAA
GAAGTTCATCAGCTCCTTTGACAGGATCATGTACGTGCCCGAGGAGGATCTGTT
CGAGTTTGCCCTGGACTATAAGAACTTCTCTCGCACAGACGCCGATTACATCAA
GAAGTGGAAGCTGTACTCCTACGGCAACCGGATCAGAATCTTCCGGAATCCTAA
GAAGAACAACGTGTTCGACTGGGAGGAGGTGTGCCTGACCAGCGCCTATAAGG
AGCTGTTCAACAAGTACGGCATCAATTATCAGCAGGGCGATATCAGAGCCCTGC
TGTGCGAGCAGTCCGACAAGGCCTTCTACTCTAGCTTTATGGCCCTGATGAGCCT
GATGCTGCAGATGCGGAACAGCATCACAGGCCGCACCGACGTGGATTTTCTGAT
CAGCCCTGTGAAGAACTCCGACGGCATCTTCTACGATAGCCGGAACTATGAGGC
CCAGGAGAATGCCATCCTGCCAAAGAACGCCGACGCCAATGGCGCCTATAACA
TCGCCAGAAAGGTGCTGTGGGCCATCGGCCAGTTCAAGAAGGCCGAGGACGAG
AAGCTGGATAAGGTGAAGATCGCCATCTCTAACAAGGAGTGGCTGGAGTACGCC
CAGACCAGCGTGAAGCACAAAAGGCCGGCGGCCACGAAAAAGGCCGGCCAGGC
AAAAAAGAAAAAGGGATCCtacccatacgatgttccagattacgcttatccctacgacgtgcctgattatgcata
cccatatgatgtccccgactatgccTCGAGCGACTACAAAGACCATGACGGTGATTATAAAGAT
CATGACATCGATTACAAGGATGACGATGACAAGGCTGCAGGAGGCGGTGGAAGC
GGGaggggagtgcaggtggaaaccatctccccaggagacgggcgcaccttccccaagcgcggccagac
ctgcgtggtgcactacaccgggatgcttgaagatggaaagaaatttgattcctcccgggacagaaacaagccc
tttaagtttatgctaggcaagcaggaggtgatccgaggctgggaagaaggggttgcccagatgagtgtgggtc
agagagccaaactgactatatctccagattatgcctatggtgccactgggcacccaggcatcatcccaccacat
gccactctcgtcttcgatgtggagcttctaaaactggaaGGTTCtagggagtgcaggtggaaaccatctccc
caggagacgggcgcaccttccccaagcgcggccagacctgcgtggtgcactacaccgggatgcttgaagat
ggaaagaaatttgattcctcccgggacagaaacaagcccttaagtttatgctaggcaagcaggaggtgatccg
aggctgggaagaaggggttgcccagatgagtgtgggtcagagagccaaactgactatatctccagattatgcc
tatggtgccactgggcacccaggcatcatcccaccacatgccactctcgtcttcgatgtggagcttctaaaactg
gaaGGATAA
```

8. JG693: CAG-human dLbCpf1(D832A)-NLS-3×HA-DmrA(X3)

Human codon optimized dLbCpf1: bold, NLS: italic, 3xHA: lowercase, DmrA: lowercase and bold (SEQ ID NO: 55)

```
ATGAGCAAGCTGGAGAAGTTTACAAACTGCTACTCCCTGTCTAAGACCCTGAGG
TTCAAGGCCATCCCTGTGGGCAAGACCCAGGAGAACATCGACAATAAGCGGCT
GCTGGTGGAGGACGAGAAGAGAGCCGAGGATTATAAGGGCGTGAAGAAGCTGC
TGGATCGCTACTATCTGTCTTTTATCAACGACGTGCTGCACAGCATCAAGCTGAA
GAATCTGAACAATTACATCAGCCTGTTCCGGAAGAAAACCAGAACCGAGAAGGA
GAATAAGGAGCTGGAGAACCTGGAGATCAATCTGCGGAAGGAGATCGCCAAGG
CCTTCAAGGGCAACGAGGGCTACAAGTCCCTGTTTAAGAAGGATATCATCGAGA
CAATCCTGCCAGAGTTCCTGGACGATAAGGACGAGATCGCCCTGGTGAACAGCT
TCAATGGCTTTACCACAGCCTTCACCGGCTTCTTTGATAACAGAGAGAATATGTT
TTCCGAGGAGGCCAAGAGCACATCCATCGCCTTCAGGTGTATCAACGAGAATCT
```

-continued

```
GACCCGCTACATCTCTAATATGGACATCTTCGAGAAGGTGGACGCCATCTTTGAT

AAGCACGAGGTGCAGGAGATCAAGGAGAAGATCCTGAACAGCGACTATGATGT

GGAGGATTTCTTTGAGGGCGAGTTCTTTAACTTTGTGCTGACACAGGAGGGCATC

GACGTGTATAACGCCATCATCGGCGGCTTCGTGACCGAGAGCGGCGAGAAGAT

CAAGGGCCTGAACGAGTACATCAACCTGTATAATCAGAAAACCAAGCAGAAGCT

GCCTAAGTTTAAGCCACTGTATAAGCAGGTGCTGAGCGATCGGGAGTCTCTGAG

CTTCTACGGCGAGGGCTATACATCCGATGAGGAGGTGCTGGAGGTGTTTAGAAA

CACCCTGAACAAGAACAGCGAGATCTTCAGCTCCATCAAGAAGCTGGAGAAGCT

GTTCAAGAATTTTGACGAGTACTCTAGCGCCGGCATCTTTGTGAAGAACGGCCC

CGCCATCAGCACAATCTCCAAGGATATCTTCGGCGAGTGGAACGTGATCCGGGA

CAAGTGGAATGCCGAGTATGACGATATCCACCTGAAGAAGAAGGCCGTGGTGA

CCGAGAAGTACGAGGACGATCGGAGAAAGTCCTTCAAGAAGATCGGCTCCTTTT

CTCTGGAGCAGCTGCAGGAGTACGCCGACGCCGATCTGTCTGTGGTGGAGAAG

CTGAAGGAGATCATCATCCAGAAGGTGGATGAGATCTACAAGGTGTATGGCTCC

TCTGAGAAGCTGTTCGACGCCGATTTTGTGCTGGAGAAGAGCCTGAAGAAGAAC

GACGCCGTGGTGGCCATCATGAAGGACCTGCTGGATTCTGTGAAGAGCTTCGAG

AATTACATCAAGGCCTTCTTTGGCGAGGGCAAGGAGACAAACAGGGACGAGTC

CTTCTATGGCGATTTTGTGCTGGCCTACGACATCCTGCTGAAGGTGGACCACATC

TACGATGCCATCCGCAATTATGTGACCCAGAAGCCCTACTCTAAGGATAAGTTCA

AGCTGTATTTTCAGAACCCTCAGTTCATGGGCGGCTGGGACAAGGATAAGGAGA

CAGACTATCGGGCCACCATCCTGAGATACGGCTCCAAGTACTATCTGGCCATCA

TGGATAAGAAGTACGCCAAGTGCCTGCAGAAGATCGACAAGGACGATGTGAAC

GGCAATTACGAGAAGATCAACTATAAGCTGCTGCCCGGCCCTAATAAGATGCTG

CCAAAGGTGTTCTTTTCTAAGAAGTGGATGGCCTACTATAACCCCAGCGAGGAC

ATCCAGAAGATCTACAAGAATGGCACATTCAAGAAGGGCGATATGTTTAACCTG

AATGACTGTCACAAGCTGATCGACTTCTTTAAGGATAGCATCTCCCGGTATCCAA

AGTGGTCCAATGCCTACGATTTCAACTTTTCTGAGACAGAGAAGTATAAGGACAT

CGCCGGCTTTTACAGAGAGGTGGAGGAGCAGGGCTATAAGGTGAGCTTCGAGT

CTGCCAGCAAGAAGGAGGTGGATAAGCTGGTGGAGGAGGGCAAGCTGTATATG

TTCCAGATCTATAACAAGGACTTTTCCGATAAGTCTCACGGCACACCCAATCTGC

ACACCATGTACTTCAAGCTGCTGTTTGACGAGAACAATCACGGACAGATCAGGC

TGAGCGGAGGAGCAGAGCTGTTCATGAGGCGCGCCTCCCTGAAGAAGGAGGAG

CTGGTGGTGCACCCAGCCAACTCCCCTATCGCCAACAAGAATCCAGATAATCCC

AAGAAAACCACAACCCTGTCCTACGACGTGTATAAGGATAAGAGGTTTTCTGAG

GACCAGTACGAGCTGCACATCCCAATCGCCATCAATAAGTGCCCCAAGAACATC

TTCAAGATCAATACAGAGGTGCGCGTGCTGCTGAAGCACGACGATAACCCCTAT

GTGATCGGCATCGCCAGGGGCGAGCGCAATCTGCTGTATATCGTGGTGGTGGAC

GGCAAGGGCAACATCGTGGAGCAGTATTCCCTGAACGAGATCATCAACAACTTC

AACGGCATCAGGATCAAGACAGATTACCACTCTCTGCTGGACAAGAAGGAGAA

GGAGAGGTTCGAGGCCCGCCAGAACTGGACCTCCATCGAGAATATCAAGGAGC
```

-continued

TGAAGGCCGGCTATATCTCTCAGGTGGTGCACAAGATCTGCGAGCTGGTGGAGA

AGTACGATGCCGTGATCGCCCTGGAGGACCTGAACTCTGGCTTTAAGAATAGCC

GCGTGAAGGTGGAGAAGCAGGTGTATCAGAAGTTCGAGAAGATGCTGATCGAT

AAGCTGAACTACATGGTGGACAAGAAGTCTAATCCTTGTGCAACAGGCGGCGCC

CTGAAGGGCTATCAGATCACCAATAAGTTCGAGAGCTTTAAGTCCATGTCTACCC

AGAACGGCTTCATCTTTTACATCCCTGCCTGGCTGACATCCAAGATCGATCCATC

TACCGGCTTTGTGAACCTGCTGAAAACCAAGTATACCAGCATCGCCGATTCCAA

GAAGTTCATCAGCTCCTTTGACAGGATCATGTACGTGCCCGAGGAGGATCTGTT

CGAGTTTGCCCTGGACTATAAGAACTTCTCTCGCACAGACGCCGATTACATCAA

GAAGTGGAAGCTGTACTCCTACGGCAACCGGATCAGAATCTTCCGGAATCCTAA

GAAGAACAACGTGTTCGACTGGGAGGAGGTGTGCCTGACCAGCGCCTATAAGG

AGCTGTTCAACAAGTACGGCATCAATTATCAGCAGGGCGATATCAGAGCCCTGC

TGTGCGAGCAGTCCGACAAGGCCTTCTACTCTAGCTTTATGGCCCTGATGAGCCT

GATGCTGCAGATGCGGAACAGCATCACAGGCCGCACCGACGTGGATTTTCTGAT

CAGCCCTGTGAAGAACTCCGACGGCATCTTCTACGATAGCCGGAACTATGAGGC

CCAGGAGAATGCCATCCTGCCAAAGAACGCCGACGCCAATGGCGCCTATAACA

TCGCCAGAAAGGTGCTGTGGGCCATCGGCCAGTTCAAGAAGGCCGAGGACGAG

AAGCTGGATAAGGTGAAGATCGCCATCTCTAACAAGGAGTGGCTGGAGTACGCC

CAGACCAGCGTGAAGCAC*AAAAGGCCGGCGGCCACGAAAAAGGCCGGCCAGGC*

*AAAAAAGAAAAAGGGATCC*tacccatacgatgttccagattacgcttatccctacgacgtgcctgattatgcata cccatatgatgtccccgactatgccTCGAGCGACTACAAAGACCATGACGGTGATTATAAAGAT

CATGACATCGATTACAAGGATGACGATGACAAGGCTGCAGGAGGCGGTGGAAGC

GGGaggggagtgcaggtggaaaccatctccccaggagacgggcgcaccttccccaagcgcggccagac ctgcgtggtgcactacaccgggatgcttgaagatggaaagaaatttgattcctcccgggacagaaacaagccc tttaagtttatgctaggcaagcaggaggtgatccgaggctgggaagaagggggttgcccagatgagtgtgggtc agagagccaaactgactatatctccagattatgcctatggtgccactgggcacccaggcatcatcccaccacat gccactctcgtcttcgatgtggagcttctaaaactggaaggatctggtggaaGCGGGaggggagtgcaggtg gaaaccatctccccaggagacgggcgcaccttccccaagcgcggccagacctgcgtggtgcactacaccgg gatgcttgaagatggaaagaaatttgattcctcccgggacagaaacaagcccttaagtttatgctaggcaagca ggaggtgatccgaggctgggaagaaggggttgcccagatgagtgtgggtcagagagccaaactgactatatc tccagattatgcctatggtgccactgggcacccaggcatcatcccaccacatgccactctcgtcttcgatgtgga gcttctaaaactggaaGGTTCTaggggagtgcaggtggaaaccatctccccaggagacgggcgcaccttc cccaagcgcggccagacctgcgtggtgcactacaccgggatgcttgaagatggaaagaaatttgattcctccc gggacagaaacaagcccttaagtttatgctaggcaagcaggaggtgatccgaggctgggaagaaggggttg cccagatgagtgtgggtcagagagccaaactgactatatctccagattatgcctatggtgccactgggcaccca ggcatcatcccaccacatgccactctcgtcttcgatgtggagcttctaaaactggaaGGATAA 9. YET1000: CAG-human dLbCpf1(D832A)-NLS-3× HA-DmrA(X4)

Human codon optimized dLbCpf1: bold, NLS: italic, 3xHA: lowercase, DmrA: lowercase and bold (SEQ ID NO: 56)

ATGAGCAAGCTGGAGAAGTTTACAAACTGCTACTCCCTGTCTAAGACCCTGAGG

TTCAAGGCCATCCCTGTGGGCAAGACCCAGGAGAACATCGACAATAAGCGGCT

GCTGGTGGAGGACGAGAAGAGAGCCGAGGATTATAAGGGCGTGAAGAAGCTGC

TGGATCGCTACTATCTGTCTTTTATCAACGACGTGCTGCACAGCATCAAGCTGAA

GAATCTGAACAATTACATCAGCCTGTTCCGGAAGAAAACCAGAACCGAGAAGGA

GAATAAGGAGCTGGAGAACCTGGAGATCAATCTGCGGAAGGAGATCGCCAAGG

CCTTCAAGGGCAACGAGGGCTACAAGTCCCTGTTTAAGAAGGATATCATCGAGA

CAATCCTGCCAGAGTTCCTGGACGATAAGGACGAGATCGCCCTGGTGAACAGCT

TCAATGGCTTTACCACAGCCTTCACCGGCTTCTTTGATAACAGAGAGAATATGTT

TTCCGAGGAGGCCAAGAGCACATCCATCGCCTTCAGGTGTATCAACGAGAATCT

GACCCGCTACATCTCTAATATGGACATCTTCGAGAAGGTGGACGCCATCTTTGAT

AAGCACGAGGTGCAGGAGATCAAGGAGAAGATCCTGAACAGCGACTATGATGT

GGAGGATTTCTTTGAGGGCGAGTTCTTTAACTTTGTGCTGACACAGGAGGGCATC

GACGTGTATAACGCCATCATCGGCGGCTTCGTGACCGAGAGCGGCGAGAAGAT

CAAGGGCCTGAACGAGTACATCAACCTGTATAATCAGAAAACCAAGCAGAAGCT

GCCTAAGTTTAAGCCACTGTATAAGCAGGTGCTGAGCGATCGGGAGTCTCTGAG

CTTCTACGGCGAGGGCTATACATCCGATGAGGAGGTGCTGGAGGTGTTTAGAAA

CACCCTGAACAAGAACAGCGAGATCTTCAGCTCCATCAAGAAGCTGGAGAAGCT

GTTCAAGAATTTTGACGAGTACTCTAGCGCCGGCATCTTTGTGAAGAACGGCCC

CGCCATCAGCACAATCTCCAAGGATATCTTCGGCGAGTGGAACGTGATCCGGGA

CAAGTGGAATGCCGAGTATGACGATATCCACCTGAAGAAGAAGGCCGTGGTGA

CCGAGAAGTACGAGGACGATCGGAGAAAGTCCTTCAAGAAGATCGGCTCCTTTT

CTCTGGAGCAGCTGCAGGAGTACGCCGACGCCGATCTGTCTGTGGTGGAGAAG

CTGAAGGAGATCATCATCCAGAAGGTGGATGAGATCTACAAGGTGTATGGCTCC

TCTGAGAAGCTGTTCGACGCCGATTTTGTGCTGGAGAAGAGCCTGAAGAAGAAC

GACGCCGTGGTGGCCATCATGAAGGACCTGCTGGATTCTGTGAAGAGCTTCGAG

AATTACATCAAGGCCTTCTTTGGCGAGGGCAAGGAGACAAACAGGGACGAGTC

CTTCTATGGCGATTTTGTGCTGGCCTACGACATCCTGCTGAAGGTGGACCACATC

TACGATGCCATCCGCAATTATGTGACCCAGAAGCCCTACTCTAAGGATAAGTTCA

AGCTGTATTTTCAGAACCCTCAGTTCATGGGCGGCTGGGACAAGGATAAGGAGA

CAGACTATCGGGCCACCATCCTGAGATACGGCTCCAAGTACTATCTGGCCATCA

TGGATAAGAAGTACGCCAAGTGCCTGCAGAAGATCGACAAGGACGATGTGAAC

GGCAATTACGAGAAGATCAACTATAAGCTGCTGCCCGGCCCTAATAAGATGCTG

CCAAAGGTGTTCTTTTCTAAGAAGTGGATGGCCTACTATAACCCCAGCGAGGAC

ATCCAGAAGATCTACAAGAATGGCACATTCAAGAAGGGCGATATGTTTAACCTG

AATGACTGTCACAAGCTGATCGACTTCTTTAAGGATAGCATCTCCCGGTATCCAA

AGTGGTCCAATGCCTACGATTTCAACTTTTCTGAGACAGAGAAGTATAAGGACAT

CGCCGGCTTTTACAGAGAGGTGGAGGAGCAGGGCTATAAGGTGAGCTTCGAGT

-continued

```
CTGCCAGCAAGAAGGAGGTGGATAAGCTGGTGGAGGAGGGCAAGCTGTATATG
TTCCAGATCTATAACAAGGACTTTTCCGATAAGTCTCACGGCACACCCAATCTGC
ACACCATGTACTTCAAGCTGCTGTTTGACGAGAACAATCACGGACAGATCAGGC
TGAGCGGAGGAGCAGAGCTGTTCATGAGGCGCGCCTCCCTGAAGAAGGAGGAG
CTGGTGGTGCACCCAGCCAACTCCCCTATCGCCAACAAGAATCCAGATAATCCC
AAGAAAACCACAACCCTGTCCTACGACGTGTATAAGGATAAGAGGTTTTCTGAG
GACCAGTACGAGCTGCACATCCCAATCGCCATCAATAAGTGCCCCAAGAACATC
TTCAAGATCAATACAGAGGTGCGCGTGCTGCTGAAGCACGACGATAACCCCTAT
GTGATCGGCATCGCCAGGGGCGAGCGCAATCTGCTGTATATCGTGGTGGTGGAC
GGCAAGGGCAACATCGTGGAGCAGTATTCCCTGAACGAGATCATCAACAACTTC
AACGGCATCAGGATCAAGACAGATTACCACTCTCTGCTGGACAAGAAGGAGAA
GGAGAGGTTCGAGGCCCGCCAGAACTGGACCTCCATCGAGAATATCAAGGAGC
TGAAGGCCGGCTATATCTCTCAGGTGGTGCACAAGATCTGCGAGCTGGTGGAGA
AGTACGATGCCGTGATCGCCCTGGAGGACCTGAACTCTGGCTTTAAGAATAGCC
GCGTGAAGGTGGAGAAGCAGGTGTATCAGAAGTTCGAGAAGATGCTGATCGAT
AAGCTGAACTACATGGTGGACAAGAAGTCTAATCCTTGTGCAACAGGCGGCGCC
CTGAAGGGCTATCAGATCACCAATAAGTTCGAGAGCTTTAAGTCCATGTCTACCC
AGAACGGCTTCATCTTTTACATCCCTGCCTGGCTGACATCCAAGATCGATCCATC
TACCGGCTTTGTGAACCTGCTGAAAACCAAGTATACCAGCATCGCCGATTCCAA
GAAGTTCATCAGCTCCTTTGACAGGATCATGTACGTGCCCGAGGAGGATCTGTT
CGAGTTTGCCCTGGACTATAAGAACTTCTCTCGCACAGACGCCGATTACATCAA
GAAGTGGAAGCTGTACTCCTACGGCAACCGGATCAGAATCTTCCGGAATCCTAA
GAAGAACAACGTGTTCGACTGGGAGGAGGTGTGCCTGACCAGCGCCTATAAGG
AGCTGTTCAACAAGTACGGCATCAATTATCAGCAGGGCGATATCAGAGCCCTGC
TGTGCGAGCAGTCCGACAAGGCCTTCTACTCTAGCTTTATGGCCCTGATGAGCCT
GATGCTGCAGATGCGGAACAGCATCACAGGCCGCACCGACGTGGATTTTCTGAT
CAGCCCTGTGAAGAACTCCGACGGCATCTTCTACGATAGCCGGAACTATGAGGC
CCAGGAGAATGCCATCCTGCCAAAGAACGCCGACGCCAATGGCGCCTATAACA
TCGCCAGAAAGGTGCTGTGGGCCATCGGCCAGTTCAAGAAGGCCGAGGACGAG
AAGCTGGATAAGGTGAAGATCGCCATCTCTAACAAGGAGTGGCTGGAGTACGCC
CAGACCAGCGTGAAGCACAAAAGGCCGGCGGCCACGAAAAAGGCCGGCCAGGC
AAAAAAGAAAAAGGGATCCtacccatacgatgttccagattacgcttatccctacgacgtgcctgattatgcata
cccatatgatgtcccccgactatgccTCGAGCGACTACAAAGACCATGACGGTGATTATAAAGAT
CATGACATCGATTACAAGGATGACGATGACAAGGCTGCAGGAGGCGGTGGAAGC
GGGGGAaggggagtgcaggtggaaaccatctccccaggagacgggcgcaccttccccaagcgcggcca
gacctgcgtggtgcactacaccgggatgcttgaagatggaaagaaatttgattcctcccgggacagaaacaag
ccctttaagtttatgctaggcaagcaggaggtgatccgaggctgggaagaaggggttgcccagatgagtgtgg
gtcagagagccaaactgactatatctccagattatgcctatggtgccactgggcacccaggcatcatcccacca
catgccactctcgtcttcgatgtggagcttctaaaactggaaGGTTCTaggggagtgcaggtggaaaccatct
ccccaggagacgggcgcaccttccccaagcgcggccagacctgcgtggtgcactacaccgggatgcttgaa
```

-continued

```
gatggaaagaaatttgattcctcccggacagaaacaagccctttaagtttatgctaggcaagcaggaggtgat ccgaggctgggaagaaggggttgcccagatgagtgtgggtcagagagccaaactgactatatctccagattat gcctatggtgccactgggcacccaggcatcatcccaccacatgccactctcgtcttcgatgtggagcttctaaaa ctggaaGGGGGAAGCGGTGGAAGCGGGaggggagtgcaggtggaaaccatctccccaggagac gggcgcaccttccccaagcgcggccagacctgcgtggtgcactacaccgggatgcttgaagatggaaagaa atttgattcctcccgggacagaaacaagccctttaagtttatgctaggcaagcaggaggtgatccgaggctggg aagaaggggttgcccagatgagtgtgggtcagagagccaaactgactatatctccagattatgcctatggtgcc actgggcacccaggcatcatcccaccacatgccactctcgtcttcgatgtggagcttctaaaactggaaGGTT CTaggggagtgcaggtggaaaccatctccccaggagacgggcgcaccttccccaagcgcggccagacctg cgtggtgcactacaccgggatgcttgaagatggaaagaaatttgattcctcccgggacagaaacaagcccttta agtttatgctaggcaagcaggaggtgatccgaggctgggaagaaggggttgcccagatgagtgtgggtcaga gagccaaactgactatatctccagattatgcctatggtgccactgggcacccaggcatcatcccaccacatgcc actctcgtcttcgatgtggagcttctaaaactggaaGGATAA
```

10. BPK3082: U6-Lb-crRNA-BsmBIcassette

U6 promoter: bold, Lb crRNA: italic, BsmBI sites: lower case, U6 terminator: italic and bold (SEQ ID NO: 57)
```
TGTACAAAAAAGCAGGCTTTAAAGGAACCAATTCAGTCGACTGGATCCG

GTACCAAGGTCGGGCAGGAAGAGGGCCTATTTCCCATGATTCCTTCATA

TTTGCATATACGATACAAGGCTGTTAGAGAGATAATTAGAATTAATTTG

ACTGTAAACACAAAGATATTAGTACAAAATACGTGACGTAGAAAGTAAT

AATTTCTTGGGTAGTTTGCAGTTTTAAAATTATGTTTTAAAATGGACTA

TCATATGCTTACCGTAACTTGAAAGTATTTCGATTTCTTGGCTTTATAT

ATCTTGTGGAAAGGACGAAACACCGAATTTCTACTAAGTGTAGATGgag acgATTAATGcgtctcCTTTTTTT
```

11. FIG. 2b_sequence hU6 promoter: bold, Lb crRNA direct repeats: italic, crRNA1_HBB spacer sequence: lower case, crRNA3_AR spacer sequence: lower case and bold, crRNA1_NPY1R spacer sequence: lower case, bold and italic, terminator: bold and italic (SEQ ID NO: 58)
```
GAGGGCCTATTTCCCATGATTCCTTCATATTTGCATATACGATACAAGG

CTGTTAGAGAGATAATTAGAATTAATTTGACTGTAAACACAAAGATATT

AGTACAAAATACGTGACGTAGAAAGTAATAATTTCTTGGGTAGTTTGCA

GTTTTAAAATTATGTTTTAAAATGGACTATCATATGCTTACCGTAACTT

GAAAGTATTTCGATTTCTTGGCTTTATATATCTTGTGGAAAGGACGAAA

CACCGAATTTCTACTAAGTGTACATtactgatggtatggggccaaAATT

TCTACTAACTCTACATctctaggaaccctcagccccAATTTCTACTAAG

TGTAGATaagcctcgggaaactgccctAATTTCTACTAAGTGTAGA

TTTTTTTT
```

REFERENCES

1. Maeder, M. L. et al. CRISPR RNA-guided activation of endogenous human genes. *Nat Methods* 10, 977-979 (2013).
2. Perez-Pinera, P. et al. RNA-guided gene activation by CRISPR-Cas9-based transcription factors. *Nat Methods* 10, 973-976 (2013).
3. Gilbert, L. A. et al. Genome-Scale CRISPR-Mediated Control of Gene Repression and Activation. *Cell* 159, 647-661 (2014).
4. Shen, J. P. et al. Combinatorial CRISPR-Cas9 screens for de novo mapping of genetic interactions. *Nature methods* (2017).
5. Chavez, A. et al. Comparison of Cas9 activators in multiple species. *Nature methods* 13, 563-567 (2016).
6. Zetsche, B., Volz, S. E. & Zhang, F. A split-Cas9 architecture for inducible genome editing and transcription modulation. *Nature biotechnology* 33, 139-142 (2015).
7. Guo, J. et al. An inducible CRISPR-ON system for controllable gene activation in human pluripotent stem cells. *Protein & cell* (2017).
8. Bao, Z., Jain, S., Jaroenpuntaruk, V. & Zhao, H. Orthogonal Genetic Regulation in Human Cells Using Chemically Induced CRISPR/Cas9 Activators. *ACS synthetic biology* (2017).
9. Polstein, L. R. & Gersbach, C. A. A light-inducible CRISPR-Cas9 system for control of endogenous gene activation. *Nature chemical biology* 11, 198-200 (2015).
10. Maji, B. et al. Multidimensional chemical control of CRISPR-Cas9. *Nature chemical biology* 13, 9-11 (2017).
11. Fonfara, I., Richter, H., Bratovic, M., Le Rhun, A. & Charpentier, E. The CRISPR-associated DNA-cleaving enzyme Cpf1 also processes precursor CRISPR RNA. *Nature* 532, 517-521 (2016).
12. Kim, S. K. et al. Efficient Transcriptional Gene Repression by Type V-A CRISPR-Cpf1 from Eubacterium eligens. *ACS synthetic biology* (2017).
13. Tang, X. et al. A CRISPR-Cpf1 system for efficient genome editing and transcriptional repression in plants. *Nature plants* 3, 17018 (2017).
14. Kleinstiver, B. P. et al. Genome-wide specificities of CRISPR-Cas Cpf1 nucleases in human cells. *Nature biotechnology* 34, 869-874 (2016).

15. Kim, D. et al. Genome-wide analysis reveals specificities of Cpf1 endonucleases in human cells. *Nature biotechnology* 34, 863-868 (2016).
16. Matis, C., Chomez, P., Picard, J. & Rersohazy, R. Differential and opposed transcriptional effects of protein fusions containing the VP16 activation domain. *FEBS letters* 499, 92-96 (2001).
17. Lin, H., McGrath, J., Wang, P. & Lee, T. Cellular toxicity induced by SRF-mediated transcriptional squelching. *Toxicological sciences: an official journal of the Society of Toxicology* 96, 83-91 (2007).
18. Han, K. et al. Synergistic drug combinations for cancer identified in a CRISPR screen for pairwise genetic interactions. *Nature biotechnology* (2017).
19. Tsai, S. Q. et al. Dimeric CRISPR RNA-guided FokI nucleases for highly specific genome editing. *Nat Biotechnol* 32, 569-576 (2014).
20. Nissim, L., Perli, S. D., Fridkin, A., Perez-Pinera, P. & Lu, T. K. Multiplexed and programmable regulation of gene networks with an integrated RNA and CRISPR/Cas toolkit in human cells. *Molecular cell* 54, 698-710 (2014).
21. Xie, K., Minkenberg, B. & Yang, Y. Boosting CRISPR/Cas9 multiplex editing capability with the endogenous tRNA-processing system. *Proc Natl Acad Sci U S A* 112, 3570-3575 (2015).
22. Xu, L., Zhao, L., Gao, Y., Xu, J. & Han, R. Empower multiplex cell and tissue-specific CRISPR-mediated gene manipulation with self-cleaving ribozymes and tRNA. *Nucleic Acids Res* (2016).
23. Kabadi, A. M., Ousterout, D. G., Hilton, I. B. & Gersbach, C. A. Multiplex CRISPR/Cas9-based genome engineering from a single lentiviral vector. *Nucleic Acids Res* 42, e147 (2014).
24. Wong, A. S. et al. Multiplexed barcoded CRISPR-Cas9 screening enabled by CombiGEM. *Proc Natl Acad Sci USA* 113, 2544-2549 (2016).
25. Adamson, B. et al. A Multiplexed Single-Cell CRISPR Screening Platform Enables Systematic Dissection of the Unfolded Protein Response. *Cell* 167, 1867-1882.e1821 (2016).
26. Wright, A. V., Nunez, J. K. & Doudna, J. A. Biology and Applications of CRISPR Systems: Harnessing Nature's Toolbox for Genome Engineering. *Cell* 164, 29-44 (2016).
27. Sander, J. D. & Joung, J. K. CRISPR-Cas systems for editing, regulating and targeting genomes. *Nat Biotechnol* 32, 347-355 (2014).
28. Hsu, P. D., Lander, E. S. & Zhang, F. Development and applications of CRISPR-Cas9 for genome engineering. *Cell* 157, 1262-1278 (2014).
29. Doudna, J. A. & Charpentier, E. Genome editing. The new frontier of genome engineering with CRISPR-Cas9. *Science* 346, 1258096 (2014).
30. Maeder, M. L. & Gersbach, C. A. Genome-editing Technologies for Gene and Cell Therapy. *Mol Ther* (2016).
31. Jinek, M. et al. A programmable dual-RNA-guided DNA endonuclease in adaptive bacterial immunity. *Science* 337, 816-821 (2012).
32. Deltcheva, E. et al. CRISPR RNA maturation by trans-encoded small RNA and host factor RNase III. *Nature* 471, 602-607 (2011).
33. Cong, L. et al. Multiplex genome engineering using CRISPR/Cas systems. *Science* 339, 819-823 (2013).
34. Mali, P. et al. RNA-guided human genome engineering via Cas9. *Science* 339, 823-826 (2013).
35. Jinek, M. et al. RNA-programmed genome editing in human cells. *Elife* 2, e00471 (2013).
36. Tsai, S. Q. et al. GUIDE-seq enables genome-wide profiling of off-target cleavage by CRISPR-Cas nucleases. *Nat Biotechnol* 33, 187-197 (2015).
37. Frock, R. L. et al. Genome-wide detection of DNA double-stranded breaks induced by engineered nucleases. *Nat Biotechnol* 33, 179-186 (2015).
38. Wang, X. et al. Unbiased detection of off-target cleavage by CRISPR-Cas9 and TALENs using integrase-defective lentiviral vectors. *Nat Biotechnol* 33, 175-178 (2015).
39. Kim, D. et al. Digenome-seq: genome-wide profiling of CRISPR-Cas9 off-target effects in human cells. *Nat Methods* 12, 237-243, 231 p following 243 (2015).
40. Kleinstiver, B. P. et al. High-fidelity CRISPR-Cas9 nucleases with no detectable genome-wide off-target effects. *Nature* 529, 490-495 (2016).
41. Slaymaker, I. M. et al. Rationally engineered Cas9 nucleases with improved specificity. *Science* 351, 84-88 (2016).
42. Schunder, E., Rydzewski, K., Grunow, R. & Heuner, K. First indication for a functional CRISPR/Cas system in *Francisella tularensis*. *Int J Med Microbiol* 303, 51-60 (2013).
43. Makarova, K. S. et al. An updated evolutionary classification of CRISPR-Cas systems. *Nat Rev Microbiol* 13, 722-736 (2015).
44. Zetsche, B. et al. Cpf1 Is a Single RNA-Guided Endonuclease of a Class 2 CRISPR-Cas System. *Cell* 163, 759-771 (2015).
45. Fagerlund, R. D., Staals, R. H. & Fineran, P. C. The Cpf1 CRISPR-Cas protein expands genome-editing tools. *Genome Biol* 16, 251 (2015).
46. Chavez, A. et al. Highly efficient Cas9-mediated transcriptional programming. *Nature methods* 12, 326-328 (2015).
47. Konermann, S. et al. Genome-scale transcriptional activation by an engineered CRISPR-Cas9 complex. *Nature* 517, 583-588 (2015).
48. Rivera, V. M., Berk, L. & Clackson, T. Dimerizer-mediated regulation of gene expression in vivo. *Cold Spring Harbor protocols* 2012, 821-824 (2012).
49. Zetsche, B. et al. Multiplex gene editing by CRISPR-Cpf1 using a single crRNA array. *Nature biotechnology* 35, 31-34 (2017).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising: (a) a first fusion protein comprising a catalytically inactive Lachnospiraceae bacterium ND2006 Cpf1 (dLbCpf1) fused to more than one first dimerization domains, and (b) a second fusion protein comprising at least one activation domain fused to a second dimerization domain that dimerizes with at least one of the first dimerization domains in the first fusion protein in the presence of a dimerizing agent, wherein the first and second dimerization domains are rapamycin analog A/C heterodimerizer DmrA or DmrC.

2. The composition of claim 1, wherein (i) the first dimerization domain in the first fusion protein is DmrA, and the second dimerization domain in the second fusion protein is DmrC, or (ii) the first dimerization domain in the first fusion protein is DmrC, and the second dimerization domain in the second fusion protein is DmrA.

3. The composition of claim 1, wherein the activation domain is a transcriptional activation domain from herpes simplex viral protein 16 (VP64), Epstein-Barr virus R transactivator (Rta), p65 domain from cellular transcription factor NF-κB (NF-κB p65), or a tripartite effector composed of VP64, p65, and Rta (VPR).

4. A nucleic acid encoding the first fusion protein (a) of claim 1 and the second fusion protein (b) of claim 1.

5. A kit comprising a nucleic acid encoding the first fusion protein (a) of claim 1 and a second nucleic acid encoding the second fusion protein (b) of claim 1.

6. The kit of claim 5, wherein (i) the first dimerization domain in the first fusion protein is DmrA, and the second dimerization domain in the second fusion protein is DmrC, or (ii) the first dimerization domain in the first fusion protein is DmrC, and the second dimerization domain in the second fusion protein is DmrA.

7. An isolated recombinant host cell expressing (i) the first fusion protein (a) of claim 1 and (ii) the second fusion protein (b) of claim 1, wherein the first dimerization domain dimerizes with the second dimerization domain in the presence of a dimerizing agent.

8. The isolated recombinant host cell of claim 7, wherein (i) the first dimerization domain in the first fusion protein is DmrA, and the second dimerization domain in the second fusion protein is DmrC, or (ii) the first dimerization domain in the first fusion protein is DmrC, and the second dimerization domain in the second fusion protein is DmrA.

9. The composition of claim 1, further comprising an intervening linker between each of the activation domain(s) or the second dimerization domain.

10. The composition of claim 1, wherein the first fusion protein is fused to two, three or four first dimerization domains.

11. The kit of claim 5, further comprising an intervening linker between each of the activation domain(s) or the second dimerization domain.

12. The kit of claim 5, wherein the first fusion protein is fused to two, three or four first dimerization domains.

13. The cell of claim 7, further comprising an intervening linker between each of the activation domain(s) or the second dimerization domain.

14. The cell of claim 7, wherein the first fusion protein is fused to two, three or four first dimerization domains.

* * * * *

UNITED STATES PATENT AND TRADEMARK OFFICE
CERTIFICATE OF CORRECTION

| | | |
|---|---|---|
| PATENT NO. | : 11,667,677 B2 | |
| APPLICATION NO. | : 16/606680 | |
| DATED | : June 6, 2023 | |
| INVENTOR(S) | : Tak et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 771 days.

Signed and Sealed this
Twelfth Day of November, 2024

Katherine Kelly Vidal
*Director of the United States Patent and Trademark Office*